US012760374B2

(12) United States Patent
Levy et al.

(10) Patent No.: US 12,760,374 B2
(45) Date of Patent: Oct. 13, 2026

(54) CELL-FREE DNA HYDROXYMETHYLATION PROFILES IN THE EVALUATION OF PANCREATIC LESIONS

(71) Applicant: ClearNote Health, Inc., San Mateo, CA (US)

(72) Inventors: Samuel Levy, San Mateo, CA (US); Patrick A. Arensdorf, Palo Alto, CA (US); Chin-Jen Ku, San Mateo, CA (US); Francois Collin, San Mateo, CA (US)

(73) Assignee: ClearNote Health, Inc., San Diego, CA (US)

( * ) Notice: Subject to any disclaimer, the term of this patent is extended or adjusted under 35 U.S.C. 154(b) by 0 days.

(21) Appl. No.: 18/105,167

(22) Filed: Feb. 2, 2023

(65) Prior Publication Data

US 2024/0026459 A1 Jan. 25, 2024

Related U.S. Application Data

(63) Continuation of application No. 16/576,703, filed on Sep. 19, 2019, now abandoned.

(60) Provisional application No. 62/733,566, filed on Sep. 19, 2018.

(51) Int. Cl.
*C12Q 1/6886* (2018.01)
*G06F 17/18* (2006.01)
*G16H 50/30* (2018.01)

(52) U.S. Cl.
CPC ........... *C12Q 1/6886* (2013.01); *G06F 17/18* (2013.01); *G16H 50/30* (2018.01); *C12Q 2537/164* (2013.01); *C12Q 2600/154* (2013.01); *C12Q 2600/158* (2013.01); *G01N 2800/60* (2013.01); *G01N 2800/7028* (2013.01)

(58) Field of Classification Search
CPC .................... C12Q 2537/164; C12Q 2600/154
See application file for complete search history.

(56) References Cited

U.S. PATENT DOCUMENTS

| | | | |
|---|---|---|---|
| 8,632,983 B2 | 1/2014 | Haab et al. | |
| 11,041,866 B2 | 6/2021 | Williams et al. | |

FOREIGN PATENT DOCUMENTS

| | | | | |
|---|---|---|---|---|
| CN | 10735050 A | 11/2017 | | |
| WO | 2011127136 A1 | 10/2011 | | |
| WO | WO-2012178034 A2 * | 12/2012 | ........... C12Q 1/6886 | |
| WO | 2017176630 A1 | 10/2017 | | |

OTHER PUBLICATIONS

Song et al. Cell Research. 2017. 27:1231-1242. (Year: 2017).*
Wever et al. Molecular Oncology. 2024. 17 pages. (Year: 2024).*
Jaworski et al. Cancers. 2020. 12:3704, 16 pages. (Year: 2020).*
Markus et al. Sci. Transl. Med. 2021. 13:eaaz3088, 16 pages. (Year: 2021).*
Salfer et al. Clin Chem. 2022. 68(12):1493-1501. (Year: 2022).*
Zhang et al. Gastroenterology. 2010. 138(3):949-957. (Year: 2010).*
Geli et al. Cell Stress. 2024. 8:59-68. (Year: 2024).*
Bunduc et al. Clinical Reviews in Oncology. 2022. 169:1035-48. (Year: 2022).*
"PCT Search Report and Written Opinion, PCT/US2019/052026", Jan. 27, 2020.
Fonseca, Annabelle L., et al., "Intraductal Papillary Mucinous Neoplasms of the Pancreas: Current Understanding and Future Directions for Stratification of Malignancy Risk", Pancreas 47(3), Mar. 2018, pp. 272-279.
Collin, Francois, et al., "Detection of early stage pancreatic cancer using 5-hydroxymethylcytosine signatures in circulating cell free DNA", XP055658359, DOI: 10.1101/422675. Retrieved from the Internet: URL:https://www.biorxiv.org/content/10.110 1/422675vl.full.pdf, Sep. 20, 2018.
Guler, Gulfem D., et al., "Detection of early stage pancreatic cancer using 5-hydroxymethylcytosine signatures in circulating cell free DNA", Nature Communications, 11(1): 5270; https://doi.org/10.1038/s41467-020-18965-w, 2020, 12 pages.
Kleeff, Jorg , et al., "Pancreatic cancer", Nature Reviews, Disease Primers: Pancreatic Cancer, vol. 2, Apr. 21, 2016, pp. 1-22.
Lal, Geeta , et al., "Inherited Predisposition to Pancreatic Adenocarcinoma: Role of Family History and Germ-Line p16, BRCA1, and BRCA2 Mutations", Cancer Research, vol. 60, Jan. 15, 2000, pp. 409-416.
Li, Wenshuai , et al., "5-Hydroxymethylcytosine signatures in circulating cell-free DNA as diagnostic biomarkers for human cancers", Cell Research—Xibao Yanjiu, vol. 27, No. 10, Sep. 19, 2017, pp. 1243-125.
Bhattacharyya, Sanchari, et al., "Altered hydroxymethylation is seen at regulatory regions in pancreatic cancer and regulates oncogenic pathways", Genome Research, vol. 27, No. 11,, Oct. 6, 2017, pp. 1830-1842.
Schlieman, Michael G., et al., "Utility of Tumor Markers in Determining Resectability of Pancreatic Cancer", Arch Surg. vol. 138, Sep. 2003, pp. 951-956.
Song, Chun-Xiao , et al., "5-Hydroxymethylcytosine signatures in cellfree DNA provide information about tumor ypes and stages", Cell Research—Xibao Yanjiu, vol. 27, No. 10, XP055540434, GB, CN ISSN: 1001-0602, DOI: 10.1038/cr.2017.106 ; & Chun-Xiao Song:, Aug. 18, 2017, pp. 1231-1242.

(Continued)

*Primary Examiner* — Joseph G. Dauner
(74) *Attorney, Agent, or Firm* — Doreen Yatko Trujillo; VLP Law Group LLP

(57) ABSTRACT

Disclosed herein are methods for identifying patients with pancreatic cancer and subjects at risk for developing pancreatic cancer, methods for monitoring a patient with an identified pancreatic lesion, methods for evaluating the effectiveness of a treatment used for a patient with pancreatic cancer, and methods for selecting a therapy for treating pancreatic cancer in a particular patient. The invention makes use of hydroxymethylation biomarkers, which in combination with one or more clinical parameters and optionally one or more additional types of biomarkers and/or patient-specific risk factors, exhibit a hydroxymethylation level that correlates with pancreatic cancer. Kits and other methods of use are also provided.

6 Claims, 37 Drawing Sheets

(56) References Cited

OTHER PUBLICATIONS

Song, Chun-Xiao , et al., "5-Hydroxymethylcytosine signatures in cell-free DNA provide information about tumor types and stages", Cell Research—Xibao Yanjiu, vol. 27, No. 10, Aug. 18, 2017, pp. 1231-1242.

Swords, Douglas S., et al., "Biomarkers in pancreatic adenocarcinoma: current perspectives", OncoTargets and Therapy, 9, 2016, pp. 7459-7467.

* cited by examiner

| Location (chr) | Gene | glmnet | glmnet2 | GlmnetF | Glmnet2F | glmnetF. coefficient | Glmnet2F coefficient | Mean | SD | NC-Mean | NC-SD | C-Mean | C-SD | Vote | C/NC Means |
|---|---|---|---|---|---|---|---|---|---|---|---|---|---|---|---|
| chr01 | LGALS8-AS1 | NA | NA | 40 | 32 | -0.168 | -0.254 | 0.892 | 0.675 | 1.315 | 0.518 | 0.552 | 0.591 | 72 | 0.419771863 |
| chr18 | DYNAP | NA | NA | 43 | 27 | -0.181 | -0.209 | 1.184 | 0.534 | 1.423 | 0.497 | 0.991 | 0.486 | 70 | 0.696416022 |
| chr20 | LINC00266-1 | NA | NA | 35 | 27 | 0.148 | 0.213 | 0.763 | 0.454 | 0.582 | 0.374 | 0.909 | 0.463 | 62 | 1.56185567 |
| chr02 | IL36G | NA | NA | 29 | 29 | -0.12 | -0.225 | 1.74 | 0.409 | 1.933 | 0.329 | 1.586 | 0.404 | 58 | 0.820486291 |
| chr07 | CLK2P | NA | NA | 30 | 24 | 0.125 | 0.19 | 0.907 | 0.513 | 0.824 | 0.556 | 0.974 | 0.471 | 54 | 1.182038835 |
| chr03 | GPX1 | NA | NA | 25 | 22 | -0.107 | -0.172 | 0.257 | 0.469 | 0.422 | 0.46 | 0.124 | 0.438 | 47 | 0.293838863 |
| chr13 | GAS6 | NA | NA | 28 | 18 | 0.119 | 0.138 | 6.961 | 0.199 | 6.896 | 0.16 | 7.013 | 0.213 | 46 | 1.016966357 |
| chr14 | PPP1R3E | NA | NA | 30 | 12 | -0.126 | -0.098 | 2.949 | 0.288 | 3.057 | 0.272 | 2.862 | 0.272 | 42 | 0.936211973 |
| chr12 | LOC100288778 | NA | NA | 19 | 1818 | -0.08 | -0.139 | 1.298 | 0.601 | 1.522 | 0.521 | 1.117 | 0.605 | 1837 | 0.73390276 |
| chr03 | FAM86JP | NA | NA | 33 | NA | 0.137 | NA | 3.405 | 0.361 | 3.135 | 0.279 | 3.622 | 0.259 | 33 | 1.155342903 |
| chr06 | VGLL2 | NA | NA | 26 | 5 | -0.108 | -0.042 | 1.078 | 0.53 | 1.142 | 0.521 | 1.026 | 0.536 | 31 | 0.898423818 |
| chr19 | KLK2 | NA | NA | 14 | 17 | -0.057 | -0.136 | 1.459 | 0.408 | 1.592 | 0.468 | 1.353 | 0.319 | 31 | 0.849874372 |
| chr01 | LOC100130557 | NA | NA | 21 | 5 | -0.088 | -0.036 | 2.226 | 0.372 | 2.277 | 0.352 | 2.185 | 0.385 | 26 | 0.95959596 |
| chr09 | FAM166A | NA | NA | 13 | 11 | 0.054 | 0.085 | 3.846 | 0.265 | 3.741 | 0.236 | 3.931 | 0.258 | 24 | 1.050788559 |
| chr15 | ODF3L1 | NA | NA | 19 | 4 | 0.08 | 0.034 | 2.58 | 0.342 | 2.511 | 0.372 | 2.636 | 0.308 | 23 | 1.049780964 |
| chr01 | BOLA1 | NA | NA | 15 | 6 | -0.065 | -0.044 | 1.897 | 0.366 | 2.011 | 0.317 | 1.806 | 0.38 | 21 | 0.898060666 |
| chr01 | PLA2G2E | NA | NA | 19 | NA | 0.079 | NA | 2.315 | 0.426 | 2.082 | 0.377 | 2.502 | 0.37 | 19 | 1.201729107 |
| chr02 | DNAJC27 | NA | NA | 16 | 2 | -0.066 | -0.015 | 4.708 | 0.212 | 4.838 | 0.164 | 4.603 | 0.188 | 18 | 0.951426209 |
| chr10 | ADARB2-AS1 | NA | NA | 17 | NA | -0.072 | NA | 4.132 | 0.31 | 4.265 | 0.296 | 4.025 | 0.281 | 17 | 0.943728019 |
| chr08 | KLHL38 | NA | NA | 17 | NA | -0.07 | NA | 2.139 | 0.409 | 2.224 | 0.416 | 2.069 | 0.393 | 17 | 0.930305755 |
| chr17 | LRRC37A2 | NA | NA | 16 | NA | 0.068 | NA | 2.1 | 0.65 | 1.799 | 0.688 | 2.343 | 0.505 | 16 | 1.302390217 |
| chr01 | CAMSAP2 | NA | NA | 14 | NA | 0.06 | NA | 6.053 | 0.24 | 5.9 | 0.162 | 6.176 | 0.222 | 14 | 1.046779661 |

*FIG. 20A*

| Location (chr) | Gene | glmnet | glmnet2 | GlmnetF | Glmnet2F | glmnetF. coefficient | Glmnet2F coefficient | Mean | SD | NC-Mean | NC-SD | C-Mean | C-SD | Vote | C/NC Means |
|---|---|---|---|---|---|---|---|---|---|---|---|---|---|---|---|
| chr19 | KCTD15 | NA | NA | 4 | 9 | 0.018 | 0.068 | 5.185 | 0.188 | 5.105 | 0.167 | 5.25 | 0.181 | 13 | 1.028403526 |
| chr01 | LOC100505633 | NA | NA | 13 | NA | 0.053 | NA | 3.76 | 0.291 | 3.583 | 0.198 | 3.902 | 0.275 | 13 | 1.089031538 |
| chr17 | KANSL1 | NA | NA | 10 | NA | 0.041 | NA | 8.504 | 0.265 | 8.394 | 0.251 | 8.592 | 0.243 | 10 | 1.023588277 |
| chr16 | LOC100130894 | NA | NA | 10 | NA | -0.043 | NA | 5.365 | 0.244 | 5.487 | 0.187 | 5.267 | 0.241 | 10 | 0.959905231 |
| chr17 | SLC4A1 | NA | NA | 10 | NA | 0.042 | NA | 4.875 | 0.17 | 4.77 | 0.123 | 4.959 | 0.156 | 10 | 1.039622642 |
| chr12 | CSRP2 | NA | NA | 9 | NA | 0.04 | NA | 4.272 | 0.272 | 4.123 | 0.238 | 4.392 | 0.238 | 9 | 1.065243755 |
| chr17 | KCNH6 | NA | NA | 7 | 1 | 0.029 | 0.005 | 4.374 | 0.245 | 4.216 | 0.189 | 4.501 | 0.21 | 8 | 1.06759962 |
| chr02 | ATG4B | NA | NA | 8 | NA | 0.032 | NA | 5.885 | 0.199 | 5.747 | 0.126 | 5.996 | 0.176 | 8 | 1.043326953 |
| chr19 | CRTC1 | NA | NA | 8 | NA | 0.033 | NA | 7.488 | 0.174 | 7.366 | 0.092 | 7.586 | 0.163 | 8 | 1.029866956 |
| chr03 | PLSCR4 | NA | NA | 8 | NA | 0.032 | NA | 5.073 | 0.234 | 4.931 | 0.137 | 5.188 | 0.233 | 8 | 1.052119246 |
| chr17 | C17orf97 | NA | NA | 7 | 0 | -0.031 | -0.002 | 3.024 | 0.309 | 3.186 | 0.221 | 2.894 | 0.31 | 7 | 0.908349027 |
| chr18 | ATP8B1 | NA | NA | 7 | NA | 0.031 | NA | 7.403 | 0.217 | 7.249 | 0.122 | 7.527 | 0.195 | 7 | 1.038350117 |
| chr08 | C8orf74 | NA | NA | 7 | NA | 0.03 | NA | 5.177 | 0.321 | 4.938 | 0.184 | 5.369 | 0.275 | 7 | 1.087282301 |
| chr14 | GLRX5 | NA | NA | 7 | NA | -0.028 | NA | 3.989 | 0.266 | 4.126 | 0.203 | 3.879 | 0.261 | 7 | 0.940135725 |
| chr02 | LOC90784 | NA | NA | 7 | NA | 0.028 | NA | 3.487 | 0.261 | 3.369 | 0.229 | 3.583 | 0.248 | 7 | 1.063520332 |
| chr02 | NEUROD1 | NA | NA | 7 | NA | 0.029 | NA | 0.971 | 0.508 | 0.879 | 0.552 | 1.045 | 0.461 | 7 | 1.188850967 |
| chr01 | SHISA4 | NA | NA | 7 | NA | 0.029 | NA | 2.247 | 0.488 | 1.924 | 0.387 | 2.507 | 0.398 | 7 | 1.303014553 |
| chr04 | FAT4 | NA | NA | 6 | NA | 0.023 | NA | 6.325 | 0.276 | 6.165 | 0.133 | 6.454 | 0.294 | 6 | 1.046877534 |
| chr06 | TDRD6 | NA | NA | 6 | NA | 0.024 | NA | 2.928 | 0.455 | 2.642 | 0.369 | 3.158 | 0.384 | 6 | 1.195306586 |
| chr02 | LOC389033 | NA | NA | 5 | NA | 0.023 | NA | 2.285 | 0.433 | 2.187 | 0.318 | 2.364 | 0.496 | 5 | 1.080932785 |
| chr14 | TMEM253 | NA | NA | 5 | NA | -0.021 | NA | 2.472 | 0.358 | 2.613 | 0.338 | 2.359 | 0.335 | 5 | 0.902793724 |
| chr03 | TTC14 | NA | NA | 5 | NA | -0.022 | NA | 1.872 | 0.419 | 1.978 | 0.378 | 1.786 | 0.435 | 5 | 0.902932255 |
| chr07 | ZNF789 | NA | NA | 5 | NA | -0.023 | NA | 4.282 | 0.199 | 4.357 | 0.156 | 4.222 | 0.212 | 5 | 0.969015378 |
| chr11 | HBD | NA | NA | 4 | NA | -0.018 | NA | 0.658 | 0.522 | 0.88 | 0.443 | 0.48 | 0.516 | 4 | 0.545454545 |

*FIG. 20B*

| Location (chr) | Gene | glmnet | glmnet2 | GlmnetF | Glmnet2F | glmnetF. coefficient | Glmnet2F coefficient | Mean | SD | NC-Mean | NC-SD | C-Mean | C-SD | Vote | C/NC Means |
|---|---|---|---|---|---|---|---|---|---|---|---|---|---|---|---|
| chr01 | C1orf170 | NA | NA | 3 | NA | 0.012 | NA | 3.286 | 0.324 | 3.1 | 0.281 | 3.436 | 0.277 | 3 | 1.108387097 |
| chr12 | CCDC59 | NA | NA | 3 | NA | -0.014 | NA | 1.686 | 0.442 | 1.751 | 0.416 | 1.634 | 0.459 | 3 | 0.933181039 |
| chr17 | GAS2L2 | NA | NA | 3 | NA | 0.013 | NA | 3.024 | 0.301 | 2.897 | 0.301 | 3.127 | 0.262 | 3 | 1.079392475 |
| chr15 | STRA6 | NA | NA | 3 | NA | 0.015 | NA | 4.72 | 0.284 | 4.648 | 0.177 | 4.778 | 0.338 | 3 | 1.027969019 |
| chr02 | LOC100130452 | NA | NA | NA | 2 | NA | -0.012 | 1.574 | 0.427 | 1.677 | 0.364 | 1.491 | 0.458 | 2 | 0.889087657 |
| chr07 | FAM188B | NA | NA | 2 | NA | 0.009 | NA | 6.881 | 0.156 | 6.836 | 0.114 | 6.917 | 0.177 | 2 | 1.011849035 |
| chr06 | FBXO5 | NA | NA | 2 | NA | -0.007 | NA | 3.337 | 0.377 | 3.576 | 0.238 | 3.145 | 0.359 | 2 | 0.879474273 |
| chr05 | LOC100505738 | NA | NA | 2 | NA | 0.008 | NA | 1.656 | 0.513 | 1.413 | 0.505 | 1.852 | 0.435 | 2 | 1.310686483 |
| chr13 | TEX26 | NA | NA | 2 | NA | -0.007 | NA | 3.2 | 0.389 | 3.339 | 0.353 | 3.088 | 0.383 | 2 | 0.924827793 |
| chr02 | WASH2P | NA | NA | 2 | NA | -0.01 | NA | 3.748 | 0.28 | 3.817 | 0.216 | 3.693 | 0.313 | 2 | 0.967513754 |
| chr06 | GPX5 | NA | NA | 1 | 0 | -0.006 | -0.003 | 1.526 | 0.407 | 1.596 | 0.383 | 1.469 | 0.42 | 1 | 0.920426065 |
| chr10 | PGAM1 | NA | NA | 1 | NA | -0.003 | NA | 3.277 | 0.264 | 3.391 | 0.227 | 3.186 | 0.259 | 1 | 0.939545857 |
| chr08 | REXO1L1 | NA | NA | 1 | NA | 0.005 | NA | 1.284 | 0.747 | 1.043 | 0.757 | 1.478 | 0.686 | 1 | 1.417066155 |
| chr22 | RIMBP3 | NA | NA | 1 | NA | 0.002 | NA | 0.443 | 0.438 | 0.314 | 0.447 | 0.546 | 0.406 | 1 | 1.738853503 |
| chr01 | RPS27 | NA | NA | 1 | NA | -0.002 | NA | 0.652 | 0.505 | 0.868 | 0.394 | 0.479 | 0.521 | 1 | 0.551843318 |
| chr08 | SLCO5A1 | NA | NA | 1 | NA | -0.003 | NA | 5.951 | 0.265 | 6.022 | 0.266 | 5.893 | 0.253 | 1 | 0.978578545 |
| chr20 | SRSF6 | NA | NA | 1 | NA | -0.003 | NA | 3.277 | 0.344 | 3.463 | 0.296 | 3.127 | 0.306 | 1 | 0.9029743 |
| chr02 | TUBA4A | NA | NA | 1 | NA | -0.005 | NA | 3.73 | 0.333 | 3.861 | 0.281 | 3.624 | 0.335 | 1 | 0.938616939 |
| chr10 | ASAH2B | NA | NA | NA | 0 | NA | 0 | 1.145 | 0.496 | 1.1 | 0.512 | 1.181 | 0.485 | 0 | 1.073636364 |
| chr19 | LOC100652909 | NA | NA | 0 | NA | -0.001 | NA | 0.744 | 0.562 | 0.923 | 0.526 | 0.601 | 0.554 | 0 | 0.651137595 |
| NA | Intercep | NA | NA | NA | NA | 0.785 | 0.919 | NA | NA | NA | NA | NA | NA | 0 | #VALUE! |
| chr13 | GGACT | 100 | 100 | 93 | 92 | 0.392 | 0.719 | 6.316 | 0.308 | 6.145 | 0.291 | 6.454 | 0.248 | 385 | 1.050284784 |
| chr03 | NPRL2 | 96 | 99 | 100 | 100 | -0.421 | -0.78 | 2.32 | 0.355 | 2.538 | 0.275 | 2.145 | 0.314 | 395 | 0.845153664 |
| chr17 | MED11 | 61 | 55 | 52 | 47 | -0.221 | -0.365 | 1.88 | 0.445 | 2.013 | 0.325 | 1.773 | 0.5 | 215 | 0.880774963 |

FIG. 20C

| Location (chr) | Gene | glmnet | glmnet2 | GlmnetF | Glmnet2F | glmnetF. coefficient | Glmnet2F coefficient | Mean | SD | NC-Mean | NC-SD | C-Mean | C-SD | Vote | C/NC Means |
|---|---|---|---|---|---|---|---|---|---|---|---|---|---|---|---|
| chr15 | LOC100505648 | 61 | 51 | 47 | 44 | -0.197 | -0.345 | 1.529 | 0.428 | 1.722 | 0.394 | 1.373 | 0.393 | 203 | 0.797328688 |
| chr11 | C11orf88 | 60 | 59 | 25 | 27 | -0.106 | -0.208 | 3.158 | 0.321 | 3.322 | 0.274 | 3.026 | 0.296 | 171 | 0.91089705 |
| chr04 | NAT8L | 57 | 59 | 39 | 26 | 0.166 | 0.205 | 4.102 | 0.322 | 3.878 | 0.221 | 4.282 | 0.274 | 181 | 1.104177411 |
| chr01 | LAMC1 | 48 | 44 | 19 | NA | 0.078 | NA | 6.744 | 0.227 | 6.599 | 0.181 | 6.861 | 0.191 | 111 | 1.039702985 |
| chr03 | SLC25A38 | 43 | 40 | 17 | 3 | -0.071 | -0.026 | 3.748 | 0.227 | 3.765 | 0.212 | 3.735 | 0.24 | 103 | 0.992031873 |
| chr05 | NME5 | 39 | 25 | 41 | 52 | -0.172 | -0.409 | 3.56 | 0.301 | 3.727 | 0.207 | 3.426 | 0.299 | 157 | 0.919237993 |
| chr11 | MRPL23-AS1 | 39 | 39 | 4 | NA | 0.015 | NA | 4.492 | 0.346 | 4.3 | 0.196 | 4.646 | 0.364 | 82 | 1.080465116 |
| chr01 | SERTAD4 | 37 | 11 | NA | NA | NA | NA | 2.149 | 0.523 | 2.059 | 0.402 | 2.221 | 0.597 | 48 | 1.07867897 |
| chr19 | LGALS14 | 34 | 19 | 18 | 2 | -0.077 | -0.017 | 1.165 | 0.521 | 1.376 | 0.386 | 0.996 | 0.556 | 73 | 0.723837209 |
| chr17 | WNT9B | 34 | 2 | 15 | NA | 0.062 | NA | 4.802 | 0.234 | 4.659 | 0.168 | 4.916 | 0.216 | 51 | 1.055162052 |
| chr19 | LOC147646 | 33 | 16 | NA | NA | NA | NA | 2.109 | 0.365 | 2.23 | 0.33 | 2.011 | 0.366 | 49 | 0.901793722 |
| chr13 | LINC00366 | 31 | 9 | NA | NA | NA | NA | 1.231 | 0.519 | 1.102 | 0.474 | 1.335 | 0.535 | 40 | 1.211433757 |
| chr05 | SH3PXD2B | 30 | 17 | 44 | 49 | 0.184 | 0.385 | 7.285 | 0.149 | 7.184 | 0.122 | 7.365 | 0.116 | 140 | 1.025194878 |
| chr13 | BRCA2 | 30 | 45 | NA | NA | NA | NA | 6.024 | 0.228 | 6.184 | 0.13 | 5.895 | 0.208 | 75 | 0.953266494 |
| chr15 | RPP25 | 29 | 22 | 14 | NA | 0.059 | NA | 1.783 | 0.495 | 1.604 | 0.56 | 1.926 | 0.384 | 65 | 1.20074813 |
| chr16 | NME3 | 28 | 10 | NA | NA | NA | NA | 2.185 | 0.781 | 2.639 | 0.39 | 1.821 | 0.827 | 38 | 0.690034104 |
| chr19 | FUT2 | 27 | 24 | 50 | 48 | 0.211 | 0.374 | 3.207 | 0.312 | 3.011 | 0.271 | 3.365 | 0.247 | 149 | 1.117568914 |
| chr18 | PARD6G | 27 | 20 | 30 | NA | 0.128 | NA | 6.103 | 0.229 | 5.939 | 0.152 | 6.235 | 0.194 | 77 | 1.04984004 |
| chr17 | PLD6 | 27 | 10 | NA | NA | NA | NA | 4.088 | 0.247 | 4.205 | 0.206 | 3.994 | 0.239 | 37 | 0.949821641 |
| chr12 | RASSF8 | 27 | 3 | NA | NA | NA | NA | 6.251 | 0.226 | 6.108 | 0.101 | 6.366 | 0.233 | 30 | 1.042239686 |
| chr02 | HOXD1 | 27 | 0 | NA | NA | NA | NA | 1.085 | 0.477 | 0.894 | 0.498 | 1.238 | 0.403 | 27 | 1.384787472 |
| chr13 | TNFSF13B | 25 | 9 | 49 | 45 | -0.207 | -0.347 | 4.484 | 0.255 | 4.636 | 0.176 | 4.362 | 0.243 | 128 | 0.940897325 |
| chr10 | FBXL15 | 25 | 6 | NA | NA | NA | NA | 0.44 | 0.516 | 0.544 | 0.418 | 0.357 | 0.573 | 31 | 0.65625 |
| chr21 | LINC00310 | 24 | 2 | 35 | 26 | 0.148 | 0.201 | 3.23 | 0.267 | 3.116 | 0.276 | 3.322 | 0.223 | 87 | 1.066110398 |

*FIG. 20D*

| Location (chr) | Gene | glmnet | glmnet2 | GlmnetF | Glmnet2F | glmnetF. coefficient | Glmnet2F coefficient | Mean | SD | NC-Mean | NC-SD | C-Mean | C-SD | Vote | C/NC Means |
|---|---|---|---|---|---|---|---|---|---|---|---|---|---|---|---|
| chr20 | SDCBP2 | 24 | 0 | NA | NA | NA | NA | 4.638 | 0.219 | 4.707 | 0.173 | 4.582 | 0.236 | 24 | 0.973443807 |
| chr10 | FAM196A | 23 | 2 | 10 | NA | 0.041 | NA | 6.231 | 0.264 | 6.189 | 0.303 | 6.264 | 0.226 | 35 | 1.012118274 |
| chr03 | HTR1F | 22 | 0 | 3 | NA | -0.011 | NA | 1.704 | 0.425 | 1.886 | 0.392 | 1.557 | 0.396 | 25 | 0.825556734 |
| chr02 | FKBP1B | 22 | 0 | NA | NA | NA | NA | 3.809 | 0.242 | 3.917 | 0.216 | 3.722 | 0.228 | 22 | 0.950217003 |
| chr03 | CCDC54 | 20 | 0 | 26 | 5 | -0.109 | -0.04 | 0.097 | 0.497 | 0.325 | 0.535 | -0.087 | 0.378 | 51 | -0.267692308 |
| chr01 | LOC643355 | 20 | 0 | NA | NA | NA | NA | 2.623 | 0.328 | 2.473 | 0.302 | 2.744 | 0.299 | 20 | 1.109583502 |
| chr02 | RAB11FIP5 | 19 | 14 | NA | NA | NA | NA | 5.459 | 0.211 | 5.319 | 0.154 | 5.571 | 0.183 | 33 | 1.047377327 |
| chr09 | FAM206A | 19 | 6 | NA | NA | NA | NA | 1.779 | 0.405 | 1.66 | 0.378 | 1.875 | 0.405 | 25 | 1.129518072 |
| chr18 | OACYLP | 19 | 6 | NA | NA | NA | NA | 3.535 | 0.345 | 3.343 | 0.244 | 3.69 | 0.338 | 25 | 1.103798983 |
| chr17 | UBB | 17 | 0 | 12 | NA | -0.052 | NA | 0.701 | 0.507 | 0.879 | 0.491 | 0.557 | 0.477 | 29 | 0.63367463 |
| chr02 | ANKRD36B | 17 | 0 | 6 | NA | -0.024 | NA | 4.154 | 0.528 | 4.502 | 0.334 | 3.874 | 0.489 | 23 | 0.860506442 |
| chr13 | CKAP2 | 16 | 0 | 57 | 67 | -0.241 | -0.524 | 4.109 | 0.341 | 4.337 | 0.245 | 3.926 | 0.295 | 140 | 0.905234033 |
| chr04 | NEUROG2 | 16 | 0 | 36 | 17 | 0.15 | 0.133 | 0.657 | 0.489 | 0.381 | 0.499 | 0.879 | 0.352 | 69 | 2.307086614 |
| chr16 | RNU6-76 | 16 | 0 | 3 | NA | -0.014 | NA | 4.788 | 0.649 | 5.049 | 0.583 | 4.578 | 0.627 | 19 | 0.906714201 |
| chr06 | ATP6V1G2 | 16 | 0 | NA | NA | NA | NA | 0.373 | 0.445 | 0.437 | 0.372 | 0.322 | 0.494 | 16 | 0.736842105 |
| chr14 | GEMIN2 | 15 | 0 | NA | NA | NA | NA | 3.393 | 0.446 | 3.139 | 0.363 | 3.597 | 0.402 | 15 | 1.14590634 |
| chr17 | RNF126P1 | 14 | 14 | 21 | 9 | 0.088 | 0.071 | 1.906 | 0.445 | 1.752 | 0.483 | 2.03 | 0.372 | 58 | 1.158675799 |
| chr01 | OSCP1 | 14 | 0 | 14 | NA | -0.059 | NA | 4.641 | 0.248 | 4.737 | 0.218 | 4.563 | 0.246 | 28 | 0.963267891 |
| chr08 | CYC1 | 14 | 0 | NA | NA | NA | NA | 1.531 | 0.359 | 1.577 | 0.365 | 1.493 | 0.353 | 14 | 0.946734306 |
| chr05 | PPAP2A | 13 | 0 | 6 | NA | 0.027 | NA | 6.783 | 0.229 | 6.626 | 0.148 | 6.91 | 0.204 | 19 | 1.042861455 |
| chr16 | LOC81691 | 13 | 0 | NA | NA | NA | NA | 4.704 | 0.242 | 4.848 | 0.21 | 4.589 | 0.202 | 13 | 0.946575908 |
| chr04 | LRRC66 | 13 | 0 | NA | NA | NA | NA | 3.327 | 0.473 | 3.04 | 0.394 | 3.558 | 0.401 | 13 | 1.170394737 |
| chr22 | KDELR3 | 12 | 0 | NA | NA | NA | NA | 4.544 | 0.232 | 4.417 | 0.216 | 4.645 | 0.193 | 12 | 1.051618746 |
| chr19 | ZNF44 | 12 | 0 | NA | NA | NA | NA | 4.114 | 0.388 | 3.865 | 0.275 | 4.314 | 0.348 | 12 | 1.116170763 |

FIG. 20E

| Location (chr) | Gene | glmnet | glmnet2 | GlmnetF | Glmnet2F | glmnetF. coefficient | Glmnet2F coefficient | Mean | SD | NC-Mean | NC-SD | C-Mean | C-SD | Vote | C/NC Means |
|---|---|---|---|---|---|---|---|---|---|---|---|---|---|---|---|
| chr04 | FGF2 | 11 | 0 | 38 | 14 | 0.158 | 0.109 | 5.515 | 0.243 | 5.403 | 0.23 | 5.604 | 0.215 | 63 | 1.037201555 |
| chr12 | BTG1 | 11 | 0 | NA | NA | NA | NA | 1.626 | 0.528 | 1.915 | 0.368 | 1.393 | 0.524 | 11 | 0.727415144 |
| chr11 | LAMTOR1 | 11 | 0 | NA | NA | NA | NA | 2.791 | 0.334 | 2.974 | 0.271 | 2.645 | 0.309 | 11 | 0.88937458 |
| chr19 | ODF3L2 | 10 | 0 | 7 | NA | 0.031 | NA | 4.105 | 0.314 | 3.885 | 0.232 | 4.282 | 0.255 | 17 | 1.102187902 |
| chr13 | TMTC4 | 10 | 0 | NA | NA | NA | NA | 6.124 | 0.161 | 6.028 | 0.097 | 6.201 | 0.161 | 10 | 1.028699403 |
| chr06 | HLA-A | 9 | 0 | 13 | NA | -0.054 | NA | 2.728 | 0.41 | 2.912 | 0.41 | 2.58 | 0.349 | 22 | 0.885989011 |
| chr04 | NDNF | 9 | 0 | NA | NA | NA | NA | 3.971 | 0.299 | 3.908 | 0.25 | 4.023 | 0.327 | 9 | 1.029426817 |
| chr11 | TAGLN | 9 | 0 | NA | NA | NA | NA | 3.711 | 0.264 | 3.572 | 0.225 | 3.823 | 0.24 | 9 | 1.070268757 |
| chr12 | TUBA1B | 9 | 0 | NA | NA | NA | NA | 1.882 | 0.42 | 1.951 | 0.452 | 1.827 | 0.387 | 9 | 0.93644285 |
| chr14 | ARF6 | 8 | 0 | NA | NA | NA | NA | 1.998 | 0.453 | 2.17 | 0.506 | 1.86 | 0.353 | 8 | 0.857142857 |
| chr19 | CCDC151 | 8 | 0 | NA | NA | NA | NA | 3.738 | 0.325 | 3.578 | 0.277 | 3.867 | 0.305 | 8 | 1.080771381 |
| chr17 | RASL10B | 7 | 0 | 55 | 36 | 0.23 | 0.281 | 3.87 | 0.281 | 3.688 | 0.232 | 4.016 | 0.227 | 98 | 1.088937093 |
| chr06 | SPDEF | 7 | 0 | 14 | NA | 0.059 | NA | 4.509 | 0.2 | 4.387 | 0.148 | 4.606 | 0.183 | 21 | 1.049920219 |
| chr19 | TBCB | 7 | 0 | 0 | NA | 0 | NA | 4.058 | 0.248 | 4.198 | 0.144 | 3.946 | 0.258 | 7 | 0.939971415 |
| chr04 | DDIT4L | 7 | 0 | NA | NA | NA | NA | 1.209 | 0.535 | 0.961 | 0.477 | 1.408 | 0.498 | 7 | 1.465140479 |
| chr18 | LOC728606 | 7 | 0 | NA | NA | NA | NA | 3.797 | 0.372 | 4.037 | 0.161 | 3.605 | 0.383 | 7 | 0.892989844 |
| chr02 | MEIS1-AS3 | 7 | 0 | NA | NA | NA | NA | 2.437 | 0.332 | 2.494 | 0.36 | 2.391 | 0.304 | 7 | 0.958700882 |
| chr05 | LIFR | 6 | 15 | 24 | 34 | 0.099 | 0.269 | 5.592 | 0.426 | 5.339 | 0.278 | 5.796 | 0.417 | 79 | 1.085596554 |
| chr15 | SYNM | 6 | 0 | 9 | NA | 0.039 | NA | 5.903 | 0.2 | 5.8 | 0.194 | 5.986 | 0.165 | 15 | 1.032068966 |
| chr13 | DIS3 | 6 | 0 | NA | NA | NA | NA | 3.798 | 0.3 | 3.654 | 0.249 | 3.913 | 0.289 | 6 | 1.070881226 |
| chr01 | HMCN1 | 6 | 0 | NA | NA | NA | NA | 7.322 | 0.205 | 7.256 | 0.144 | 7.374 | 0.231 | 6 | 1.016262404 |
| chr10 | LRRTM3 | 6 | 0 | NA | NA | NA | NA | 5.692 | 0.465 | 5.402 | 0.332 | 5.925 | 0.425 | 6 | 1.096815994 |
| chr01 | LAMC2 | 5 | 0 | NA | NA | NA | NA | 5.319 | 0.217 | 5.284 | 0.22 | 5.347 | 0.212 | 5 | 1.011922786 |
| chr07 | LOC728377 | 5 | 0 | NA | NA | NA | NA | 0.443 | 0.531 | 0.328 | 0.532 | 0.536 | 0.517 | 5 | 1.634146341 |

FIG. 20F

| Location (chr) | Gene | glmnet | glmnet2 | GlmnetF | Glmnet2F | glmnetF. coefficient | Glmnet2F coefficient | Mean | SD | NC-Mean | NC-SD | C-Mean | C-SD | Vote | C/NC Means |
|---|---|---|---|---|---|---|---|---|---|---|---|---|---|---|---|
| chr22 | C22orf26 | 4 | 0 | NA | NA | NA | NA | 2.758 | 0.327 | 2.822 | 0.343 | 2.706 | 0.306 | 4 | 0.958894401 |
| chr11 | PLAC1L | 3 | 0 | NA | NA | NA | NA | 1.58 | 0.45 | 1.768 | 0.368 | 1.429 | 0.456 | 3 | 0.808257919 |
| chr02 | VAMP8 | 2 | 0 | 4 | 2 | -0.019 | -0.015 | 2.982 | 0.258 | 3.078 | 0.258 | 2.904 | 0.232 | 8 | 0.943469786 |
| chr06 | GPANK1 | 2 | 0 | NA | NA | NA | NA | 3.182 | 0.317 | 3.331 | 0.258 | 3.063 | 0.311 | 2 | 0.919543681 |
| chr09 | IL33 | 2 | 0 | NA | NA | NA | NA | 3.707 | 0.371 | 3.565 | 0.34 | 3.821 | 0.358 | 2 | 1.071809257 |
| chr16 | IRX3 | 2 | 0 | NA | NA | NA | NA | 1.558 | 0.444 | 1.394 | 0.382 | 1.689 | 0.45 | 2 | 1.211621234 |
| chr11 | NR1H3 | 2 | 0 | NA | NA | NA | NA | 5.405 | 0.188 | 5.479 | 0.157 | 5.345 | 0.191 | 2 | 0.975542982 |
| chr12 | KRT6B | 1 | 0 | 25 | 9 | -0.107 | -0.073 | 1.693 | 0.486 | 1.942 | 0.409 | 1.493 | 0.451 | 35 | 0.768795057 |
| chr11 | LRRC55 | 1 | 10 | NA | NA | NA | NA | 2.448 | 0.436 | 2.255 | 0.392 | 2.603 | 0.41 | 11 | 1.154323725 |
| chr17 | CYB5D1 | 1 | 0 | 7 | NA | -0.029 | NA | 2.085 | 0.373 | 2.242 | 0.348 | 1.958 | 0.346 | 8 | 0.873327386 |
| chr15 | BCL2A1 | 1 | 0 | NA | NA | NA | NA | 4.274 | 0.262 | 4.413 | 0.24 | 4.162 | 0.225 | 1 | 0.943122592 |
| chr01 | LEPR | 1 | 0 | NA | NA | NA | NA | 7.122 | 0.187 | 6.995 | 0.115 | 7.224 | 0.172 | 1 | 1.03273767 |
| chr05 | PCDH1 | 1 | 0 | NA | NA | NA | NA | 5.077 | 0.401 | 4.792 | 0.223 | 5.306 | 0.363 | 1 | 1.107262104 |
| chr02 | PTRHD1 | 1 | 0 | NA | NA | NA | NA | 2.323 | 0.395 | 2.524 | 0.259 | 2.161 | 0.412 | 1 | 0.856180666 |
| chr17 | NXN | 0 | 0 | 48 | 65 | 0.203 | 0.508 | 7.965 | 0.265 | 7.808 | 0.14 | 8.091 | 0.275 | 113 | 1.036244877 |
| chr16 | NOMO3 | 0 | 6 | 39 | 34 | 0.162 | 0.262 | 3.622 | 0.572 | 3.431 | 0.759 | 3.776 | 0.285 | 79 | 1.100553774 |
| chr22 | XBP1 | 0 | 0 | 6 | NA | -0.023 | NA | 2.587 | 0.435 | 2.863 | 0.29 | 2.366 | 0.405 | 6 | 0.826405868 |
| chr12 | MFSD5 | 0 | 5 | NA | NA | NA | NA | 1.941 | 0.472 | 1.75 | 0.546 | 2.094 | 0.338 | 5 | 1.196571429 |
| chr19 | PPP1R15A | 0 | 0 | 4 | NA | -0.015 | NA | 2.975 | 0.335 | 3.078 | 0.254 | 2.892 | 0.37 | 4 | 0.93957115 |
| chr11 | SCGB1D1 | 0 | 1 | NA | NA | NA | NA | 0.893 | 0.507 | 0.988 | 0.539 | 0.817 | 0.471 | 1 | 0.826923077 |
| chr05 | CBY3 | 0 | 0 | NA | NA | NA | NA | 2.979 | 0.359 | 3.146 | 0.275 | 2.845 | 0.363 | 0 | 0.90432295 |
| chr10 | LZTS2 | 0 | 0 | NA | NA | NA | NA | 3.901 | 0.304 | 3.734 | 0.179 | 4.035 | 0.319 | 0 | 1.080610605 |
| chr03 | RBP1 | 0 | 0 | NA | NA | NA | NA | 4.044 | 0.267 | 3.892 | 0.231 | 4.166 | 0.229 | 0 | 1.070400822 |

FIG. 20G

| Location and Gene | glmnet | Location and Gene | glmnet | Location and Gene | glmnet |
|---|---|---|---|---|---|
| chr17~+~18380098~18398259~LGALS9C | 100 | chr01~-~150768683~150780917~CTSK | 59 | chr16~+~74330672~74340186~PSMD7 | 48 |
| chr15~+~75118950~75124136~CPLX3 | 96 | chr09~+~80850990~80881983~CEP78 | 57 | chr14~-~30045686~30396899~PRKD1 | 48 |
| chr07~+~100797685~100804557~AP1S1 | 90 | chr07~+~149535508~149564568~ZNF862 | 57 | chr13~-~35009590~35214822~LINC00457 | 48 |
| chr22~-~23915312~23922495~IGLL1 | 89 | chr02~-~177037923~177053686~HOXD-AS1 | 57 | chr05~-~177419235~177423243~PROP1 | 48 |
| chr17~-~34851598~34891305~MYO19 | 80 | chr11~-~115626050~115630918~LOC283143 | 55 | chr04~-~264463~289944~ZNF732 | 48 |
| chr08~-~92967194~93115454~RUNX1T1 | 77 | chr19~-~9577030~9609279~ZNF560 | 53 | chr01~+~33938231~33961995~ZSCAN20 | 48 |
| chr15~+~22278031~22371088~LOC727924 | 75 | chr19~+~42363987~42375484~RPS19 | 52 | chr09~-~34368906~34376894~KIAA1161 | 47 |
| chr02~+~47055002~47086145~LOC100134259 | 74 | chr16~-~67218281~67224107~EXOC3L1 | 52 | chr19~+~42349085~42356397~DMRTC2 | 46 |
| chr01~+~95699710~95712781~RWDD3 | 73 | chr16~+~58283839~58317734~CCDC113 | 52 | chr13~+~77526623~77532776~IRG1 | 46 |
| chr06~+~37137921~37143204~PIM1 | 72 | chr04~-~15937192~15940363~FGFBP1 | 52 | chr01~-~173152869~173176471~TNFSF4 | 46 |
| chr17~+~34891402~34895150~PIGW | 70 | chr17~+~4634722~4636896~MED11 | 51 | chr01~-~145592604~145610884~POLR3C | 46 |
| chr12~+~9436252~9466684~LOC642846 | 68 | chr12~+~9217772~9220651~A2M-AS1 | 51 | chr06~+~28048481~28057340~ZNF165 | 45 |
| chr01~-~173833038~173837125~GAS5 | 68 | chr19~-~49216254~49222976~MAMSTR | 50 | chr02~+~189156395~189460652~GULP1 | 45 |
| chr15~-~86840064~86860199~LOC727915 | 67 | chr19~-~42177234~42192096~CEACAM7 | 50 | chr12~-~8383644~8395542~FAM86FP | 44 |
| chr06~-~165740775~166075588~PDE10A | 67 | chr13~-~36742344~36788752~SOHLH2 | 50 | chr12~+~53907767~53911392~LOC100652999 | 44 |
| chr09~-~35099888~35103154~STOML2 | 65 | chr12~-~26272958~26278003~BHLHE41 | 50 | chr17~+~44928967~44954437~WNT9B | 43 |
| chr14~+~63671101~63760230~RHOJ | 63 | chr02~-~27359714~27362332~C2orf53 | 50 | chr15~+~47476402~48066420~SEMA6D | 43 |
| chr02~-~88422507~88427650~FABP1 | 63 | chr16~-~48116883~48180681~ABCC12 | 49 | chr09~-~33441151~33447631~AQP3 | 43 |
| chr01~-~79355448~79472495~ELTD1 | 63 | chr14~+~102196773~102198862~LINC00239 | 49 | chr19~+~35606731~35615228~FXYD3 | 42 |
| chr12~-~9208184~9217666~LINC00612 | 61 | chr09~+~98828120~98864194~LOC158435 | 49 | chr07~+~128784711~128809534~TSPAN33 | 42 |
| chr06~-~100367785~100442114~MCHR2 | 60 | chr06~-~27325601~27343153~ZNF204P | 49 | chr06~+~55192266~55267291~GFRAL | 42 |
| chr01~-~162824086~162838605~C1orf110 | 59 | chr18~+~32820993~32838397~ZNF397 | 48 | chr05~-~16451627~16465894~ZNF622 | 42 |

FIG. 21A

| Location and Gene | glmnet | | Location and Gene | glmnet | | Location and Gene | glmnet |
|---|---|---|---|---|---|---|---|
| chr02~+~14772809~14780168~FAM84A | 42 | | chr04~+~140374960~140397069~RAB33B | 37 | | chr08~+~38831667~38846181~HTRA4 | 32 |
| chr15~+~75628373~75632614~COMMD4 | 41 | | chr03~-~183960116~183967313~ALG3 | 37 | | chr07~+~66093867~66108216~KCTD7 | 32 |
| chr11~-~43930838~43942494~LOC100507300 | 41 | | chr20~+~49575350~49578399~MOCS3 | 36 | | chr03~+~52529355~52558511~STAB1 | 32 |
| chr08~-~39308563~39380508~ADAM3A | 41 | | chr19~-~59062932~59066486~CHMP2A | 36 | | chr22~-~20301760~20307628~DGCR6L | 31 |
| chr07~+~5920428~5925994~OCM | 41 | | chr17~+~74075262~74078885~ZACN | 36 | | chr16~-~65318401~65610203~LOC283867 | 31 |
| chr06~-~31132113~31138451~POU5F1 | 41 | | chr14~-~93648540~93651249~MOAP1 | 36 | | chr16~+~23313590~23392620~SCNN1B | 31 |
| chr02~+~45169036~45173216~SIX3 | 41 | | chr12~-~32943679~33049780~PKP2 | 36 | | chr10~+~91137812~91144962~IFIT1B | 31 |
| chr17~-~16453630~16472520~ZNF287 | 40 | | chr08~-~143783669~143808391~LOC100288181 | 36 | | chr09~-~89623365~89657041~LOC440173 | 31 |
| chr04~+~30722029~31148423~PCDH7 | 40 | | chr01~+~38158072~38175391~CDCA8 | 36 | | chr09~-~16409500~16870786~BNC2 | 31 |
| chr02~+~121554866~121750229~GLI2 | 40 | | chr01~+~223566714~223568812~C1orf65 | 36 | | chr07~+~64126510~64171401~ZNF107 | 31 |
| chr01~-~230838271~230850336~AGT | 40 | | chr17~+~75084724~75091068~SEC14L1 | 35 | | chr03~-~2152092~2185925~CNTN4-AS2 | 31 |
| chr21~+~14410486~14490571~ANKRD30BP2 | 39 | | chr15~-~42834719~42841002~LRRC57 | 34 | | chr19~-~43428283~43441330~PSG7 | 30 |
| chr19~+~42212529~42234437~CEACAM5 | 39 | | chr07~-~116916685~116963343~WNT2 | 34 | | chr19~+~45202420~45213986~CEACAM16 | 30 |
| chr08~-~26362195~26371483~PNMA2 | 39 | | chr02~-~213864410~214016333~IKZF2 | 34 | | chr06~-~165693152~165723111~C6orf118 | 30 |
| chr19~+~36203829~36207940~ZBTB32 | 38 | | chr17~+~4981753~4999669~ZFP3 | 33 | | chr05~-~1877540~1882880~IRX4 | 30 |
| chr13~+~25946208~26595420~ATP8A2 | 38 | | chr15~+~90808894~90815443~NGRN | 33 | | chr19~-~44416775~44439411~ZNF45 | 29 |
| chr07~+~94285636~94299006~PEG10 | 38 | | chr15~+~74466086~74469212~ISLR | 33 | | chr17~+~12569206~12670651~MYOCD | 29 |
| chr06~+~35773070~35791852~LHFPL5 | 38 | | chr14~+~105046055~105056183~C14orf180 | 33 | | chr14~+~68086578~68118436~ARG2 | 29 |
| chr01~-~166882440~166944561~ILDR2 | 38 | | chr11~+~57791352~57949038~OR9Q1 | 33 | | chr11~-~58601539~58611997~GLYATL2 | 29 |
| chr11~-~8941622~8954553~C11orf16 | 37 | | chr10~-~42827313~42863493~LOC441666 | 33 | | chr04~+~142142048~142155850~ZNF330 | 29 |
| chr10~+~112631552~112659764~PDCD4 | 37 | | chr07~+~116593952~116599867~ST7-OT4 | 33 | | chr03~-~12194567~12200851~TIMP4 | 29 |
| chr07~+~63773185~63810017~ZNF736 | 37 | | chr11~-~102733463~102745764~MMP12 | 32 | | chr03~+~72200407~72223490~LOC201617 | 29 |

*FIG. 21B*

| Location and Gene | glmnet | | Location and Gene | glmnet | | Location and Gene | glmnet |
|---|---|---|---|---|---|---|---|
| chr03~+~50388296~50391496~CYB561D2 | 29 | | chr02~+~207024317~207027653~EEF1B2 | 27 | | chr22~-~48934711~48943199~LOC284933 | 23 |
| chr01~+~150488232~150490508~LINC00568 | 29 | | chr01~-~44165408~44173012~KDM4A-AS1 | 27 | | chr20~-~61726844~61733671~HAR1B | 23 |
| chr19~-~50655804~50666538~IZUMO2 | 28 | | chr09~+~89763558~89774641~C9orf170 | 26 | | chr20~+~1184097~1188918~C20orf202 | 23 |
| chr19~+~21106058~21133503~ZNF85 | 28 | | chr07~-~130126897~130131013~MESTIT1 | 26 | | chr19~-~5678432~5680911~C19orf70 | 23 |
| chr17~-~67074846~67138015~ABCA6 | 28 | | chr07~+~140396480~140406446~NDUFB2 | 26 | | chr17~-~15879874~15903006~ZSWIM7 | 23 |
| chr17~+~16690205~16707819~USP32P1 | 28 | | chr06~-~5998232~6007633~NRN1 | 26 | | chr16~-~77316024~77469011~ADAMTS18 | 23 |
| chr15~+~64443915~64449680~SNX22 | 28 | | chr03~-~38492517~38496311~ACVR2B-AS1 | 26 | | chr12~-~71031852~71314584~PTPRR | 23 |
| chr14~-~73945188~74025651~HEATR4 | 28 | | chr16~+~432240~442960~LOC100134368 | 25 | | chr12~-~52862299~52867569~KRT6C | 23 |
| chr14~+~42076763~42373752~LRFN5 | 28 | | chr16~+~1031807~1036979~SOX8 | 25 | | chr09~-~41958801~42019584~KGFLP2 | 23 |
| chr06~+~29973747~29977733~HLA-J | 28 | | chr10~+~23983674~24836772~KIAA1217 | 25 | | chr08~-~94146323~94179079~C8orf87 | 23 |
| chr01~+~231473681~231490769~SPRTN | 28 | | chr08~-~97154557~97173020~GDF6 | 25 | | chr07~-~142568959~142583490~TRPV6 | 23 |
| chr22~-~22890122~22901696~PRAME | 27 | | chr05~-~33527286~33892124~ADAMTS12 | 25 | | chr06~-~170188885~170198921~LINC00242 | 23 |
| chr22~+~42896584~42908566~SERHL | 27 | | chr05~+~128301209~128369335~SLC27A6 | 25 | | chr05~+~178322915~178360210~ZFP2 | 23 |
| chr20~+~55204357~55214338~TFAP2C | 27 | | chr01~-~25548766~25559013~SYF2 | 25 | | chr05~+~15500304~15939900~FBXL7 | 23 |
| chr20~+~43343884~43356452~WISP2 | 27 | | chr20~+~62665696~62671315~LINC00176 | 24 | | chr05~+~140345746~140391929~PCDHAC2 | 23 |
| chr19~+~37959981~37976242~ZNF570 | 27 | | chr17~+~4487275~4511614~SMTNL2 | 24 | | chr02~-~208473838~208489973~METTL21A | 23 |
| chr15~+~22546564~22570831~REREP3 | 27 | | chr14~+~74003927~74010498~ACOT1 | 24 | | chr02~+~240684553~240722356~LOC150935 | 23 |
| chr14~-~68117866~68141602~VTI1B | 27 | | chr13~+~108870762~108886603~ABHD13 | 24 | | chr02~+~120189445~120196096~TMEM37 | 23 |
| chr10~+~87337487~87366972~GRID1-AS1 | 27 | | chr09~+~38392660~38398662~ALDH1B1 | 24 | | chr01~+~109756514~109780804~SARS | 23 |
| chr09~-~96938851~96966848~MIRLET7DHG | 27 | | chr03~-~139279022~139396885~NMNAT3 | 24 | | chr19~-~23157684~23186010~ZNF728 | 22 |
| chr06~+~88032305~88052043~SMIM8 | 27 | | chr02~-~153508106~153573975~PRPF40A | 24 | | chr17~-~18414575~18424566~USP32P2 | 22 |
| chr03~+~38537762~38567796~EXOG | 27 | | chr01~+~75594118~75627218~LHX8 | 24 | | chr17~+~30367354~30369851~SH3GL1P1 | 22 |

*FIG. 21C*

| Location and Gene | glmnet | Location and Gene | glmnet | Location and Gene | glmnet |
|---|---|---|---|---|---|
| chr16~+~14014013~14046205~ERCC4 | 22 | chr20~-~25121433~25129426~LOC284798 | 20 | chr09~-~34521039~34523037~ENHO | 19 |
| chr15~-~93160678~93199031~FAM174B | 22 | chr20~+~23345020~23353683~GZF1 | 20 | chr09~+~95571892~95600739~ANKRD19P | 19 |
| chr12~+~108956293~108963160~ISCU | 22 | chr17~+~77071018~77084685~ENGASE | 20 | chr07~+~1609708~1629261~PSMG3-AS1 | 19 |
| chr08~+~24771273~24776606~NEFM | 22 | chr15~-~52401821~52404972~BCL2L10 | 20 | chr06~-~76017799~76203496~FILIP1 | 19 |
| chr06~-~55921387~56112378~COL21A1 | 22 | chr15~+~75941347~75950968~SNX33 | 20 | chr06~+~31913720~31919861~CFB | 19 |
| chr06~+~96463844~96663488~FUT9 | 22 | chr14~-~77940737~77965210~ISM2 | 20 | chr02~+~105858199~105859924~GPR45 | 19 |
| chr04~-~187454808~187476537~MTNR1A | 22 | chr13~+~49822046~49867622~CDADC1 | 20 | chr01~-~111489811~111506566~LRIF1 | 19 |
| chr02~+~172864803~172945587~METAP1D | 22 | chr13~+~22245214~22278640~FGF9 | 20 | chr01~+~84944919~84964033~RPF1 | 19 |
| chr21~-~10906742~10990920~TPTE | 21 | chr11~-~63228875~63258680~HRASLS5 | 20 | chr01~+~230883129~230937749~CAPN9 | 19 |
| chr15~+~51973549~52013223~SCG3 | 21 | chr06~-~117113247~117150198~GPRC6A | 20 | chr20~+~55926144~55953519~RAE1 | 18 |
| chr10~-~38238794~38265453~ZNF25 | 21 | chr06~+~119215240~119230335~ASF1A | 20 | chr17~-~10395626~10421859~MYH1 | 18 |
| chr09~-~139956578~139965028~SAPCD2 | 21 | chr05~-~151771101~151784840~NMUR2 | 20 | chr14~-~26915088~27066960~NOVA1 | 18 |
| chr07~+~27282163~27286192~EVX1 | 21 | chr04~+~41983712~41988484~DCAF4L1 | 20 | chr09~-~131707808~131710012~DOLK | 18 |
| chr05~+~177433966~177476088~FAM153C | 21 | chr02~+~56411257~56613309~CCDC85A | 20 | chr09~+~123555774~123561009~LOC100288842 | 18 |
| chr05~+~140306301~140391929~PCDHAC1 | 21 | chr01~-~232533711~232651243~SIPA1L2 | 20 | chr08~-~93725189~93798288~FLJ46284 | 18 |
| chr03~-~151153777~151176497~IGSF10 | 21 | chr01~-~190066796~190446759~FAM5C | 20 | chr07~+~137638093~137642712~LOC100130880 | 18 |
| chr03~+~89156673~89531284~EPHA3 | 21 | chr01~-~185087217~185126230~TRMT1L | 20 | chr05~-~158875563~158893284~LOC285627 | 18 |
| chr03~+~51989329~51991520~GPR62 | 21 | chr20~+~56136136~56141513~PCK1 | 19 | chr05~+~153825516~153840613~SAP30L | 18 |
| chr02~+~210288770~210598834~MAP2 | 21 | chr19~-~2233154~2236328~PLEKHJ1 | 19 | chr05~+~131993864~131996801~IL13 | 18 |
| chr01~+~218066241~218094146~LINC00210 | 21 | chr17~+~72199794~72206019~RPL38 | 19 | chr01~-~39987951~40025370~PPIEL | 18 |
| chr01~+~201857796~201861715~SHISA4 | 21 | chr12~+~56552044~56555366~MYL6 | 19 | chr01~-~241792166~241799232~CHML | 18 |
| chr01~+~161136180~161141010~PPOX | 21 | chr10~+~51827683~51893269~FAM21A | 19 | chr01~+~55446464~55457966~TMEM61 | 18 |

FIG. 21D

| Location and Gene | glmnet | | Location and Gene | glmnet | | Location and Gene | glmnet |
|---|---|---|---|---|---|---|---|
| chr01~+~145096406~145116997~SEC22B | 18 | | chr19~+~52800425~52829174~ZNF480 | 16 | | chr02~+~108443387~108509000~RGPD4 | 15 |
| chr22~-~21827286~21871780~PI4KAP2 | 17 | | chr17~+~80009762~80015346~GPS1 | 16 | | chr01~+~22970117~22974603~C1QC | 15 |
| chr19~-~9868150~9879410~ZNF846 | 17 | | chr17~+~16593638~16678311~CCDC144A | 16 | | chr01~+~155036212~155042029~EFNA4 | 15 |
| chr19~-~35978225~35981433~KRTDAP | 17 | | chr16~+~1832932~1839192~NUBP2 | 16 | | chr21~+~29094697~29123552~LINC00113 | 14 |
| chr17~+~7761063~7765600~CYB5D1 | 17 | | chr13~-~111516333~111522655~LINC00346 | 16 | | chr20~+~31781410~31798268~BPIFA4P | 14 |
| chr17~+~49242795~49249105~NME2 | 17 | | chr12~+~56211805~56214959~ORMDL2 | 16 | | chr19~-~58433251~58446740~ZNF418 | 14 |
| chr17~+~44270938~44274089~KANSL1-AS1 | 17 | | chr10~+~51837885~51893269~FAM21B | 16 | | chr19~+~46498718~46521874~CCDC61 | 14 |
| chr17~+~38024454~38034149~ZPBP2 | 17 | | chr06~+~94416800~94486199~TSG1 | 16 | | chr12~-~120759913~120765592~PLA2G1B | 14 |
| chr16~+~2286467~2288712~DNASE1L2 | 17 | | chr05~-~160715435~160975130~GABRB2 | 16 | | chr11~+~49580079~49831969~LOC440040 | 14 |
| chr13~-~36342788~36705514~DCLK1 | 17 | | chr04~+~53656160~53681631~LOC152578 | 16 | | chr11~+~34127110~34168458~NAT10 | 14 |
| chr11~+~22359666~22401046~SLC17A6 | 17 | | chr04~+~17616272~17626160~MED28 | 16 | | chr09~-~98868942~98878693~LOC158434 | 14 |
| chr10~-~10976902~10994126~LINC00710 | 17 | | chr04~+~123747862~123819390~FGF2 | 16 | | chr09~-~139088095~139096955~LHX3 | 14 |
| chr10~+~14920781~14946304~SUV39H2 | 17 | | chr03~+~183967444~184010819~ECE2 | 16 | | chr08~-~131792546~132052835~ADCY8 | 14 |
| chr09~-~6011018~6015640~RANBP6 | 17 | | chr19~-~46969747~46974820~PNMAL1 | 15 | | chr07~+~419390~422845~LOC442497 | 14 |
| chr08~+~70378858~70573147~SULF1 | 17 | | chr12~-~69068150~69080639~LOC100507250 | 15 | | chr06~-~170591293~170599697~DLL1 | 14 |
| chr08~+~136246373~136311962~LOC286094 | 17 | | chr12~-~104343980~104350993~C12orf73 | 15 | | chr04~-~104510624~104640973~TACR3 | 14 |
| chr07~+~94536948~94925727~PPP1R9A | 17 | | chr08~-~38268655~38326352~FGFR1 | 15 | | chr02~+~63815742~63834330~MDH1 | 14 |
| chr04~-~76404246~76439640~RCHY1 | 17 | | chr05~-~175386533~175395545~THOC3 | 15 | | chr01~-~144851423~145076186~PDE4DIP | 14 |
| chr04~+~166794409~167025609~TLL1 | 17 | | chr05~-~160358785~160365633~LOC285629 | 15 | | chr22~-~23732791~23744799~ZDHHC8P1 | 13 |
| chr01~+~28918711~28921088~RAB42 | 17 | | chr04~+~6202459~6235663~LOC285484 | 15 | | chr21~-~28659821~29283529~MIR5009 | 13 |
| chr01~+~12916940~12921764~PRAMEF2 | 17 | | chr03~+~125688027~125702296~ROPN1B | 15 | | chr17~-~39576808~39580822~KRT37 | 13 |
| chr22~-~51017386~51021428~CHKB | 16 | | chr02~+~131100488~131104197~IMP4 | 15 | | chr12~+~52301201~52317145~ACVRL1 | 13 |

FIG. 21E

| Location and Gene | glmnet | | Location and Gene | glmnet | | Location and Gene | glmnet |
|---|---|---|---|---|---|---|---|
| chr11~-~73583712~73587890~COA4 | 13 | | chr03~+~238278~451097~CHL1 | 12 | | chr04~+~144434615~144478642~SMARCA5 | 11 |
| chr11~-~116649275~116658739~ZNF259 | 13 | | chr03~+~126707436~126756235~PLXNA1 | 12 | | chr02~+~198318230~198339851~COQ10B | 11 |
| chr08~-~95261484~95274547~GEM | 13 | | chr02~+~264868~278282~ACP1 | 12 | | chr02~+~193614570~193641625~PCGEM1 | 11 |
| chr08~+~74903563~74941307~LY96 | 13 | | chr01~-~89646830~89664633~GBP4 | 12 | | chr02~+~131513076~131525707~AMER3 | 11 |
| chr05~-~141971742~142077635~FGF1 | 13 | | chr01~-~152321212~152332482~FLG2 | 12 | | chr01~-~54497348~54519111~TMEM59 | 11 |
| chr04~-~177134825~177190373~ASB5 | 13 | | chr01~+~861120~879961~SAMD11 | 12 | | chr01~-~156374054~156399184~C1orf61 | 11 |
| chr04~+~16228285~16259810~TAPT1-AS1 | 13 | | chr22~+~39828164~39833133~LOC100506472 | 11 | | chr22~+~21356210~21364663~THAP7-AS1 | 10 |
| chr03~-~190023489~190040235~CLDN1 | 13 | | chr15~-~71123888~71146498~LARP6 | 11 | | chr21~-~40777769~40816128~LCA5L | 10 |
| chr02~+~24397971~24414567~FAM228A | 13 | | chr15~+~86685241~87572283~AGBL1 | 11 | | chr21~-~11020841~11098925~BAGE5 | 10 |
| chr01~-~35447126~35450948~ZMYM6NB | 13 | | chr14~-~36942493~36982990~SFTA3 | 11 | | chr21~-~11020841~11098925~BAGE4 | 10 |
| chr22~-~23701792~23724313~CES5AP1 | 12 | | chr14~+~90528107~90652195~KCNK13 | 11 | | chr21~-~11020841~11098925~BAGE3 | 10 |
| chr20~+~44462469~44471914~SNX21 | 12 | | chr13~+~31506833~31549153~TEX26 | 11 | | chr21~+~42792519~42831141~MX1 | 10 |
| chr19~-~58944180~58951589~ZNF132 | 12 | | chr10~-~96092988~96122683~NOC3L | 11 | | chr19~-~11487880~11495018~EPOR | 10 |
| chr19~-~53641956~53662322~ZNF347 | 12 | | chr10~+~110930414~110999490~RNU6-53 | 11 | | chr19~+~39687603~39692522~NCCRP1 | 10 |
| chr19~-~46442770~46476657~NOVA2 | 12 | | chr09~-~19376253~19380235~RPS6 | 11 | | chr17~-~58160926~58165828~LOC645638 | 10 |
| chr19~-~22148896~22193745~ZNF208 | 12 | | chr08~-~146102335~146126846~ZNF250 | 11 | | chr17~-~43189007~43209891~PLCD3 | 10 |
| chr19~+~4247110~4269085~CCDC94 | 12 | | chr08~+~99956630~99964326~OSR2 | 11 | | chr15~+~88795960~88814297~NTRK3-AS1 | 10 |
| chr19~+~30863327~31048965~ZNF536 | 12 | | chr07~-~53723201~53879624~FLJ45974 | 11 | | chr13~-~107820878~108519460~FAM155A | 10 |
| chr17~+~12453284~12540504~LINC00670 | 12 | | chr07~-~33134409~33149002~RP9 | 11 | | chr09~+~138073454~138079152~LOC401557 | 10 |
| chr16~-~31142753~31147151~PRSS8 | 12 | | chr06~-~169615874~169654137~THBS2 | 11 | | chr08~+~39442086~39587583~ADAM18 | 10 |
| chr12~-~32899477~32908887~YARS2 | 12 | | chr04~+~188916924~188926199~ZFP42 | 11 | | chr08~+~15397595~15624158~TUSC3 | 10 |
| chr09~+~1050345~1057554~DMRT2 | 12 | | chr04~+~164415672~164441691~TMA16 | 11 | | chr08~+~144718182~144735900~ZNF623 | 10 |

FIG. 21F

| Location and Gene | glmnet | Location and Gene | glmnet | Location and Gene | glmnet |
|---|---|---|---|---|---|
| chr06~-~35465650~35480647~TULP1 | 10 | chr08~-~101145587~101158099~FBXO43 | 9 | chr01~-~27992571~27998724~IFI6 | 8 |
| chr06~-~31105310~31107127~PSORS1C2 | 10 | chr07~-~45022626~45026259~SNHG15 | 9 | chr01~+~209757044~209787284~CAMK1G | 8 |
| chr06~+~158422138~158423415~SYNJ2-IT1 | 10 | chr05~-~150070351~150080669~RBM22 | 9 | chr22~-~24385937~24401899~GSTTP2 | 7 |
| chr05~-~178537851~178772431~ADAMTS2 | 10 | chr05~+~180257956~180262726~LINC00847 | 9 | chr19~-~9405985~9415795~ZNF699 | 7 |
| chr05~+~31532372~31555165~C5orf22 | 10 | chr05~+~140247830~140391929~PCDHA11 | 9 | chr19~-~43225793~43244668~PSG3 | 7 |
| chr03~-~126061477~126076236~KLF15 | 10 | chr21~-~11057795~11098937~BAGE | 8 | chr19~-~38229202~38270230~ZNF573 | 7 |
| chr03~+~158288952~158324249~MLF1 | 10 | chr19~-~12428303~12444534~ZNF563 | 8 | chr18~+~904943~912173~ADCYAP1 | 7 |
| chr01~-~24446260~24469775~IL22RA1 | 10 | chr19~+~15939756~15947131~UCA1 | 8 | chr16~-~30125425~30134630~MAPK3 | 7 |
| chr01~+~24526729~24538180~LOC284632 | 10 | chr13~-~79894099~79979923~RBM26 | 8 | chr15~-~78206558~78219188~LOC645752 | 7 |
| chr01~+~233086369~233114219~NTPCR | 10 | chr13~+~27844463~27847827~RASL11A | 8 | chr10~+~50817140~50873150~CHAT | 7 |
| chr21~-~41990432~42002693~DSCAM-IT1 | 9 | chr10~-~118423206~118429481~C10orf82 | 8 | chr10~+~106028630~106059176~GSTO2 | 7 |
| chr21~-~35275756~35288158~ATP5O | 9 | chr08~-~39601254~39695779~ADAM2 | 8 | chr08~-~38368351~38386180~C8orf86 | 7 |
| chr19~-~51515999~51523431~KLK10 | 9 | chr08~+~144295067~144299044~GPIHBP1 | 8 | chr07~-~56078743~56119268~PSPH | 7 |
| chr19~-~47549166~47551882~TMEM160 | 9 | chr07~-~148766732~148787869~ZNF786 | 8 | chr05~+~140261853~140391929~PCDHA13 | 7 |
| chr19~-~1473199~1479228~C19orf25 | 9 | chr06~-~42174538~42185633~MRPS10 | 8 | chr04~-~68603098~68621804~GNRHR | 7 |
| chr17~-~56282796~56296966~MKS1 | 9 | chr06~-~117073359~117086886~FAM162B | 8 | chr02~-~25383721~25391559~POMC | 7 |
| chr17~-~41102542~41116515~PTGES3L-AARSD1 | 9 | chr06~-~10428017~10435055~LINC00518 | 8 | chr02~-~202484906~202508252~TMEM237 | 7 |
| chr17~+~77019015~77045870~C1QTNF1 | 9 | chr06~+~116359893~116361107~TPI1P3 | 8 | chr02~-~177494308~177502302~LOC375295 | 7 |
| chr16~-~20744988~20753199~THUMPD1 | 9 | chr06~+~10747994~10757214~TMEM14B | 8 | chr02~+~101869344~101886778~CNOT11 | 7 |
| chr14~-~105403590~105444694~AHNAK2 | 9 | chr05~-~138727634~138730885~PROB1 | 8 | chr01~-~151810338~151813033~C2CD4D | 7 |
| chr14~+~96343108~96391908~LINC00617 | 9 | chr02~-~242434121~242448987~STK25 | 8 | chr01~-~100652477~100715409~DBT | 7 |
| chr11~-~124636393~124670299~MSANTD2 | 9 | chr01~-~32117847~32169768~COL16A1 | 8 | chr01~+~71512188~71532865~ZRANB2-AS1 | 7 |

FIG. 21G

| Location and Gene | glmnet | Location and Gene | glmnet | Location and Gene | glmnet |
|---|---|---|---|---|---|
| chr01~+~39957317~39995541~BMP8A | 7 | chr04~-~122745483~122791652~BBS7 | 6 | chr04~-~181985242~182080302~LINC00290 | 5 |
| chr22~-~37966252~37976024~LGALS2 | 6 | chr02~+~205410515~206484886~PARD3B | 6 | chr03~+~12045861~12233532~SYN2 | 5 |
| chr22~+~38219388~38221502~GALR3 | 6 | chr01~+~1447522~1470067~ATAD3A | 6 | chr02~-~73989324~74007284~DUSP11 | 5 |
| chr20~+~44509847~44513905~ZSWIM1 | 6 | chr01~+~111889194~111895639~PIFO | 6 | chr02~-~239840997~239847965~FLJ43879 | 5 |
| chr19~-~11616730~11639987~ECSIT | 6 | chr20~-~740723~749228~SLC52A3 | 5 | chr20~-~11247306~11254031~LOC339593 | 4 |
| chr19~+~40697650~40721482~MAP3K10 | 6 | chr19~-~55912649~55919325~UBE2S | 5 | chr19~-~14583277~14586174~PTGER1 | 4 |
| chr19~+~12863406~12869271~BEST2 | 6 | chr17~-~53796987~53809482~TMEM100 | 5 | chr19~+~53898396~53915262~ZNF765 | 4 |
| chr17~-~10346607~10372876~MYH4 | 6 | chr16~-~64980682~65155919~CDH11 | 5 | chr17~-~62850487~62914903~LRRC37A3 | 4 |
| chr16~-~4307186~4323001~TFAP4 | 6 | chr16~+~66613350~66622177~CMTM2 | 5 | chr17~+~45286427~45301045~MYL4 | 4 |
| chr14~-~71050956~71067384~MED6 | 6 | chr15~-~21932513~21940739~LOC646214 | 5 | chr16~+~2022063~2028751~TBL3 | 4 |
| chr12~-~44902057~45307711~NELL2 | 6 | chr12~-~58019677~58027022~B4GALNT1 | 5 | chr15~-~101811213~101817700~VIMP | 4 |
| chr12~-~25146364~25150373~C12orf77 | 6 | chr12~-~57422300~57444549~MYO1A | 5 | chr13~+~31480311~31499709~MEDAG | 4 |
| chr11~-~4619901~4629489~TRIM68 | 6 | chr12~-~52840434~52845910~KRT6B | 5 | chr12~-~70910631~71031220~PTPRB | 4 |
| chr09~+~87283465~87638505~NTRK2 | 6 | chr12~+~97301000~97347469~NEDD1 | 5 | chr12~+~52604713~52617597~LINC00592 | 4 |
| chr08~-~38020838~38034248~LSM1 | 6 | chr12~+~9392598~9395645~LOC100499405 | 5 | chr12~+~25348149~25357949~LYRM5 | 4 |
| chr08~-~23699433~23712320~STC1 | 6 | chr12~+~85674035~85695561~ALX1 | 5 | chr12~+~10457049~10469850~KLRD1 | 4 |
| chr07~-~57233376~57247863~GUSBP10 | 6 | chr11~-~3659735~3663546~ART5 | 5 | chr10~+~50887683~50916956~C10orf53 | 4 |
| chr07~-~2273925~2281833~FTSJ2 | 6 | chr11~+~60609428~60618561~CCDC86 | 5 | chr08~-~21971931~21988565~HR | 4 |
| chr07~+~142829173~142836834~PIP | 6 | chr09~-~132374503~132383055~C9orf50 | 5 | chr07~-~83587658~83824217~SEMA3A | 4 |
| chr07~+~123565285~123611461~SPAM1 | 6 | chr09~+~140657473~140659224~FLJ40292 | 5 | chr06~-~114257319~114292359~HDAC2 | 4 |
| chr05~+~140254930~140391929~PCDHA12 | 6 | chr07~-~45951843~45960871~IGFBP3 | 5 | chr06~+~54173202~54254950~TINAG | 4 |
| chr04~-~83274466~83295149~HNRNPD | 6 | chr05~+~72416387~72427644~TMEM171 | 5 | chr06~+~100441913~100524295~LOC728012 | 4 |

FIG. 21H

| Location and Gene | glmnet | | Location and Gene | glmnet | | Location and Gene | glmnet |
|---|---|---|---|---|---|---|---|
| chr05~-~175810939~175815763~NOP16 | 4 | | chr01~-~53692563~53704282~MAGOH | 3 | | chr05~+~140174443~140391929~PCDHA2 | 2 |
| chr05~+~149380168~149432706~HMGXB3 | 4 | | chr01~-~228391206~228401365~C1orf145 | 3 | | chr03~-~49758931~49761384~GMPPB | 2 |
| chr02~-~218148745~218621316~DIRC3 | 4 | | chr01~+~210406194~210416440~SERTAD4 | 3 | | chr03~+~29322802~30051886~RBMS3 | 2 |
| chr02~+~27651472~27665124~NRBP1 | 4 | | chr22~-~46316247~46373008~WNT7B | 2 | | chr03~+~114012832~114029135~TIGIT | 2 |
| chr01~-~19592475~19600568~AKR7L | 4 | | chr20~+~61669362~61685215~LOC100144597 | 2 | | chr02~+~120436742~120439694~TMEM177 | 2 |
| chr01~+~47264669~47285021~CYP4B1 | 4 | | chr20~+~44746905~44758384~CD40 | 2 | | chr01~-~228581376~228594517~TRIM11 | 2 |
| chr19~-~44830705~44860856~ZFP112 | 3 | | chr19~-~52617652~52643191~ZNF616 | 2 | | chr01~-~156213111~156217908~PAQR6 | 2 |
| chr19~-~23835707~23870017~ZNF675 | 3 | | chr19~+~18043823~18054794~CCDC124 | 2 | | chr01~+~53704281~53708455~LOC100507564 | 2 |
| chr19~+~48325098~48346586~CRX | 3 | | chr18~+~14748238~14852737~ANKRD30B | 2 | | chr01~+~43824625~43828873~CDC20 | 2 |
| chr17~-~47007458~47022154~SNF8 | 3 | | chr17~+~43583248~43597889~LRRC37A4P | 2 | | chr01~+~24018268~24022915~RPL11 | 2 |
| chr16~-~75572014~75590184~TMEM231 | 3 | | chr15~-~85198359~85201802~NMB | 2 | | chr19~-~53268747~53290034~ZNF600 | 1 |
| chr14~+~21214098~21216539~EDDM3A | 3 | | chr13~-~36048405~36515382~MIR548F5 | 2 | | chr19~-~51446558~51456344~KLK5 | 1 |
| chr12~+~7917811~7926717~NANOGNB | 3 | | chr12~-~57106210~57119326~NACA | 2 | | chr19~-~43370612~43383871~PSG1 | 1 |
| chr09~+~35749276~35753264~RGP1 | 3 | | chr12~+~123565930~123569291~LOC100507091 | 2 | | chr18~+~12308256~12326568~TUBB6 | 1 |
| chr07~-~55247442~55256642~EGFR-AS1 | 3 | | chr11~-~106544737~106889171~GUCY1A2 | 2 | | chr17~-~70399462~70588943~LINC00673 | 1 |
| chr07~-~34386123~34873943~NPSR1-AS1 | 3 | | chr09~-~13406378~13431328~FLJ41200 | 2 | | chr17~+~43697711~43715329~MGC57346 | 1 |
| chr07~+~77976558~77988770~RPL13AP17 | 3 | | chr08~-~12579405~12612992~LONRF1 | 2 | | chr16~-~88744089~88752882~SNAI3 | 1 |
| chr07~+~57509882~57533265~ZNF716 | 3 | | chr07~+~63688851~63727309~ZNF679 | 2 | | chr16~-~684428~686347~C16orf13 | 1 |
| chr05~+~140235633~140391929~PCDHA10 | 3 | | chr07~+~44240577~44253893~YKT6 | 2 | | chr12~-~48103517~48119355~ENDOU | 1 |
| chr05~+~140165875~140391929~PCDHA1 | 3 | | chr06~-~123537483~123958238~TRDN | 2 | | chr12~-~108983621~108991894~TMEM119 | 1 |
| chr04~-~186421814~186456712~PDLIM3 | 3 | | chr05~+~36876860~37065921~NIPBL | 2 | | chr11~-~73711325~73720282~UCP3 | 1 |
| chr04~-~107842958~107957453~DKK2 | 3 | | chr05~+~140213968~140391929~PCDHA7 | 2 | | chr09~+~35860270~35865515~FP588 | 1 |

FIG. 21I

| Location and Gene | glmnet | Location and Gene | glmnet | Location and Gene | glmnet |
|---|---|---|---|---|---|
| chr09~+~136223420~136228040~SURF2 | 1 | | | | |
| chr08~-~16850333~16859674~FGF20 | 1 | | | | |
| chr07~+~55086724~55275031~EGFR | 1 | | | | |
| chr07~+~39773166~39834222~LINC00265 | 1 | | | | |
| chr06~-~55620237~55740375~BMP5 | 1 | | | | |
| chr06~-~105605774~105627858~POPDC3 | 1 | | | | |
| chr05~+~140227356~140391929~PCDHA9 | 1 | | | | |
| chr05~+~140220906~140391929~PCDHA8 | 1 | | | | |
| chr05~+~140201360~140391929~PCDHA5 | 1 | | | | |
| chr04~+~178649910~178911904~LOC285501 | 1 | | | | |
| chr03~-~57302378~57326710~ASB14 | 1 | | | | |
| chr03~-~121350245~121379791~HCLS1 | 1 | | | | |
| chr02~-~110841446~110874143~MALL | 1 | | | | |
| chr01~-~2572806~2706230~TTC34 | 1 | | | | |
| chr01~-~101092605~101112560~LOC100128787 | 1 | | | | |
| chr01~+~32671235~32674288~IQCC | 1 | | | | |
| | | | | | |
| | | | | | |
| | | | | | |
| | | | | | |
| | | | | | |
| | | | | | |

FIG. 21J

| chr | Gene | glmnet | glmnet2 | glmnetF | glmnet2F | glmnetF.coef | glmnet2F.coef | mean | sd | nonCancer.mean | nonCancer.sd | Cancer.mean | Cancer.sd |
|---|---|---|---|---|---|---|---|---|---|---|---|---|---|
| chr16 | ABCC12 | 11 | 0 | 11 | NA | 0.014 | NA | 4.564 | 0.371 | 4.297 | 0.147 | 4.831 | 0.332 |
| chr03 | ADAMTS9-AS2 | 2 | 0 | 1 | NA | 0.002 | NA | 6.294 | 0.629 | 5.828 | 0.332 | 6.76 | 0.496 |
| chr09 | BNC2 | 12 | 0 | 12 | NA | 0.015 | NA | 6.979 | 0.487 | 6.621 | 0.234 | 7.338 | 0.401 |
| chr14 | C14orf64 | 45 | 0 | 45 | NA | 0.057 | NA | 3.355 | 0.517 | 2.976 | 0.273 | 3.733 | 0.418 |
| chr15 | C15orf53 | 7 | 8 | 7 | 8 | -0.009 | -0.04 | 1.791 | 0.456 | 2.076 | 0.289 | 1.505 | 0.412 |
| chr17 | C17orf51 | 2 | 0 | 2 | NA | 0.003 | NA | 4.211 | 0.396 | 3.962 | 0.339 | 4.459 | 0.274 |
| chr01 | CAMK1G | 7 | 0 | 7 | NA | 0.009 | NA | 4.383 | 0.2 | 4.257 | 0.153 | 4.508 | 0.159 |
| chr07 | CCDC129 | 5 | 0 | 5 | NA | 0.006 | NA | 4.33 | 0.481 | 3.984 | 0.248 | 4.675 | 0.403 |
| chr15 | CERS3 | 67 | 57 | 67 | 57 | 0.085 | 0.287 | 5.702 | 0.425 | 5.403 | 0.347 | 6 | 0.25 |
| chr13 | DCLK1 | 15 | 0 | 15 | NA | 0.019 | NA | 5.861 | 0.611 | 5.404 | 0.246 | 6.317 | 0.518 |
| chr05 | FBXL7 | 31 | 0 | 30 | NA | 0.039 | NA | 6.493 | 0.71 | 5.965 | 0.413 | 7.022 | 0.528 |
| chr13 | FGF9 | 5 | 0 | 5 | NA | 0.007 | NA | 3.799 | 0.296 | 3.598 | 0.187 | 4.001 | 0.244 |
| chr06 | FILIP1 | 16 | 0 | 16 | NA | 0.02 | NA | 5.357 | 0.371 | 5.091 | 0.247 | 5.622 | 0.271 |
| chr15 | GABRA5 | 1 | 0 | 1 | NA | 0.002 | NA | 3.815 | 0.538 | 3.43 | 0.23 | 4.201 | 0.478 |
| chr15 | GABRG3 | 33 | 0 | 33 | NA | 0.042 | NA | 6.227 | 0.599 | 5.784 | 0.276 | 6.669 | 0.499 |
| chr16 | GP2 | 56 | 42 | 56 | 42 | 0.071 | 0.212 | 1.791 | 0.646 | 1.322 | 0.31 | 2.259 | 0.546 |
| chr19 | HKR1 | 17 | 0 | 17 | NA | 0.021 | NA | 4.049 | 0.407 | 3.759 | 0.228 | 4.339 | 0.334 |
| chr07 | HOXA4 | 50 | 42 | 50 | 42 | -0.063 | -0.213 | 1.054 | 0.548 | 1.4 | 0.331 | 0.708 | 0.503 |
| NA | Intercep | NA | NA | NA | NA | 0.05 | 0.105 | NA | NA | NA | NA | NA | NA |
| chr15 | ISLR2 | 4 | 11 | 4 | 11 | 0.005 | 0.053 | 2.223 | 0.431 | 1.958 | 0.301 | 2.487 | 0.377 |
| chr09 | KLF9 | 0 | 5 | NA | 5 | NA | -0.024 | 5.671 | 0.255 | 5.833 | 0.13 | 5.51 | 0.247 |
| chr13 | LINC00457 | 100 | 100 | 100 | 100 | 0.127 | 0.503 | 4.579 | 0.659 | 4.071 | 0.282 | 5.087 | 0.521 |

FIG. 22A

| chr | Gene | glmnet | glmnet2 | glmnetF | glmnet2F | glmnetF.coef | glmnet2F.coef | mean | sd | nonCancer.mean | nonCancer.sd | Cancer.mean | Cancer.sd |
|---|---|---|---|---|---|---|---|---|---|---|---|---|---|
| chr17 | LINC00670 | 16 | 0 | 15 | NA | 0.02 | NA | 3.693 | 0.686 | 3.181 | 0.253 | 4.205 | 0.594 |
| chr15 | LOC100128714 | 23 | 0 | 23 | NA | 0.03 | NA | 4.936 | 0.416 | 4.637 | 0.189 | 5.235 | 0.363 |
| chr02 | LOC151171 | 23 | 2 | 23 | 2 | 0.029 | 0.009 | 4.412 | 0.311 | 4.206 | 0.229 | 4.617 | 0.238 |
| chr16 | LOC283867 | 0 | 0 | 1 | NA | 0.001 | NA | 5.383 | 0.483 | 5.035 | 0.226 | 5.73 | 0.417 |
| chr05 | LOC285629 | 65 | 49 | 65 | 48 | 0.083 | 0.243 | 1.836 | 0.665 | 1.349 | 0.425 | 2.322 | 0.479 |
| chr06 | LY6G6F | 51 | 3 | 51 | 3 | -0.065 | -0.014 | 2.949 | 0.463 | 3.284 | 0.26 | 2.613 | 0.369 |
| chr21 | MIR5009 | 20 | 0 | 20 | NA | 0.025 | NA | 6.323 | 0.688 | 5.807 | 0.333 | 6.838 | 0.551 |
| chr02 | MRPS5 | 8 | 0 | 8 | NA | 0.01 | NA | 4.834 | 0.335 | 4.597 | 0.219 | 5.072 | 0.254 |
| chr17 | MYOCD | 46 | 0 | 46 | NA | 0.059 | NA | 4.255 | 0.662 | 3.756 | 0.238 | 4.753 | 0.568 |
| chr09 | NTRK2 | 36 | 49 | 36 | 49 | 0.046 | 0.245 | 6.424 | 0.314 | 6.225 | 0.244 | 6.624 | 0.242 |
| chr14 | OSGEP | 13 | 0 | 13 | NA | -0.016 | NA | 3.706 | 0.316 | 3.926 | 0.18 | 3.486 | 0.264 |
| chr04 | PCDH7 | 10 | 0 | 10 | NA | 0.012 | NA | 5.744 | 0.463 | 5.424 | 0.243 | 6.064 | 0.407 |
| chr06 | PDE10A | 42 | 0 | 42 | NA | 0.053 | NA | 6.079 | 0.468 | 5.732 | 0.251 | 6.426 | 0.365 |
| chr10 | PDLIM1 | 9 | 0 | 9 | NA | -0.011 | NA | 6.426 | 0.203 | 6.562 | 0.133 | 6.29 | 0.167 |
| chr06 | PTCRA | 42 | 0 | 42 | NA | -0.053 | NA | 4.151 | 0.309 | 4.374 | 0.188 | 3.927 | 0.236 |
| chr14 | RHOJ | 57 | 28 | 57 | 27 | 0.073 | 0.138 | 4.586 | 0.343 | 4.343 | 0.225 | 4.829 | 0.259 |
| chr06 | RWDD2A | 0 | 0 | NA | NA | NA | NA | 1.383 | 0.34 | 1.246 | 0.303 | 1.519 | 0.323 |
| chr08 | SFRP1 | 56 | 0 | 57 | NA | 0.072 | NA | 4.423 | 0.422 | 4.116 | 0.197 | 4.73 | 0.358 |
| chr07 | TSPAN33 | 9 | 16 | 9 | 16 | -0.011 | -0.082 | 5.367 | 0.151 | 5.454 | 0.126 | 5.28 | 0.121 |
| chr02 | TWIST2 | 6 | 0 | 6 | NA | 0.008 | NA | 4.661 | 0.367 | 4.405 | 0.208 | 4.918 | 0.306 |
| chr11 | UCP3 | 41 | 13 | 41 | 13 | -0.052 | -0.065 | 4.271 | 0.188 | 4.394 | 0.132 | 4.149 | 0.151 |
| chr02 | ZNF2 | 10 | 0 | 10 | NA | 0.013 | NA | 3.594 | 0.415 | 3.304 | 0.231 | 3.883 | 0.351 |
| chr19 | ZNF573 | 16 | 0 | 16 | NA | 0.02 | NA | 3.688 | 0.459 | 3.359 | 0.206 | 4.017 | 0.403 |

FIG. 22B

CELL-FREE DNA HYDROXYMETHYLATION PROFILES IN THE EVALUATION OF PANCREATIC LESIONS

TECHNICAL FIELD

The present invention relates generally to epigenetic analysis, and more particularly relates to combined workflow methods for obtaining multiple types of information from a single biological sample. The invention finds utility in the fields of genomics, medicine, diagnostics, and epigenetic research.

BACKGROUND

Translational research using genomic and proteomic technologies has provided novel molecular insights into the pathogenesis of pancreatic cancer and the biology of the local tumor microenvironment, but has yet to yield robust diagnostic biomarkers to impact early diagnosis of a disease. This is reflected by a very low overall 5-year survival rate of 8.5%; see "Cancer Stat Facts: Pancreas Cancer" (National Cancer Institute Surveillance, Epidemiology, and End Results Program, 2017), retrieved on Oct. 16, 2017 from seer.cancer.gov/statfacts/html/ pancreas.html. Pancreatic cancer often presents late and has few symptoms, at which point only 10% to 20% of patients are eligible for surgical resection.

The pancreas consists of acinar cells, ductal cells, centroacinar cells, endocrine islets, and stellate cells. The majority of pancreatic cancers are adenocarcinomas, with pancreatic ductal adenocarcinoma (PDAC) and its variants accounting for more than 90% of all pancreatic malignancies (Tempero et al. (2017) *Journal of the Comprehensive Cancer Network* 15(8): 1028-1060), with the next most common pathology being neuroendocrine tumors, followed by colloid carcinomas, solid-pseudopapillary tumors, acinar cell carcinomas, and pancreatoblastomas (Kleef et al. (2016), *Nature Reviews Disease Primers: Pancreatic Cancer* 2: 1-22). Tobacco smoking confers a two- to three-fold higher risk of pancreatic cancer and also demonstrates a dose-risk relationship, while contributing to approximately 15 to 30% of cases (ibid.), with smokers diagnosed 8 to 15 years younger than non-smokers (Anderson et al. (2012) *Am. J. Gastroenterol* 107(11):1730-39; Maisonneuve et al. (2010) *Dig Dis* 28(405):645-56). A family history of pancreatitis is contributory in approximately 10% of cases, and germline mutations in genes such as BRCA2, BRCA1, CDKN2A, ATM, STK11, PRSS1, MLH1 and PALB2 are also associated with pancreatic cancer with variable penetrance (Kleef, supra).

Age is a significant risk factor for pancreatic cystic lesions (PCLs) and pancreatic cancer. Zerboni et al. (2016) *Abstracts/Pancreatology* 16:S104 (Abstract ID: 1665) did a meta-analysis of 10 studies showing an overall prevalence of PCLs of 11%, with a higher rate of 16% in studies investigating subjects with a mean age greater than 55 years old. Studies using modem imaging technologies such as Magnetic Resonance Imaging (MRI) with contrast medium and cholangiopancreatography (MRCP) reported a significantly higher pooled prevalence of PCLs at 26% of subjects. Other known risk factors include, without limitation, diabetes mellitis, chronic pancreatitis, and obesity.

The management of PDAC presents physicians with challenges along the entire clinical spectrum, including early detection in high risk individuals, early diagnosis of patients with symptoms or imaging findings, prognostication of outcomes, and prediction of therapeutic responsiveness, which collectively have engendered intense research efforts to identify and validate biomarkers with sufficient clinical performance metrics to improve decision algorithms. Current guidelines in PDAC management are primarily limited to two biomarker recommendations: carbohydrate antigen 19-9 (CA19-9 or sialyl Lewis antigen) and carcinoembryonic antigen (CEA). CA19-9 is relied upon to guide surgery decisions, use of adjuvant therapy, or the detection of post-operative tumor recurrence, with the recognition that 10% of the population does not secrete the antigen. See Swords et al. (2016) *Onco Targets Ther* 9: 7459-67 and U.S. Pat. No. 8,632,98. Furthermore, the restricted sensitivity and specificity of CA 19-09 as a biomarker for pancreatic cancer suggests limited diagnostic potential. CEA levels are assessed in pancreatic cyst fluid and then combined with imaging and clinical parameters to distinguish mucinous and non-mucinous cysts in order to mitigate risk (Fonseca et al. (2018) *Pancreas* 47(3): 272-79; Elta et al. (2018) *Am. J. Gastroenterology* 113: 464-79). However, CEA level does not correlate with the extent of disease (Schlieman et al. (2003) *Arch Surg.* 138)9): 951-56). Furthermore, while both tumor markers, if elevated, are useful in following patients with known disease, neither CA19-9 nor CEA has the sensitivity and specificity needed for use in screening patients to detect pancreatic cancer.

Molecular analyses of pancreatic cancer genomes reveal activating mutations in KRAS and inactivation of CDKN2A, TP53 and SMAD4, either through point mutation or copy number changes at >50% population frequency (Blankin et al. (2012) *Nature* 491(7424): 399-405; Waddell et al. (2015) *Nature* 518(7540):495-501; Jones et al. (2008) *Science* 321(5897):1801-06); however, much mutational heterogeneity exists, rendering this subset of genes inefficient in diagnosing patients. Molecular subtyping of pancreatic tumors using mutational-based data (Waddell (2015), supra) or gene expression signatures (REF), have not yet seen clinical application.

There remains an unmet and pressing need in the art for improved methods of detecting, diagnosing, predicting, assessing, treating, and monitoring pancreatic cancer, particularly PDAC. An ideal method would be reliable and non-invasive, optimally enabling analysis of tumor, microenvironment, pancreas, and immune cell DNA to identify genetic and epigenetic information that correlates with PDAC or an aspect thereof.

SUMMARY OF THE INVENTION

Tumor and normal cell DNA is released into the bloodstream, and a cell-free DNA (cfDNA) sample extracted therefrom can be analyzed with respect to genetic and epigenetic signatures. Epigenetic signatures include, by way of example, DNA methylation, i.e., the conversion of cytosine to 5-methylcytosine (5mC), and DNA hydroxymethylation, the oxidation of 5mC to 5-hydroxymethylcytosine (5hmC), mediated in the mammalian genome by the TET (Ten-Eleven Translocation) family of enzymes. Such signatures may come from cells that are normal, or from a tumor, the tumor microenvironment, the affected organ, or the immune system, all of which may change in response to health conditions such as in the case of pancreatic cancer.

The present invention is predicated on the discovery of a set of hydroxymethylation biomarkers that in combination with one or more clinical parameters and optionally one or more other types of biomarkers and/or patient-specific risk factors, exhibits a hydroxymethylation level that correlates in some way with pancreatic cancer, particularly PDAC or another exocrine pancreatic cancer. In some embodiments, the invention enables the determination of:

(a) the risk that a pancreatic lesion observed with an imaging scan, i.e., an identified pancreatic lesion, is cancerous;

(b) the risk that an identified noncancerous pancreatic lesion will become cancerous;

(c) the likelihood that a particular therapy for treating a subject with pancreatic cancer will be effective;

(d) the risk that a subject without an identified pancreatic lesion will, at some point, develop a pancreatic lesion, as well as (e) the risk of that lesion becoming cancerous.

Observing changes in the biomarker set over time can provide (or in some cases confirm) additional information such as:

(f) the effectiveness of a therapy a subject is undergoing in connection with an identified pancreatic lesion;

(g) an increase or decrease in the risk that an identified pancreatic lesion will develop into cancer;

(h) an increase or decrease in the likelihood that a subject without an observed pancreatic lesion will develop a pancreatic lesion, and (i) the risk of that lesion becoming cancerous; and (j) a change in an identified pancreatic lesion, including (j-1) a change in the size of a pancreatic lesion, (j-2) a change in the stage of a cancerous pancreatic lesion, (j-3) a change in the grade of a cancerous pancreatic lesion; (j-4) a change in the degree of invasiveness of a cancerous pancreatic lesion; and (j-5) the change from a local or regionalized invasive cancerous pancreatic lesion to a metastatic pancreatic cancer; as well as (j-6) the identification or confirmation of the pancreas as the primary tissue of origin in a cancer first identified through metastasis (i.e., initially a cancer of unknown origin).

It will thus be appreciated that the methods herein remain useful after surgical resection of a pancreatic lesion, in the context of monitoring post-surgical changes such as the development of additional lesions or the effectiveness of a post-surgical therapy (e.g., radiation, chemotherapy, other pharmacotherapy, etc.) However, of primary importance herein is the evaluation of an identified pancreatic lesion as more or less likely to be cancerous or to become cancerous. Equally important is the ability to identify a likely cancerous lesion at an early stage. These features of the invention in turn enable significant advances in the field, including the treatment of pancreatic cancer before the cancer has advanced or metastasized as well as a reduction in unnecessary surgery, i.e., removal of benign lesions.

In one embodiment of the invention, a method is provided for evaluating the risk that an identified pancreatic lesion in a patient is cancerous, the method comprising: (a) obtaining a cell-free DNA sample from the patient; (b) enriching for hydroxymethylated DNA in the sample; (c) quantifying the nucleic acids in the enriched sample that map to each of a plurality of selected loci in a reference hydroxymethylation profile, wherein each selected locus comprises a hydroxymethylation biomarker; (d) comparing, at each locus, the hydroxymethylation level of the sample with the hydroxymethylation level in the reference profile, to ascertain differences in hydroxymethylation levels between the sample and the reference profile for each biomarker; and (e) calculating an index value representing the risk that the pancreatic lesion is cancerous from the comparison in step (d) combined with at least one additional parameter correlated with the risk that an individual has pancreatic cancer. The additional parameter may be a clinical parameter, an additional type of biological marker (i.e., a biological marker not related to hydroxymethylation), or a combination thereof.

The selected loci that serve as hydroxymethylation biomarkers herein comprise loci selected for their relevance to pancreatic cancer, particularly an exocrine pancreatic cancer such as PDAC. By "relevance" is meant that a hydroxymethylation biomarker locus, alone or in combination with one or more other hydroxymethylation biomarker loci, tends to exhibit an increase or decrease in hydroxymethylation in a manner that correlates with the risk, presence, absence, type, size, stage, invasiveness, grade, location, diagnosis, prognosis, outcome, and/or or likelihood of treatment responsiveness of pancreatic cancer, including determinations (a) through (j) above. The reference hydroxymethylation profile is a data set representing the hydroxymethylation level of each of a plurality of hydroxymethylation biomarkers, where the data set is a composite of hydroxymethylation profiles of a plurality of individuals having at least one shared characteristic.

It should be noted that some of the individual hydroxymethylation biomarkers disclosed herein may not have significant individual significance in the evaluation of a pancreatic lesion, but when used in combination with other hydroxymethylation biomarkers disclosed herein and clinical parameters impacting on the evaluation and monitoring of a pancreatic lesion, optionally further combined with one or more other types of biomarkers and/or patient-specific risk factors, become significant in discriminating as a method of the invention requires, e.g., between a subject who has pancreatic cancer and a subject who does not have pancreatic cancer, or between a subject who is likely to develop pancreatic cancer and a subject who is not likely to develop pancreatic cancer, etc. The methods of the present invention provide an improvement over currently available methods of evaluating the risk that a subject has pancreatic cancer or is likely to develop pancreatic cancer, by using the biomarkers defined herein.

In one aspect of the embodiment, a focused reference profile can be used to improve the accuracy of the above method. That is, different types of reference hydroxymethylation profiles may be constructed from different population groups, and an appropriate reference profile can then be selected for the evaluation of a particular patient. For patients who have chronic inflammation of the pancreas, i.e., chronic pancreatitis, a narrowed, or focused, reference profile generated from a set of individuals with chronic pancreatitis would be selected. Another focused reference profile might be constructed from a set of individuals who are diabetic, or obese, or cigarette smokers, and used in the evaluation of patients who are diabetic, obese, or smokers, respectively. These focused reference profiles can also be used in combination, depending on the attributes of the patient undergoing evaluation.

In another aspect, the cell-free DNA sample is extracted from a blood sample obtained from the patient. In another aspect, the cell-free DNA sample is extracted from a sample of pancreatic cyst fluid obtained from the patient.

In an additional aspect of the embodiment, step (b) comprises ligating adapters onto the DNA, functionalizing 5hmC residues in the DNA with an affinity tag that allows selective capture of tagged cfDNA, and removing the tagged cfDNA from the sample. The affinity tag may be a biotin moiety, in which case the functionalization of the 5hmC residues comprises biotinylation. The biotinylated cfDNA may then be captured using a solid support having a surface functionalized with a biotin-binding protein such as avidin or streptavidin. Step (b) may then further comprise amplifying the cfDNA without releasing the captured cfDNA from the support, to give a plurality of amplicons; sequencing the amplicons; and quantifying the nucleic acids that map to the reference loci from the sequence reads.

In another embodiment, a method is provided for monitoring a patient who has an identified pancreatic lesion, i.e., a lesion identified in an imaging scan. As with the preceding embodiment, the method is a non-invasive way of enabling the practitioner to identify changes in a previously identified pancreatic lesion and thereby determine, for example, whether the lesion is progressing toward cancer. The method comprises:

(a) obtaining an initial cell-free DNA sample from the patient;
(b) enriching for hydroxymethylated DNA in the initial sample;
(c) quantifying the nucleic acids in the enriched initial sample that map to each of a plurality of selected loci in a reference hydroxymethylation profile, wherein each selected locus comprises a hydroxymethylation biomarker;
(d) comparing, at each locus, the hydroxymethylation level of the enriched cell-free DNA in the initial sample with the hydroxymethylation level in the reference profile, to ascertain differences in hydroxymethylation levels between the sample and the reference profile for each biomarker;
(e) generating an initial hydroxymethylation profile for the patient comprising the hydroxymethylation level of the enriched cell-free DNA in the initial sample, at each locus;
(f) repeating steps (a) through (c) at a later time with a subsequent cell-free DNA sample obtained from the patient;
(g) generating a subsequent hydroxymethylation profile for the patient comprising the hydroxymethylation level of the enriched cell-free DNA in the subsequent sample, at each locus; and
(h) comparing, at each locus, the hydroxymethylation level of the enriched cell-free DNA in the subsequent sample to the hydroxymethylation level of the enriched cell-free DNA in the initial sample, to ascertain a change in the pancreatic lesion.

In the context of ongoing assessment, steps (f) through (h) are repeated at selected time intervals throughout an extended monitoring period.

The change in the pancreatic lesion is thus determined by a change in the patient's hydroxymethylation profile over time, at a plurality of hydroxymethylation biomarker loci, optimally in combination with one or more other risk factors or clinical parameters. The change in the lesion may be, for example, a change in size, a change in grade, a change in shape, a change in lymph node involvement, a change in invasiveness, or two or more of any of the foregoing.

In a related embodiment, the invention provides a method for managing a patient with a pancreatic lesion identified in an imaging scan, the method comprising:

(a) obtaining an initial cell-free DNA sample from the patient;
(b) enriching for hydroxymethylated DNA in the sample;
(c) quantifying the nucleic acids in the enriched initial sample that map to each of a plurality of selected loci in a reference hydroxymethylation profile, wherein each selected locus comprises a hydroxymethylation biomarker;
(d) comparing, at each locus, the hydroxymethylation level of the enriched cell-free DNA in the initial sample with the hydroxymethylation level in the reference profile, to ascertain differences in hydroxymethylation levels between the sample and the reference profile for each biomarker;
(e) generating an initial hydroxymethylation profile for the patient comprising the hydroxymethylation level of the enriched cell-free DNA in the initial sample, at each locus;
(f) repeating steps (a) through (c) at a later time with a subsequent cell-free DNA sample obtained from the patient;
(g) generating a subsequent hydroxymethylation profile for the patient comprising the hydroxymethylation level of the enriched cell-free DNA in the subsequent sample, at each locus;
(h) comparing, at each locus, the hydroxymethylation level of the enriched cell-free DNA in the subsequent sample to the hydroxymethylation level of the enriched cell-free DNA in the initial sample, to ascertain a change in the pancreatic lesion; and
(f) based on the comparison in step (e), determining whether to treat the patient.

Steps (a) through (h) of the method may be repeated at selected time intervals within the context of an ongoing monitoring period.

If the changes in the patient's hydroxymethylation profile at a plurality of hydroxymethylation biomarker loci provides evidence of a change in the pancreatic lesion that, in the practitioner's opinion, warrants treatment, the treatment itself may be selected based on the change in the in the patient's hydroxymethylation profile at one or more of the selected loci. Treatment may involve radiation therapy, chemotherapy, other pharmacotherapy, surgical resection of the lesion, or a combination thereof.

In another related embodiment, the invention is directed to a method for monitoring the effectiveness of treatment of a patient with an identified pancreatic lesion. The method comprises:

(a) obtaining an initial cell-free DNA sample from a patient who is being treated;
(b) enriching for hydroxymethylated DNA in the sample;
(c) quantifying the nucleic acids in the enriched initial sample that map to each of a plurality of selected loci in a reference hydroxymethylation profile, wherein each selected locus comprises a hydroxymethylation biomarker;
(d) comparing, at each locus, the hydroxymethylation level of the enriched cell-free DNA in the initial sample with the hydroxymethylation level in the reference profile, to ascertain differences in hydroxymethylation levels between the sample and the reference profile for each biomarker;
(e) generating an initial hydroxymethylation profile for the patient comprising the hydroxymethylation level of the enriched cell-free DNA in the initial sample, at each locus;
(f) repeating steps (a) through (c) at a later time with a subsequent cell-free DNA sample obtained from the patient;
(g) generating a subsequent hydroxymethylation profile for the patient comprising the hydroxymethylation level of the enriched cell-free DNA in the subsequent sample, at each locus;
(h) comparing, at each locus, the hydroxymethylation level of the enriched cell-free DNA in the subsequent sample to the hydroxymethylation level of the enriched cell-free DNA in the initial sample, to ascertain a change in the pancreatic lesion; and (i) if the comparison in step (e) evidences changes in the patient's hydroxymethylation profile that correlate with a progression toward cancer, changing the treatment protocol.

The progression toward cancer may involve a change in lesion size, grade, shape, nodal involvement, invasiveness, or two or more of any of the foregoing.

In another embodiment, the invention provides a method for reducing the risk of unnecessary pancreatic surgery, i.e., for reducing the risk that a pancreatic lesion surgically removed from a patient is benign. The method comprises, prior to surgery:

(a) obtaining a cell-free DNA sample from the patient;
(b) enriching for hydroxymethylated DNA in the sample;
(c) quantifying the nucleic acids in the enriched sample that map to each of a plurality of selected loci in a reference hydroxymethylation profile, wherein each selected locus comprises a hydroxymethylation biomarker;
(d) comparing, at each locus, the hydroxymethylation level of the sample with the hydroxymethylation level in the reference profile, to ascertain differences in hydroxymethylation levels between the sample and the reference profile for each biomarker; and
(e) calculating an index value representing the risk that the pancreatic lesion is cancerous from the comparison in step (d) combined with at least one additional parameter correlated with the risk that an individual has pancreatic cancer; and
(f) carrying out surgical resection of the pancreatic lesion only if the index value is greater than a value corresponding to a low risk of cancer.

In another embodiment, the invention provides a kit for carrying out any of the methods described herein in the analysis of a cell-free DNA sample obtained from a patient, where the kit comprises: at least one reagent for the determination of hydroxymethylation level at each of a plurality of hydroxymethylation biomarker loci in a cell-free DNA sample; a solid support for capturing affinity-tagged 5hmC-containing cell-free DNA in the sample; and written instructions for the use of the at least one reagent and the solid support in carrying out the method.

In one aspect of the embodiment, the kit further includes instructions for accessing and using software designed to perform modeling and prediction.

In an additional embodiment, the kit comprises: a DNA B-glucosyl transferase; UDP glucose modified with a chemoselective group; a biotin moiety; a solid support having a surface functionalized with a biotin-binding protein; an adaptor comprising a molecular barcode; and written instructions for carrying out the method. As with the preceding embodiment, the kit may additionally include instructions for accessing and using software designed to perform modeling and prediction.

In a further embodiment, the invention provides a method for determining the likelihood that an individual at risk for developing pancreatic cancer has pancreatic cancer. The method comprises the following steps:

(a) obtaining a cell-free DNA sample from the patient;
(b) enriching for hydroxymethylated DNA in the sample;
(c) quantifying the nucleic acids in the enriched sample that map to each of a plurality of selected loci in a reference hydroxymethylation profile, wherein each selected locus comprises a hydroxymethylation biomarker;
(d) comparing, at each locus, the hydroxymethylation level of the sample with the hydroxymethylation level in the reference profile, to ascertain differences in hydroxymethylation levels between the sample and the reference profile for each biomarker; and
(e) calculating an index value representing the likelihood that the individual has pancreatic cancer from the comparison in step (d).

In one aspect, the method further includes, prior to step (a), identifying the individual as being at risk for developing pancreatic cancer from one or more parameters selected from: an identified pancreatic lesion; pancreatic inflammation; jaundice; age; weight; gender; ethnicity; family history; genetic mutations; diabetes; physical activity; diet; pro-inflammatory cytokine levels; and cigarette smoking.

In another embodiment, an improved multi-cancer test is provided that determines the likelihood that an individual has pancreatic cancer and at least one additional type of cancer, wherein the improvement comprises determining the likelihood that the individual has pancreatic cancer by:

(a) obtaining a cell-free DNA sample from the individual;
(b) enriching for hydroxymethylated DNA in the sample;
(c) quantifying the nucleic acids in the enriched sample that map to each of a plurality of selected loci in a reference hydroxymethylation profile, wherein each selected locus comprises a hydroxymethylation biomarker;
(d) comparing, at each locus, the hydroxymethylation level of the sample with the hydroxymethylation level in the reference profile, to ascertain differences in hydroxymethylation levels between the sample and the reference profile for each biomarker; and
(e) calculating an index value representing the likelihood that the individual has pancreatic cancer from the comparison in step (d).

The test may further include eliminating false positives, false negatives, or both false positives and false negatives for the at least one additional type of cancer prior to (a).

The at least one additional type of cancer can be any type of cancer, including, without limitation, bladder cancer; cancers of the blood and bone marrow; brain cancer; breast cancer; cervical cancer; colorectal cancer; esophageal cancer; liver cancer; lung cancer; ovarian cancer; prostate cancer; renal cancer; skin cancer; testicular cancer; thyroid cancer; and uterine cancer.

In one aspect of this embodiment, the at least one additional type of cancer is selected from breast cancer, colorectal cancer, lung cancer, and prostate cancer.

BRIEF DESCRIPTION OF THE DRAWINGS

In FIG. 10, "Hallmark" refers to the Hallmark gene sets in the MSigDB collections; "C2" refers to curated gene sets inclusive of the Biocarta, KEGG and Reactome databases; "C5.BP" refers to the "biological processes" subset of the Gene Ontology (GO) Consortium annotated gene sets; "C6" MSigDB oncogenic signature of cellular pathways that are often dis-regulated in cancer; "C7" (also referred to as "immuneSigDB") refers to the database of gene sets that represent cell types, states, and perturbations within the immune system.

FIG. 15 represents the training performed with 75% of the data, and FIG. 16 represents the test performed on the remaining 25% of the data, as described in Example 1 herein.

FIG. 20 provides hydroxymethylation biomarker data obtained using the methods documented in Example 1 herein. The table of FIG. 20 identifies the genes by name and chromosome location and includes normalized values obtained with glmnet, glmnet2, glmnetF, and glmnet2F regularization methods; glmnetF and glmnet2F coefficients; mean and standard deviation; mean and standard deviation for the cancer cohort (identified as Mean-C and SD-C, respectively); mean and standard deviation for the non-cancer cohort (Mean-NC and SD-NC, respectively); Vote, computed as the sum of the glmnetF and glmnet2F normalized values for each gene; and the ratio of cancer-to-non-cancer (C/NC) means.

FIG. 21 provides a list of hydroxymethylation biomarkers suitable for use in conjunction with the present invention, by gene name, location, and glmnet value, identified using Study Group 2 in Example 2.

FIG. 22 is analogous to FIG. 20 but provides the biomarker data for the 41 genes of Table 4, infra, using Study Group 3 in Example 3.

DETAILED DESCRIPTION OF THE INVENTION

1. Terminology and Overview

Figure 1:
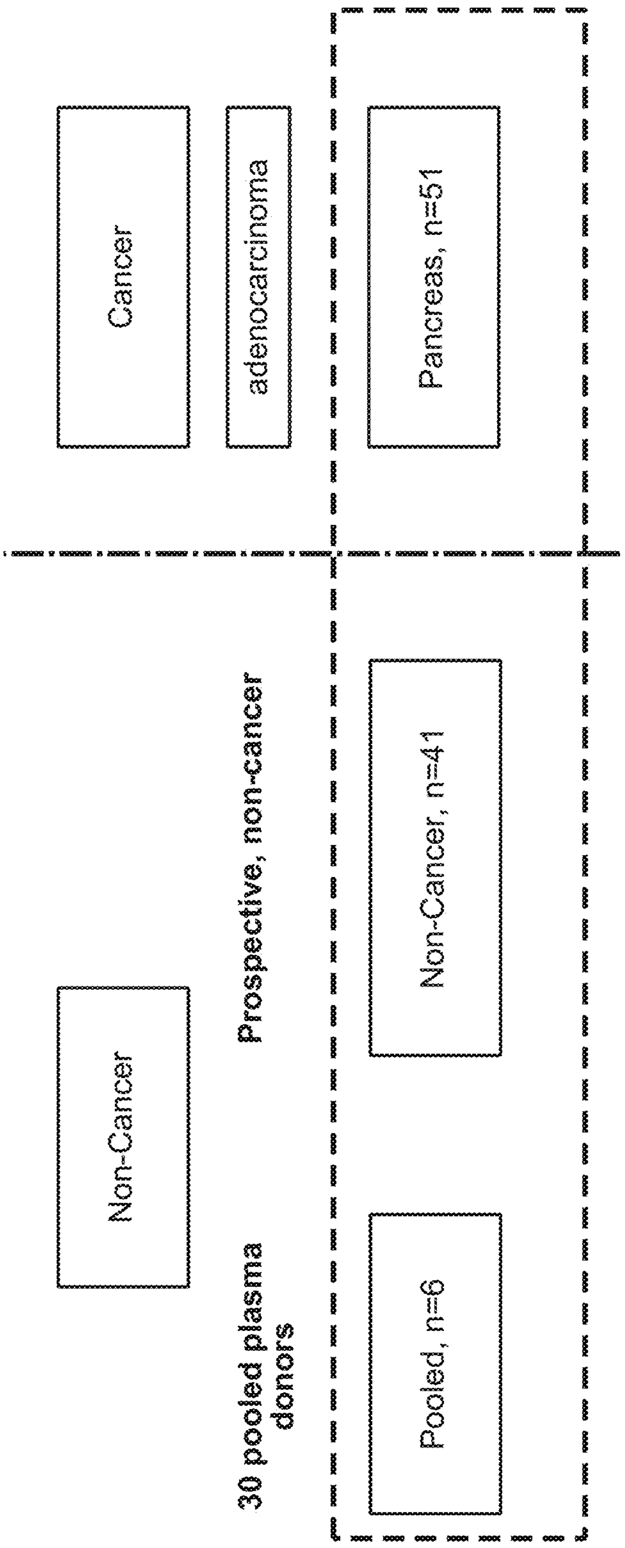
FIG. 1 schematically depicts the study cohorts employed in Example 1 herein. Cohorts: PDAC, n=51, Non-cancer, n=41. Pooled non-cancer replicates were included across multiple 5hmC assay processing and sequencing batches.
Figure 2:
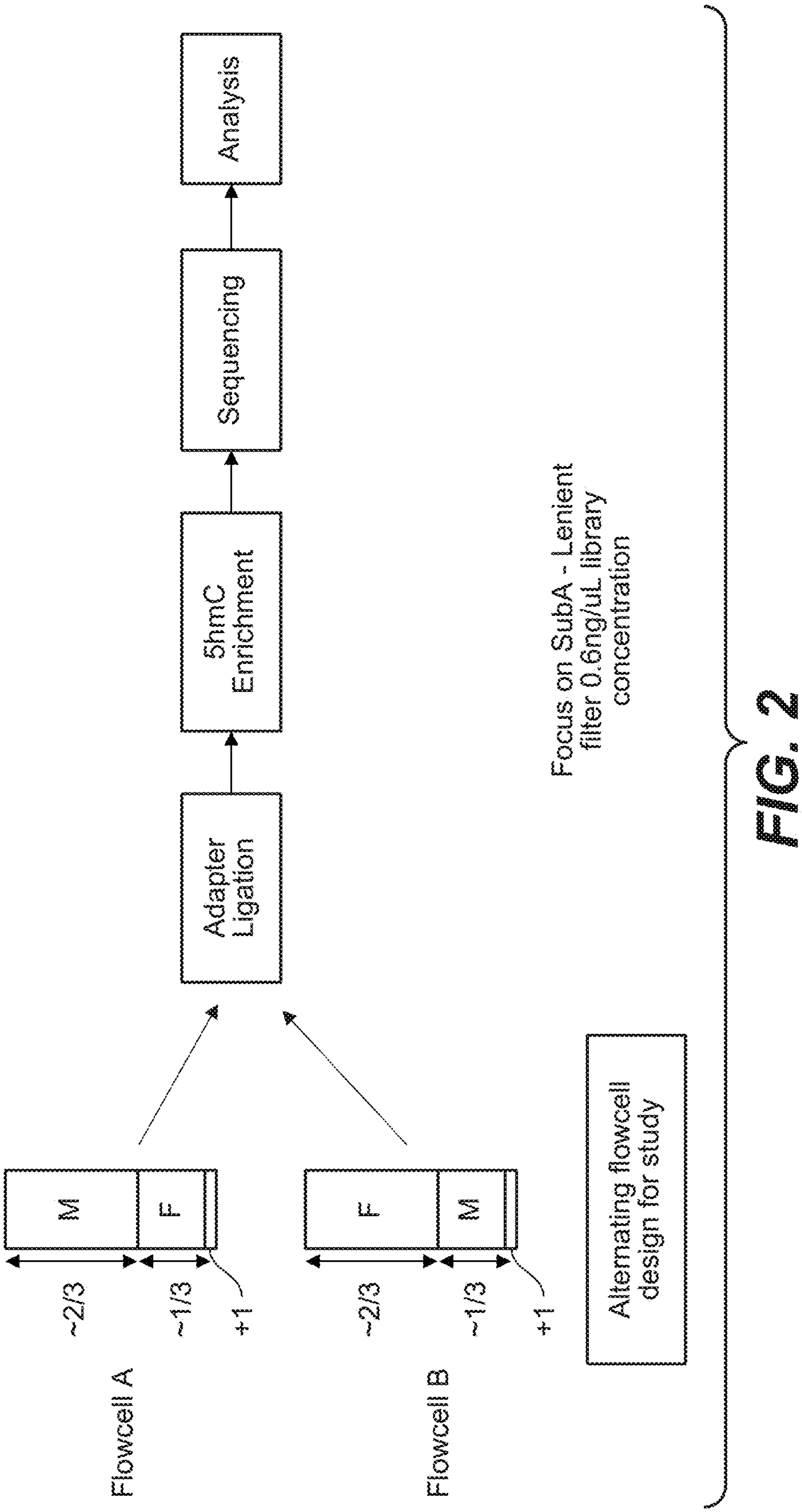
FIG. 2 schematically depicts the sample processing workflow used in Example 1, including two alternating gender-divided flow cell constructs for detection of sample swaps.

Unless defined otherwise, all technical and scientific terms used herein have the meaning commonly understood by one of ordinary skill in the art to which the invention pertains. Specific terminology of particular importance to the description of the present invention is defined below. Other relevant terminology is defined in International Patent Publication No. WO 2017/176630 to Quake et al. for "Non-invasive Diagnostics by Sequencing 5-Hydroxymethylated Cell-Free DNA." The aforementioned patent publication as well as all other patent documents and publications referred to herein are expressly incorporated by reference.

In this specification and the appended claims, the singular forms "a," "an" and "the" include plural referents unless the context clearly dictates otherwise. Thus, for example, "an adapter" refers not only to a single adapter but also to two or more adapters that may be the same or different, "a template molecule" refers to a single template molecule as well as a plurality of template molecules, and the like.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

The term "sample" as used herein relates to a material or mixture of materials, typically, although not necessarily, in liquid form, containing one or more analytes of interest.

The term "biological sample" as used herein relates to a sample derived from a biological fluid, cell, tissue, or organ of a human subject, comprising a mixture of biomolecules including proteins, peptides, lipids, nucleic acids, and the like. Generally, although not necessarily, the sample is a blood sample such as a whole blood sample, a serum sample, or a plasma sample, or a sample of pancreatic cyst fluid.

A "nucleic acid sample" as that term is used herein refers to a biological sample comprising nucleic acids. The nucleic acid sample may be a cell-free nucleic acid sample that comprises nucleosomes, in which case the nucleic acid sample is sometimes referred to herein as a "nucleosome sample." The nucleic acid sample may also be comprised of cell-free DNA wherein the sample is substantially free of histones and other proteins, such as will be the case following cell-free DNA purification. The nucleic acid samples herein may also contain cell-free RNA.

A "sample fraction" refers to a subset of an original biological sample, and may be a compositionally identical portion of the biological sample, as when a blood sample is divided into identical fractions. Alternatively, the sample fraction may be compositionally different, as will be the case when, for example, certain components of the biological sample are removed, with extraction of cell-free nucleic acids being one such example.

As used herein, the term "cell-free nucleic acid" encompasses both cell-free DNA and cell-free RNA, where the cell-free DNA and cell-free RNA may be in a cell-free fraction of a biological sample comprising a body fluid. The body fluid may be blood, including whole blood, serum, or plasma, or it may be urine, cyst fluid, or another body fluid. In many instances, the biological sample is a blood sample, and a cell-free nucleic acid sample is extracted therefrom using now-conventional means known to those of ordinary skill in the art and/or described in the pertinent texts and literature; kits for carrying out cell-free nucleic acid extraction are commercially available (e.g., the AllPrep® DNA/RNA Mini Kit and QIAmp® DNA Blood Mini Kit, both available from Qiagen, or the MagMAX Cell-Free Total Nucleic Acid Kit and the MagMAX DNA Isolation Kit, available from ThermoFisher Scientific). Also see, e.g., Hui et al. Fong et al. (2009) Clin. Chem. 55 (3): 587-598.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Of particular interest herein are modified cytosine residues, including 5-methylcytosine and oxidized forms thereof, such as 5-hydroxymethylcytosine, 5-formylcytosine, and 5-carboxymethylcytosine.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, and up to about 10,000 or more bases composed of nucleotides, e.g., deoxyribonucleotides or ribonucleotide. Nucleic acids may be produced enzymatically, chemically synthesized, or naturally obtained.

The term "oligonucleotide" as used herein denotes a single-stranded multimer of nucleotide of from about 2 to 200 nucleotides, up to 500 nucleotides in length.

Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.).

The terms "duplex" and "duplexed" are used interchangeably herein to describe two complementary polynucleotides that are base-paired, i.e., hybridized together. A DNA duplex is referred to herein as "double-stranded DNA" or "dsDNA" and may be an intact molecule or a molecular segment. For example, the dsDNA herein referred to as barcoded and adapter-ligated is an intact molecule, while the dsDNA formed between the nucleic acid tails of proximity probes in a proximity extension assay is a dsDNA segment.

The term "strand" as used herein refers to a single strand of a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, "positive" and "negative" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

"Adapters" as that term is used herein are short synthetic oligonucleotides that serve a specific purpose in a biological analysis. Adapters can be single-stranded or double-stranded, although the preferred adapters herein are double-stranded. In one embodiment, an adapter may be a hairpin adapter (i.e., one molecule that base pairs with itself to form a structure that has a double-stranded stem and a loop, where the 3' and 5' ends of the molecule ligate to the 5' and 3' ends of a double-stranded DNA molecule, respectively). In another embodiment, an adapter may be a Y-adapter. In another embodiment, an adapter may itself be composed of two distinct oligonucleotide molecules that are base paired with each other. As would be apparent, a ligatable end of an adapter may be designed to be compatible with overhangs made by cleavage by a restriction enzyme, or it may have blunt ends or a 5' T overhang. The term "adapter" refers to double-stranded as well as single-stranded molecules. An adapter can be DNA or RNA, or a mixture of the two. An adapter containing RNA may be cleavable by RNase treatment or by alkaline hydrolysis. An adapter may be 15 to 100 bases, e.g., 50 to 70 bases, although adapters outside of this range are envisioned.

The term "adapter-ligated," as used herein, refers to a nucleic acid that has been ligated to an adapter. The adapter can be ligated to a 5' end and/or a 3' end of a nucleic acid molecule. As used herein, the term "adding adapter sequences" refers to the act of adding an adapter sequence to the end of fragments in a sample. This may be done by filling in the ends of the fragments using a polymerase, adding an A tail, and then ligating an adapter comprising a T overhang onto the A-tailed fragments. Adapters are usually ligated to a DNA duplex using a ligase, while with RNA, adapters are covalently or otherwise attached to at least one end of a cDNA duplex preferably in the absence of a ligase.

The term "asymmetric adapter", as used herein, refers to an adapter that, when ligated to both ends of a double stranded nucleic acid fragment, will lead to a top strand that contains a 5' tag sequence that is not the same as or complementary to the tag sequence at the 3' end. Examples of asymmetric adapters are described in U.S. Pat. Nos. 5,712,126 and 6,372,434 to Weissman et al., and International Patent Publication No. WO 2009/032167 to Bignell et al. An asymmetrically tagged fragment can be amplified by two primers: a first primer that hybridizes to a first tag sequence added to the 3' end of a strand; and a second primer that hybridizes to the complement of a second tag sequence added to the 5' end of a strand. Y-adapters and hairpin adapters (which can be cleaved, after ligation, to produce a "Y-adapter") are examples of asymmetric adapters.

The term "Y-adapter" refers to an adapter that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adapter-tagged double-stranded DNA that has been ligated to a Y-adapter is asymmetrically tagged in that it has the sequence of one strand of the Y-adapter at one end and the other strand of the Y-adapter at the other end. Amplification of nucleic acid molecules that have been joined to Y-adapters at both ends results in an asymmetrically tagged nucleic acid, i.e., a nucleic acid that has a 5' end containing one tag sequence and a 3' end that has another tag sequence.

The term "hairpin adapter" refers to an adapter that is in the form of a hairpin. In one embodiment, after ligation the hairpin loop can be cleaved to produce strands that have non-complementary tags on the ends. In some cases, the loop of a hairpin adapter may contain a uracil residue, and the loop can be cleaved using uracil DNA glycosylase and endonuclease VIII, although other methods are known.

The term "adapter-ligated sample", as used herein, refers to a sample that has been ligated to an adapter. As would be understood given the definitions above, a sample that has been ligated to an asymmetric adapter contains strands that have non-complementary sequences at the 5' and 3' ends.

The term "amplifying" as used herein refers to generating one or more copies, or "amplicons," of a template nucleic acid, such as may be carried out using any suitable nucleic acid amplification technique, such as technology, such as PCR, NASBA, TMA, and SDA.

The terms "enrich" and "enrichment" refer to a partial purification of template molecules that have a certain feature (e.g., nucleic acids that contain 5-hydroxymethylcytosine) from analytes that do not have the feature (e.g., nucleic acids that do not contain hydroxymethylcytosine). Enrichment typically increases the concentration of the analytes that have the feature by at least 2-fold, at least 5-fold or at least 10-fold relative to the analytes that do not have the feature. After enrichment, at least 10%, at least 20%, at least 50%, at least 80% or at least 90% of the analytes in a sample may have the feature used for enrichment. For example, at least 10%, at least 20%, at least 50%, at least 80% or at least 90% of the nucleic acid molecules in an enriched composition may contain a strand having one or more hydroxymethylcytosines that have been modified to contain a capture tag.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" (NGS) or "high-throughput sequencing", as used herein, refer to the so-called parallelized sequencing-by-synthesis or sequencing-by-ligation platforms currently employed by Illumina® assays and reagents, Life Technologies, Roche, etc. Next-generation sequencing methods may also include nanopore sequencing methods such as that commercialized by Oxford Nanopore Technologies, electronic detection methods such as Ion Torrent technology commercialized by Life Technologies, and single-molecule fluorescence- based methods such as that commercialized by Pacific Biosciences.

The term "read" as used herein refers to the raw or processed output of sequencing systems, such as massively parallel sequencing. In some embodiments, the output of the methods described herein is reads. In some embodiments, these reads may need to be trimmed, filtered, and aligned, resulting in raw reads, trimmed reads, aligned reads.

A "Unique Feature Identifier" (UFI) sequence refers to a relatively short nucleic acid sequence that serves to identify a feature of a nucleic acid molecule. Nucleic acid template molecules and amplicons thereof that contain a UFI are sometimes referred to herein as "barcoded" template molecules or amplicons. Examples of UFI sequence types include, without limitation, the following:

A "source identifier sequence" (or "source UFI" or "source barcode") identifies the biological sample (or other source) of origin. That is, each DNA molecule in a single sample is tagged with the same source identifier sequence, thus allowing the mixing of samples prior to sequencing. These UFIs may also be characterized as a "sample identifier sequence," a "sample UFI," or "sample barcode."

A "fragment identifier sequence" (or "fragment UFI" or "fragment barcode"): In a nucleic acid sample in which nucleic acids have been fragmented, each fragment in a sample is barcoded with a corresponding fragment identifier sequence. Sequence reads that have non-overlapping fragment identifier sequences represent different original nucleic acid template molecules, while reads that have the same fragment identifier sequences, or substantially overlapping fragment identifier sequences, likely represent fragments of the same template molecule. The unique feature identified here is the template nucleic acid molecule from which a fragment derives.

A "strand identifier sequence" (or "strand UFI" or "strand barcode") independently tags each of the two strands of a DNA duplex, so that the strand from which a read originates can be determined, i.e., as the W strand or the C strand.

A "5hmC identifier sequence" (or "5hmC barcode") identifies DNA fragments originating from 5hmC-containing cell-free DNA template molecules in a sample, i.e., "hydroxymethylated" DNA.

A "5mC identifier sequence" (or "5mC barcode") identifies DNA fragments originating from 5mC-containing cell-free DNA template molecules that do not contain 5hmC.

A "molecular UFI sequence" (or "molecular barcode") is appended to every nucleic acid template molecule in a sample, and is random, such that, providing the UFI sequence is of sufficient length, every nucleic acid template molecule is attached to a unique UFI sequence. Molecular UFI sequences, as is known in the art, can be used to account for and offset amplification and sequencer errors, allow a user to track duplicates and remove them from downstream analysis, and enable molecular counting, and, in turn, the determination of an analyte concentration. See, e.g., Casbon et al. (2011) Nuc. Acids Res. 39(12):1-8. The "unique feature" here is the identity of the nucleic acid template molecules.

In some embodiments, a UFI may have a length in the range of from 1 to about 35 nucleotides, e.g., from 3 to 30 nucleotides, 4 to 25 nucleotides, or 6 to 20 nucleotides. In certain cases, the UFI may be error-detecting and/or error-correcting, meaning that even if there is an error (e.g., if the sequence of the molecular barcode is mis-synthesized, misread or distorted during any of the various processing steps leading up to the determination of the molecular barcode sequence) then the code can still be interpreted correctly. The use of error-correcting sequences is described in the literature (e.g., in U.S. Patent Publication Nos. U.S. 2010/0323348 to Hamati et al. and U.S. 2009/0105959 to Braverman et al., both of which are incorporated herein by reference).

The oligonucleotides that serve as UFI sequences herein may be incorporated into DNA molecule using any effective means, where "incorporated into" is used interchangeably herein with "added to" and "appended to," insofar as the UFI can be provided at the end of a DNA molecule, near the end of a DNA molecule, or within a DNA molecule. For example, multiple UFIs can be end-ligated to DNA using a selected ligase, in which case only the final UFI is at the "end" of the molecule. In addition, in the proximity extension assay and histone modification methods described in detail infra, the UFI may be contained within the nucleic acid tail of a proximity probe, at the end of the nucleic acid tail of a proximity probe, or within the hybridized region generated upon the binding of probes to the protein target.

More generally, the term "detection" is used interchangeably with the terms "determining," "measuring," "evaluating," "assessing," "assaying," and "analyzing," to refer to any form of measurement, and include determining if an element is present or not. These terms include both quantitative and/or qualitative determinations. Assessing may be relative or absolute. "Assessing the presence of" thus includes determining the amount of a moiety present, as well as determining whether it is present or absent. Assessing the level at a hydroxymethylation biomarker locus refers to a determination of the degree of hydroxymethylation at that locus.

"Accuracy" refers to the degree of conformity of a measured or calculated quantity (a test reported value) to its accurate (or true) value. Clinical accuracy relates to the proportion of true outcomes (true positives (TP) or true negatives (TN) versus misclassified outcomes (false positives (FP) or false negatives (FN), and may be stated as a sensitivity, specificity, positive predictive values (PPV) or negative predictive values (NPV), or as a likelihood, or odds ratio, among other measures.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Clinical parameters" encompass all non-sample biomarkers of subject health status or other characteristics, such as, without limitation, lesion size; lesion location; presence or absence of pancreatic inflammation; presence or absence of other symptoms; patient age; weight; jaundice; gender; ethnicity; family history; genetic mutations; diabetes mellitus (including Type I and Type II diabetes); physical activity; diet; pro-inflammatory cytokine levels; and smoking status of the patient.

A "formula," "algorithm," or "model" is any mathematical equation, algorithmic, analytical or programmed process, or statistical technique that takes one or more continuous or categorical inputs and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining hydroxymethylation levels at various biomarker loci and clinical parameters, optionally in further combination with other factors (e.g., non-hydroxymethylation biomarkers), are linear and non-linear equations and statistical classification analyses to determine the relationship between hydroxymethylation levels at the biomarker loci detected in a patient sample and the patient's risk of having or developing pancreatic cancer. In panel and combination construction, of particular interest are structural and syntactic statistical classification algorithms, and methods of risk index construction, utilizing pattern recognition and machine learning features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Many such algorithmic techniques have been further implemented to perform both feature (loci) selection and regularization, such as in ridge regression, lasso, and elastic net, among others. Other techniques may be used in survival and time to event hazard analysis, including Cox, Weibull, Kaplan-Meier and Greenwood models well known to those of skill in the art. Many of these techniques are useful either combined with a hydroxymethylation biomarker selection technique, such as forward selection, backwards selection, or stepwise selection, complete enumeration of all potential biomarker sets, or panels, of a given size, genetic algorithms, or they may themselves include biomarker selection methodologies. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art.

"Risk," in the context of the present invention, relates to the probability that an event will occur over a specific time period, as in the development of pancreatic cancer, and can mean a subject's "absolute" risk or "relative" risk. Absolute risk can be measured with reference to index values developed from statistically valid historical cohorts that have been followed for the relevant time period; an example of absolute risk herein is knowledge of the outcome of a pancreatic biopsy following surgical resection, Relative risk refers to the ratio of absolute risks of a subject compared either to the absolute risks of low risk cohorts.

"Risk evaluation" or "evaluation of risk" in the context of the present invention encompasses making a prediction of the probability, odds, or likelihood that an event or disease state may occur, the rate of occurrence of the event or conversion from one state to another, i.e., from an apparently benign pancreatic lesion to a cancerous lesion, and the like. The methods of the present invention may be used to make continuous or categorical measurements of the risk of conversion of an apparently benign pancreatic lesion to a cancerous lesion. In the categorical scenario, the invention can be used to discriminate between normal and other subject cohorts at higher risk for developing pancreatic cancer. In other embodiments, the present invention may be used so as to discriminate those at risk for developing pancreatic cancer from those having pancreatic cancer, or those likely to respond well to a particular treatment from those who are not. Such differing uses may require different hydroxymethylation biomarker combinations and individualized panels, mathematical algorithms, and/or cut-off points, but be subject to the same measurements of accuracy and performance for the respective intended use.

A "hydroxymethylation level" or "hydroxymethylation state" is the extent of hydroxymethylation within a hydroxymethylation biomarker locus. The extent of hydroxymethylation is normally measured as hydroxymethylation density, e.g., the ratio of 5hmC residues to total cytosines, both modified and unmodified, within a nucleic acid region. Other measures of hydroxymethylation density are also possible, e.g., the ratio of 5hmC residues to total nucleotides in a nucleic acid region.

A "hydroxymethylation profile" or "hydroxymethylation signature" refers to a data set that comprises the hydroxymethylation level at each of a plurality of hydroxymethylation biomarker loci. The hydroxymethylation profile may be a reference hydroxymethylation profile that comprises composite a hydroxymethylation profile for a population of individuals with at least one shared characteristic, as explained infra. The hydroxymethylation profile may also be a patient hydroxymethylation profile, constructed from the measurement of hydroxymethylation levels at each of a plurality of hydroxymethylation biomarker sites.

A "reference hydroxymethylation profile" thus refers to a data set representing the hydroxymethylation level of each of a plurality of hydroxymethylation biomarkers, where the data set is a composite of hydroxymethylation profiles of a plurality of individuals having at least one shared characteristic, e.g., individuals who have had a pancreatic lesion identified in an imaging scan, individuals who have not had a pancreatic lesion identified in an imaging scan, individuals who have not had pancreatic cancer, individuals with chronic pancreatitis, and the like.

The "hydroxymethylation biomarkers" herein comprise loci selected for their relevance to pancreatic cancer, particularly an exocrine pancreatic cancer such as PDAC. By "relevance" is meant that a hydroxymethylation biomarker locus, alone or in combination with one or more other hydroxymethylation biomarker loci, tends to exhibit an increase or decrease in hydroxymethylation in a manner that correlates with the risk, presence, absence, type, size, stage, invasiveness, grade, location, diagnosis, prognosis, outcome, and/or or likelihood of treatment responsiveness of pancreatic cancer, including the determinations of any of steps (a) through (j) in the preceding section.

The term "locus" in the preceding paragraph and throughout this application refers to a site on a nucleic acid molecule, wherein the nucleic acid molecule may be single-stranded or double-stranded, and further wherein an individual locus (or multiple "loci") may be of any length, thus including a single CpG site as well as a full-length gene, or across larger features such as topologically associated domains, including when several such loci are aggregated into groups such as related sequence motifs, other homologies or functional characteristics (regardless of their adjacency or topological relationship). The loci herein may be contained within a gene body; within an annotation feature outside of the gene body, such as a promoter, an enhancer, a transcription initiation site, a transcription stop site, or a DNA binding site, or a combination thereof; or within an untranslated region, or "UTR" (including 3'UTRs and 5'UTRs). DNA binding sites that may contain one or more reference loci include, by way of example, silenced regions, transcription factor binding sites, transcription repressor binding sites, and CTCF binding sites (transposon repeat regions). Reference loci within CTCF binding sites are of particular interest, insofar as the CTCF gene codes for transcriptional repressor CTCF (also known as 11-zinc finger protein or CCCTC-binding factor), which in turn is involved in many cellular processes, including transcription regulation and regulation of chromatin architecture. See, for example, Juan et al. (2016) *Cell Reports* 14(5): 1246-1257; and Escedi et al. (2018) Epigenomes 2(1):3.

It should be noted that some of the individual hydroxymethylation biomarkers disclosed herein may not have significant individual significance in the evaluation of a pancreatic lesion, but when used in combination with other hydroxymethylation biomarkers disclosed herein and clinical parameters impacting on the evaluation and monitoring of a pancreatic lesion, optionally further combined with one or more other types of biomarkers and/or patient-specific risk factors, become significant in discriminating as a method of the invention requires, e.g., between a subject who has pancreatic cancer and a subject who does not have pancreatic cancer, or between a subject who is likely to develop pancreatic cancer and a subject who is not likely to develop pancreatic cancer, etc. The methods of the present invention provide an improvement over currently available methods of evaluating the risk that a subject has pancreatic cancer or is likely to develop pancreatic cancer, by using the biomarkers defined herein. To the extent that other biomarker pathway participants (i.e., other biomarker participants in common pathways with those biomarkers contained within the list of hydroxymethylation biomarkers herein are also relevant pathway participants in the subject pancreatic conditions, they may be functional equivalents to the hydroxymethylation biomarkers thus far disclosed. Furthermore, other unlisted hydroxymethylation biomarkers will be very highly correlated with the individual hydroxymethylation biomarkers listed here (for the purpose of this application, any two variables will be considered to be "very highly correlated" when they have a Coefficient of Determination (R2) of 0.5 or greater). The present invention encompasses such functional and statistical equivalents to the aforementioned hydroxymethylation biomarkers. Furthermore, the statistical utility of such additional hydroxymethylation biomarkers is substantially dependent on the cross-correlation between multiple biomarkers and any new biomarkers will often be required to operate within a panel in order to elaborate the meaning of the underlying biology.

The term "correlate" as used herein in reference to a variable (e.g., a value, a set of values, a disease state, a risk associated with the disease state, or the like) is a measure of the extent to which two or more variables fluctuate together. A positive correlation indicates the extent to which those variables increase or decrease in parallel. One example of a positive correlation is the relationship between a hydroxymethylation level at a hydroxymethylation biomarker locus, on the one hand, and the risk of developing pancreatic cancer, on the other, when the hydroxymethylation level increases as the risk of developing cancer increases. Conversely, a negative correlation would exist when the hydroxymethylation level biomarker at a hydroxymethylation biomarker locus decreases as the risk of developing cancer increases.

The term "pancreatic cancer" herein refers to an exocrine pancreatic cancer, particularly PDAC.

The present invention relates, in part, to the discovery that certain biological markers, particularly epigenetic markers relating to DNA hydroxymethylation, correlate in some way with pancreatic cancer, particularly an exocrine cancer such as PDAC. The methods involve measuring the hydroxymethylation level at each of a plurality of hydroxymethylation biomarker loci to generate a hydroxymethylation profile for a patient, and then comparing the patient's hydroxymethylation profile to a reference hydroxymethylation profile, at each locus. The biomarkers are differentially hydroxymethylated in subjects who have pancreatic cancer or are at risk of developing pancreatic cancer, particularly PDAC or another exocrine pancreatic cancer.

In some embodiments, the invention enables the determination of the risk that a pancreatic lesion observed with an imaging scan, i.e., an identified pancreatic lesion, is cancerous; the risk that an identified noncancerous pancreatic lesion will become cancerous; the likelihood that a particular therapy for treating a subject with pancreatic cancer will be effective; the risk that a subject without an identified pancreatic lesion will, at some point, develop a pancreatic lesion, as well as the risk of that lesion becoming cancerous.

The invention also enables a practitioner to determine the effectiveness of a therapy a subject is undergoing in connection with an identified pancreatic lesion; an increase or decrease in the risk that an identified pancreatic lesion will develop into cancer; an increase or decrease in the likelihood that a subject without an observed pancreatic lesion will develop a pancreatic lesion, and the risk of that lesion becoming cancerous; and a change in an identified pancreatic lesion, including a change in the size, stage, grade, or degree of invasiveness of a cancerous pancreatic lesion.

2. Determination of Hydroxymethylation Profile

Each embodiment of the invention comprises, initially, the generation of a patient's hydroxymethylation profile. The profile is generated by ascertaining the hydroxymethylation level at each of a plurality of hydroxymethylation biomarker loci, and assembling the data so obtained into a data set that serves as the hydroxymethylation profile. The hydroxymethylation biomarkers are differentially hydroxymethylated in subjects who have pancreatic cancer or who are at risk of developing pancreatic cancer, relative to a reference hydroxymethylation profile. That is, the biomarkers comprise regions of genomic DNA that are more susceptible to increases or decreases in hydroxymethylation level than other regions of the DNA, and that exhibit an increase or decrease in hydroxymethylation level in a manner that correlates with pancreatic cancer or a risk of developing pancreatic cancer.

In a first embodiment, the invention provides a method for evaluating the risk that a pancreatic lesion identified on an imaging scan is cancerous. The imaging may be carried out using any suitable method, although cross-sectional imaging is preferred, e.g., using multi-detector row computed tomography (CT) or magnetic resonance imaging (MRI) with MR cholangiopancreatography (MRCP).

The first step in the method involves obtaining a cell-free DNA (cfDNA) sample from a blood sample or cyst fluid sample taken from the patient. Extraction of cfDNA can be carried out using any suitable technique, for example using the commercially available kits referenced in the preceding section. The cfDNA is then enriched, so that the concentration of the cfDNA is substantially increased, a virtual necessity because of the very low levels of cfDNA normally obtained. A generally preferred enrichment technique is described in International Patent Publication WO 2017/176630 to Quake et al., incorporated herein by reference in its entirety: an affinity tag is appended to 5hmC residues in a sample of cfDNA, and the tagged DNA molecules are then selectively removed by bonding to a functionalized solid support. An illustrative example of the method, as described in Quake et al., involves initially modifying end-blunted, adaptor-ligated double-stranded DNA fragments in the cell-free sample to covalently attach biotin, as the affinity tag, to 5hmC residues. This may be carried out by selectively glucosylating 5hmC residues with uridine diphospho (UDP) glucose functionalized at the 6-position with an azide moiety, a step that is followed by a spontaneous 1,3-cycloaddition reaction with alkyne-functionalized biotin via a "click chemistry" reaction. The DNA fragments containing the biotinylated 5hmC residues are adapter-ligated dsDNA template molecules that can then be pulled down with a solid support functionalized with a biotin-binding protein (e.g., avidin or streptavidin) in the enrichment step.

The cfDNA is then amplified without releasing the captured cfDNA from the support, thereby giving a plurality of amplicons. Any suitable amplification technique may be employed (e.g., PCR, NASBA, TMA, SDA) although PCR is preferred.

Next, the nucleic acids that map to each of a plurality of selected loci in a reference hydroxymethylation profile are quantified, so that after amplification, pooling, and sequencing, information regarding hydroxymethylation levels can be deduced from the sequence reads obtained. That is, the sequence reads are analyzed to provide a quantitative determination of which sequences are hydroxymethylated in the cfDNA, and the level of hydroxymethylation. This may be done by, e.g., counting sequence reads or, alternatively, counting the number of original starting molecules, prior to amplification, based on their fragmentation breakpoint and/or whether they contain the same molecular UFI. The use of molecular UFI sequences (or "molecular barcodes" as they are sometimes called) in conjunction with other features of the fragments (e.g., the end sequences of the fragments, which define the breakpoints) to distinguish between the fragments is known. See Casbon (2011) Nucl. Acids Res. 22 e81 and Fu et al. (2011) Proc. Natl. Acad. Sci. USA 108: 9026-31), among others. Molecular barcodes are also described in U.S. Patent Publication Nos. 2015/0044687, 2015/0024950, and 2014/0227705, and in U.S. Pat. Nos. 8,835,358 and 7,537,897, as well as a variety of other publications.

The molecular UFI sequence is preferably incorporated into the adapters that are end-ligated to the cfDNA following extraction thereof. The adapters may be constructed so as to comprise an additional UFI sequence, e.g., a sample UFI sequence, a strand-identifier UFI sequence, or both.

Other methods of ascertaining the hydroxymethylation profile of DNA in the cell-free nucleic sample are described in International Patent Publication WO 2019/160994 A1 to Arensdorf et al. for "Methods for the Epigenetic Analysis of DNA, particularly Cell-Free DNA," and in U.S. Patent Publication No. 2017/0298422 to Song et al., both of which are incorporated by reference herein. These references are also useful in conjunction with an embodiment of the invention in which the present combined workflow process further includes the detection of a cfDNA methylation profile in addition to the cfDNA hydroxymethylation profile.

The selected loci in the above described method are hydroxymethylation biomarkers, i.e., loci that have been identified herein as differentially hydroxymethylated in a manner that relates to the presence, absence, or risk of pancreatic cancer. Certain hydroxymethylation biomarkers that are particularly useful in conjunction with the present methods, as established in Example 1, include, without limitation, those set forth in Table 1 (along with chromosome location):

TABLE 1

| Gene | Location |
|---|---|
| ADARB2-AS1 | chr10 |
| ANKRD36B | chr02 |
| ASAH2B | chr10 |
| ATG4B | chr02 |
| ATP8B1 | chr18 |
| BOLA1 | chr01 |
| C11orf88 | chr11 |
| C17orf97 | chr17 |
| C1orf170 | chr01 |
| C3orf36 | #N/A |
| C8orf74 | chr08 |
| CAMSAP2 | chr01 |
| CCDC54 | chr03 |
| CCDC59 | chr12 |
| CKAP2 | chr13 |
| CLK2P | #N/A |
| CRTC1 | chr19 |
| CSRP2 | chr12 |
| CYB5D1 | chr17 |
| DNAJC27 | #N/A |
| DYNAP | #N/A |
| FAM166A | #N/A |
| FAM188B | chr07 |
| FAM196A | chr10 |
| FAM86JP | #N/A |
| FAT4 | chr04 |
| FBXO5 | chr06 |
| FGF2 | chr04 |
| FUT2 | chr19 |
| GAS2L2 | chr17 |
| GAS6 | #N/A |
| GGACT | chr13 |
| GLRX5 | chr14 |
| GPX1 | #N/A |
| GPX5 | chr06 |
| HBD | chr11 |
| HLA-A | chr06 |
| HTR1F | chr03 |
| IL36G | #N/A |
| KANSL1 | #N/A |
| KCNH6 | #N/A |
| KCTD15 | #N/A |
| KLHL38 | #N/A |
| KLK2 | #N/A |
| KRT6B | chr12 |
| LAMC1 | chr01 |
| LGALS14 | chr19 |
| LGALS8-AS1 | #N/A |
| LIFR | chr05 |
| LINC00266-1 | #N/A |
| LINC00310 | chr21 |
| LOC100130452 | chr02 |
| LOC100130557 | #N/A |
| LOC100130894 | #N/A |
| LOC100288778 | #N/A |
| LOC100505633 | #N/A |
| LOC100505648 | chr15 |
| LOC100505738 | #N/A |
| LOC100652909 | chr19 |

TABLE 1-continued

| Gene | Location |
|---|---|
| LOC389033 | #N/A |
| LOC90784 | #N/A |
| LRRC37A2 | #N/A |
| MED11 | chr17 |
| MRPL23-AS1 | chr11 |
| NAT8L | chr04 |
| NEUROD1 | #N/A |
| NEUROG2 | chr04 |
| NME5 | chr05 |
| NOMO3 | chr16 |
| NPRL2 | chr03 |
| NXN | chr17 |
| ODF3L1 | #N/A |
| ODF3L2 | chr19 |
| OSCP1 | chr01 |
| PARD6G | chr18 |
| PGAM1 | #N/A |
| PLA2G2E | #N/A |
| PLSCR4 | #N/A |
| PPAP2A | chr05 |
| PPP1R15A | chr19 |
| PPP1R3E | #N/A |
| RASL10B | chr17 |
| REXO1L1 | #N/A |
| RIMBP3 | #N/A |
| RNF126P1 | chr17 |
| RNU6-76 | chr16 |
| RPP25 | chr15 |
| RPS27 | #N/A |
| SH3PXD2B | #N/A |
| SHISA4 | #N/A |
| SLC25A38 | #N/A |
| SLC4A1 | #N/A |
| SLCO5A1 | #N/A |
| SPDEF | chr06 |
| SRSF6 | #N/A |
| STRA6 | #N/A |
| SYNM | chr15 |
| TBCB | chr19 |
| TDRD6 | #N/A |
| TEX26 | #N/A |
| TMEM253 | #N/A |
| TNFSF13B | #N/A |
| TTC14 | #N/A |
| TUBA4A | #N/A |
| UBB | chr17 |
| VAMP8 | chr02 |
| VGLL2 | #N/A |
| WASH2P | #N/A |
| WNT9B | #N/A |
| XBP1 | chr22 |
| ZNF789 | #N/A |

While the experimental work documented in Example 1 identified thousands of genes in which 5hmC is differentially expressed, the above group represents a stringently filtered set of the most significant genes using Elastic Net regularization (glmnetF) or Lasso regularization (glmnet2F). The above 111 genes were found to exhibit biology related to pancreatic development (GATA4, GATA6, PROX1, and ONECUT1) and/or cancer development (YAP, TEAD1, PROX, ONECUT1, ONECUT2, IGF1, and IGF2), as explained in Example 1 herein. Table 2 indicates those genes identified using glmnetF and Table 3 indicates those genes identified using glmnet2F:

TABLE 2

| Gene | Location |
|---|---|
| ADARB2-AS1 | chr10 |
| ANKRD36B | chr02 |
| ATG4B | chr02 |
| ATP8B1 | chr18 |

TABLE 2-continued

| Gene | Location |
|---|---|
| BOLA1 | chr01 |
| C11orf88 | chr11 |
| C17orf97 | chr17 |
| C1orf170 | chr01 |
| C3orf36 | #N/A |
| C8orf74 | chr08 |
| CAMSAP2 | chr01 |
| CCDC54 | chr03 |
| CCDC59 | chr12 |
| CKAP2 | chr13 |
| CLK2P | #N/A |
| CRTC1 | chr19 |
| CSRP2 | chr12 |
| CYB5D1 | chr17 |
| DNAJC27 | #N/A |
| DYNAP | #N/A |
| FAM166A | #N/A |
| FAM188B | chr07 |
| FAM196A | chr10 |
| FAM86JP | #N/A |
| FAT4 | chr04 |
| FBXO5 | chr06 |
| FGF2 | chr04 |
| FUT2 | chr19 |
| GAS2L2 | chr17 |
| GAS6 | #N/A |
| GGACT | chr13 |
| GLRX5 | chr14 |
| GPX1 | #N/A |
| GPX5 | chr06 |
| HBD | chr11 |
| HLA-A | chr06 |
| HTR1F | chr03 |
| IL36G | #N/A |
| KANSL1 | #N/A |
| KCNH6 | #N/A |
| KCTD15 | #N/A |
| KLHL38 | #N/A |
| KLK2 | #N/A |
| KRT6B | chr12 |
| LAMC1 | chr01 |
| LGALS14 | chr19 |
| LGALS8-AS1 | #N/A |
| LIFR | chr05 |
| LINC00266-1 | #N/A |
| LINC00310 | chr21 |
| LOC100130557 | #N/A |
| LOC100130894 | #N/A |
| LOC100288778 | #N/A |
| LOC100505633 | #N/A |
| LOC100505648 | chr15 |
| LOC100505738 | #N/A |
| LOC100652909 | chr19 |
| LOC389033 | #N/A |
| LOC90784 | #N/A |
| LRRC37A2 | #N/A |
| MED11 | chr17 |
| MRPL23-AS1 | chr11 |
| NAT8L | chr04 |
| NEUROD1 | #N/A |
| NEUROG2 | chr04 |
| NME5 | chr05 |
| NOMO3 | chr16 |
| NPRL2 | chr03 |
| NXN | chr17 |
| ODF3L1 | #N/A |
| ODF3L2 | chr19 |
| OSCP1 | chr01 |
| PARD6G | chr18 |
| PGAM1 | #N/A |
| PLA2G2E | #N/A |
| PLSCR4 | #N/A |
| PPAP2A | chr05 |
| PPP1R15A | chr19 |
| PPP1R3E | #N/A |
| RASL10B | chr17 |
| REXO1L1 | #N/A |
| RIMBP3 | #N/A |

TABLE 2-continued

| Gene | Location |
|---|---|
| RNF126P1 | chr17 |
| RNU6-76 | chr16 |
| RPP25 | chr15 |
| RPS27 | #N/A |
| SH3PXD2B | #N/A |
| SHISA4 | #N/A |
| SLC25A38 | #N/A |
| SLC4A1 | #N/A |
| SLCO5A1 | #N/A |
| SPDEF | chr06 |
| SRSF6 | #N/A |
| STRA6 | #N/A |
| SYNM | chr15 |
| TBCB | chr19 |
| TDRD6 | #N/A |
| TEX26 | #N/A |
| TMEM253 | #N/A |
| TNFSF13B | #N/A |
| TTC14 | #N/A |
| TUBA4A | #N/A |
| UBB | chr17 |
| VAMP8 | chr02 |
| VGLL2 | #N/A |
| WASH2P | #N/A |
| WNT9B | #N/A |
| XBP1 | chr22 |
| ZNF789 | #N/A |

TABLE 3

| Gene | Location |
|---|---|
| ASAH2B | chr10 |
| BOLA1 | chr01 |
| C11orf88 | chr11 |
| C17orf97 | chr17 |
| C3orf36 | #N/A |
| CCDC54 | chr03 |
| CKAP2 | chr13 |
| CLK2P | #N/A |
| DNAJC27 | chr02 |
| DYNAP | #N/A |
| FAM166A | chr09 |
| FGF2 | chr04 |
| FUT2 | chr19 |
| GAS6 | #N/A |
| GGACT | chr13 |
| GPX1 | #N/A |
| GPX5 | chr06 |
| IL36G | #N/A |
| KCNH6 | chr17 |
| KCTD15 | chr19 |
| KLK2 | #N/A |
| KRT6B | chr12 |
| LGALS14 | chr19 |
| LGALS8-AS1 | #N/A |
| LIFR | chr05 |
| LINC00266-1 | #N/A |
| LINC00310 | chr21 |
| LOC100130452 | chr02 |
| LOC100130557 | #N/A |
| LOC100288778 | #N/A |
| LOC100505648 | chr15 |
| MED11 | chr17 |
| NAT8L | chr04 |
| NEUROG2 | chr04 |
| NME5 | chr05 |
| NOMO3 | chr16 |
| NPRL2 | chr03 |
| NXN | chr17 |
| ODF3L1 | #N/A |
| PPP1R3E | #N/A |
| RASL10B | chr17 |
| RNF126P1 | chr17 |
| SH3PXD2B | chr05 |

TABLE 3-continued

| Gene | Location |
|---|---|
| SLC25A38 | chr03 |
| TNFSF13B | chr13 |
| VAMP8 | chr02 |
| VGLL2 | #N/A |

Other hydroxymethylation biomarkers that are useful in conjunction with the present methods are the 611 genes set forth in FIG. 21, along with location and glmnet value (identified using Study Group 2 in Example 2). Hydroxymethylation biomarkers within this group that may be of particular interest are the 41 biomarkers set forth in Table 4, again along with location and glmnet value (from Study Group 3 in Example 3)

TABLE 4

| Gene | Location | Glmnet |
|---|---|---|
| LINC00457 | chr13~-~35009590~35214822~ | 100 |
| CERS3 | chr15~-~100940599~101084925~ | 67 |
| LOC285629 | chr05~-~160358785~160365633~ | 65 |
| RHOJ | chr14~+~63671101~63760230~ | 57 |
| GP2 | chr16~-~20321810~20338835~ | 56 |
| SFRP1 | chr08~-~41119475~41166990~ | 56 |
| LY6G6F | chr06~+~31674683~31678372~ | 51 |
| HOXA4 | chr07~-~27168125~27170399~ | 50 |
| MYOCD | chr17~+~12569206~12670651~ | 46 |
| C14orf64 | chr14~-~98391946~98444461~ | 45 |
| PDE10A | chr06~-~165740775~166075588~ | 42 |
| PTCRA | chr06~+~42883726~42893575~ | 42 |
| UCP3 | chr11~-~73711325~73720282~ | 41 |
| NTRK2 | chr09~+~87283465~87638505~ | 36 |
| GABRGR3 | chr15~+~27216428~27778373~ | 33 |
| FBXL7 | chr05~+~15500304~15939900~ | 31 |
| LOC100128714 | chr15~+~26147506~26298267~ | 23 |
| LOC151171 | chr02~-~239419330~239464140~ | 23 |
| MIR5009 | chr21~-~28659821~29283529~ | 20 |
| HKR1 | chr19~+~37825579~37855357~ | 17 |
| ZNF573 | chr19~-~38229202~38270230~ | 16 |
| LINC00670 | chr17~+~12453284~12540504~ | 16 |
| FILIP1 | chr06~-~76017799~76203496~ | 16 |
| DCLK1 | chr13~-~36342788~36705514~ | 15 |
| OSGEP | chr14~-~20915206~20923267~ | 13 |
| BNC2 | chr09~-~16409500~16870786~ | 12 |
| ABCC12 | chr16~-~48116883~48180681~ | 11 |
| PCDH7 | chr04~+~30722029~31148423~ | 10 |
| ZNF2 | chr02~+~95831182~95850064~ | 10 |
| PDLIM1 | chr10~-~96997324~97050905~ | 9 |
| TSPAN33 | chr07~+~128784711~128809534~ | 9 |
| MRPS5 | chr02~-~95752951~95787754~ | 8 |
| C15orf53 | chr15~+~38988798~38992239~ | 7 |
| CAMK1G | chr01~+~209757044~209787284~ | 7 |
| TWIST2 | chr02~+~239756672~239832237~ | 6 |
| FGF9 | chr13~+~22245214~22278640~ | 5 |
| CCDC129 | chr07~+~31553684~31698334~ | 5 |
| ISLR2 | chr15~+~74421714~74429143~ | 4 |
| C17orf51 | chr17~-~21431570~21454941~ | 2 |
| ADAMTS9-AS2 | chr03~+~64670545~64997143~ | 2 |
| GABRA5 | chr15~+~27111865~27194357~ | 1 |

Also see FIG. 22, which provides detailed information regarding the 41 hydroxymethylation biomarkers of Table 4.

One preferred method for detecting the hydroxymethylation profile of a nucleic acid is described in International Patent Publication WO 2017/176630 to Quake et al., incorporated herein by reference in its entirety. That method pertains to the detection of 5-hydroxymethylcytosine patterns in cell-free DNA within the context of a sequencing scheme. An affinity tag is appended to 5hmC residues in a sample of cell-free DNA, and the tagged DNA molecules are then enriched and sequenced, with 5hmC locations identified. An illustrative example of the method, as described in Quake et al., involves initially modifying end-blunted, adaptor-ligated double-stranded DNA fragments in the cell-free sample to covalently attach biotin, as the affinity tag, to 5hmC residues. This may be carried out by selectively glucosylating 5hmC residues with uridine diphospho (UDP) glucose functionalized at the 6-position with an azide moiety, a step that is followed by a spontaneous 1,3-cycloaddition reaction with alkyne-functionalized biotin via a "click chemistry" reaction, as described previously, in Section 5, with respect to 5hmC-containing capture sequences in adapters. The DNA fragments containing the biotinylated 5hmC residues are adapter-ligated dsDNA template molecules that can then be pulled down with streptavidin beads in an "enrichment" step.

Both targeted and non-sequencing detection approaches after enrichment may also be used to quantitate specific hydroxymethylation biomarkers and loci of interest, if genome-wide coverage through shotgun sequencing is not required or desirable (generally for cost reasons). For example, after 5hmC enrichment, targeted PCR amplicons covering only specific regions may be generated from the 5hmC-enriched templates and employed as a more narrow genome coverage approach, and used as input to sequencing or detected directly.

When a smaller number of discrete loci are of interest, the combination of these post-enrichment approaches with target amplification may also be an efficient way to reduce the number of sequencing reads (and sequencing costs) required for each sample, enabling further sample multiplexing per sequencing run and further reducing the sequencing costs required for each sample). In non-sequencing approaches, quantitative PCR or even hybridization assays could themselves be used as the quantitative readouts of the hydroxymethylation biomarkers (e.g., using direct fluorescence nucleotide labeling and microarray or other substrate capture and binding); such approaches are well known in the art, and frequently scaled to hundreds or even thousands of short amplicons.

In the present process, a 5hmC UFI sequence is added to the termini of the pulled down adapter-ligated dsDNA template molecules, so that the after amplification, pooling, and sequencing, information regarding hydroxymethylation profile can be deduced from the sequence reads obtained. That is, the sequence reads are analyzed to provide a quantitative determination of which sequences are hydroxymethylated in the cfDNA. This may be done by, e.g., counting sequence reads or, alternatively, counting the number of original starting molecules, prior to amplification, based on their fragmentation breakpoint and/or whether they contain the same molecular UFI. The use of molecular UFI sequences (or "molecular barcodes" as they are sometimes called) in conjunction with other features of the fragments (e.g., the end sequences of the fragments, which define the breakpoints) to distinguish between the fragments is known. See Casbon (2011) *Nucl. Acids Res.* 22 e81 and Fu et al. (2011) *Proc. Natd. Acad. Sci. USA* 108: 9026-31), among others. Molecular barcodes are also described in U.S. Patent Publication Nos. 2015/0044687, 2015/0024950, and 2014/0227705, and in U.S. Pat. Nos. 8,835,358 and 7,537,897, as well as a variety of other publications.

Other methods of ascertaining the hydroxymethylation profile of DNA in the cell-free nucleic sample are described in International Patent Publication WO 2019/160994 A1 to Arensdorf et al. for "Methods for the Epigenetic Analysis of DNA, particularly Cell-Free DNA" and in U.S. Patent Publication No. 2017/0298422 to Song et al., both of which are incorporated by reference herein. These references are also useful in conjunction with an embodiment of the invention in which the present combined workflow process further includes the detection of a cfDNA methylation profile in addition to the cfDNA hydroxymethylation profile.

The Arensdorf et al. methodology described in WO 2019/160994, in the context of the present combined workflow process, can be implemented as follows:

Dual-Biotin Technique: After a cell-free nucleic acid sample has been extracted from a biological sample, with cfDNA having been adapter-ligated, 5hmC residues in the cfDNA are selectively labeled with an affinity tag, e.g., a biotin moiety as explained earlier herein. Biotinylation can be carried out by selective functionalization of 5hmC residues via PGT-catalyzed glucosylation with uridine diphosphoglucose-6-azide followed by a click chemistry reaction to covalently attach an alkyne-functionalized biotin moiety as explained previously. An avidin or streptavidin surface (e.g., in the form of streptavidin beads) is then used to pull out all of the dsDNA template molecules biotinylated at the 5hmC locations, which are then placed in a separate container for UFI sequence attachment during amplification. The remaining dsDNA template molecules in the supernatant are fragments that either have 5mC residues or have no modifications (the latter group including cDNA generated from cfRNA). A TET protein is then used to oxidize 5mC residues in the supernatant to 5hmC; in this case, a TET mutant protein is employed to ensure that oxidation of 5mC does not proceed beyond hydroxylation. Suitable TET mutant proteins for this purpose are described in Liu et al. (2017) *Nature Chem. Bio.* 13: 181-191, incorporated by reference herein. The PGT-catalyzed glucosylation followed by biotin functionalization is then repeated. The fragments so marked—biotinylated at each of the original 5mC locations—are pulled down with streptavidin beads. The bead-bound DNA fragments are then barcoded—with a UFI sequence than used in the first step, i.e., a 5mC UFI sequence—during amplification. Unmodified DNA fragments, i.e., fragments containing no modified cytosine residues, now remain in the supernatant. If desired, sequence-specific probes can be used to hybridize to unmethylated DNA strands. The hybridized complexes that result can be pulled out and tagged with a further UFI sequence during amplification, as before.

Pic-Borane Methodology: This is an alternative to the dual biotin technique, and also begins with biotinylation of 5hmC residues in adapter-ligated DNA fragments, followed by avidin or streptavidin pull-down. In this technique, however, the DNA containing unmodified 5mC residues remaining in the supernatant is oxidized beyond 5hmC, to 5caC and/or 5fC residues. Oxidation may be carried out enzymatically, using a catalytically active TET family enzyme. A "TET family enzyme" or a "TET enzyme" as those terms are used herein refer to a catalytically active "TET family protein" or a "TET catalytically active fragment" as defined in U.S. Pat. No. 9,115,386, the disclosure of which is incorporated by reference herein. A preferred TET enzyme in this context is TET2; see Ito et al. (2011) *Science* 333(6047):1300-1303. Oxidation may also be carried out chemically, using a chemical oxidizing agent. Examples of suitable oxidizing agent include, without limitation: a perruthenate anion in the form of an inorganic or organic perruthenate salt, including metal perruthenates such as potassium perruthenate ($KRuO_4$), tetraalkylammonium perruthenates such as tetrapropylammonium perruthenate (TPAP) and tetrabutylammonium perruthenate (TBAP), and polymer supported perruthenate (PSP); and inorganic peroxo compounds and compositions such as peroxotungstate or a copper (II) perchlorate/TEMPO combination. It is unnecessary at this point to separate 5fC-containing fragments from 5caC-containing fragments, insofar as in the next step of the process, both 5fC residues and 5caC residues are converted to dihydrouracil (DHU).

That is, following oxidation of 5mC residues to 5fC and 5caC, an organic borane is added to reduce, deaminate, and either decarboxylate or deformylates the oxidized 5mC residues. The resulting dsDNA template molecules contain DHU in place of the original 5mC residues, and can be amplified, pooled, and sequenced, along with other dsDNA template molecules deriving from the same sample.

The organic borane may be characterized as a complex of borane and a nitrogen-containing compound selected from nitrogen heterocycles and tertiary amines. The nitrogen heterocycle may be monocyclic, bicyclic, or polycyclic, but is typically monocyclic, in the form of a 5- or 6-membered ring that contains a nitrogen heteroatom and optionally one or more additional heteroatoms selected from N, O, and S. The nitrogen heterocycle may be aromatic or alicyclic. Preferred nitrogen heterocycles herein include 2-pyrroline, 2H-pyrrole, 1H-pyrrole, pyrazolidine, imidazolidine, 2-pyrazoline, 2-imidazoline, pyrazole, imidazole, 1,2,4-triazole, 1,2,4-triazole, pyridazine, pyrimidine, pyrazine, 1,2,4-triazine, and 1,3,5-triazine, any of which may be unsubstituted or substituted with one or more non-hydrogen substituents. Typical non-hydrogen substituents are alkyl groups, particularly lower alkyl groups, such as methyl, ethyl, n-propyl, isopropyl, n-butyl, isobutyl, t-butyl, and the like. Exemplary compounds include pyridine borane, 2-methylpyridine borane (also referred to as 2-picoline borane), and 5-ethyl-2-pyridine. Further information concerning these organic boranes and reaction thereof to convert oxidized 5mC residues to DHU may be found in the Arensdorf patent publication cited above.

Biotin/Native 5mC Enrichment Method: This is an alternative to the dual biotin technique, and begins with biotinylation of 5hmC residues in adapter-ligated DNA fragments, followed by avidin or streptavidin pull-down. Here, however, instead of modifying the methylated DNA that remains in the supernatant, an anti-5mC antibody or an MBD protein is used to capture and pull down native 5mC-containing fragments. This technique is less preferred herein, insofar as it does not result in the generation of dsDNA template molecules that can be amplified, pooled, and sequenced with other dsDNA template molecules deriving from the same sample.

3. Methods of Use

As explained in the preceding section, the invention, in one embodiment, provides a method for predicting the risk that a patient with an identified pancreatic lesion has pancreatic cancer. Also provided are diagnostic, prognostic, and predictive uses of hydroxymethylation profiles, as well as uses in patient monitoring, evaluation of treatment options, and evaluation of treatment efficacy, wherein, in each method of use, the hydroxymethylation profile generated is combined with clinical parameters and optionally with one or more other risk factors in each method of use. All of the methods involve the generation of a hydroxymethylation profile comprising measurements of hydroxymethylation levels at each of a plurality of hydroxymethylation biomarker loci.

Among the provided diagnostic, prognostic, and predictive methods are those which employ statistical analysis and biomathematical algorithms and predictive models to analyze the detected hydroxymethylation information. Some embodiments include methods and systems for analyzing the hydroxymethylation information in classification, staging, prognosis, treatment design, evaluation of treatment options, prediction of outcomes (e.g., predicting development of metastases), and the like.

Also provided are methods that use evaluation of hydroxymethylation levels at the biomarker loci in treatment development and patient monitoring, including evaluation of a patient's response to treatment and patient-specific or individualized treatment strategies. In some embodiments, the methods are used in conjunction with treatment, for example, by generating a hydroxymethylation profile weekly or monthly before and/or after treatment. As the hydroxymethylation levels at certain biomarker loci correlate with the progression of disease, ineffectiveness or effectiveness of treatment, and/or the recurrence or lack thereof of disease, the regular generation of hydroxymethylation profiles within an extended monitoring or treatment period is useful. In some aspects, the information obtained may indicate that a different treatment strategy is preferable. Thus, provided herein are therapeutic methods, in which biomarker evaluation is performed prior to treatment, and then used to monitor therapeutic effects.

More specifically, at various points in time after initiating or resuming treatment, significant changes in hydroxymethylation levels at one or more of the biomarker loci may be seen, indicating that a therapeutic strategy is or is not successful, that disease is recurring, or that a different therapeutic approach should be used. In some embodiments, the therapeutic strategy is changed following a hydroxymethylation analysis, such as by adding a different therapeutic intervention, either in addition to or in place of a prior approach, by increasing or decreasing the aggressiveness or frequency of the approach, or by stopping or reinstituting a treatment regimen.

In another aspect, the hydroxymethylation levels at each of the biomarker loci are used to identify the presence of pancreatic cancer or a risk of developing pancreatic cancer for the first time.

In some aspects, the methods determine whether or not the assayed patient is responsive to treatment, such as a subject who is clinically categorized as in complete remission or exhibiting stable disease. In some aspects, methods are provided for distinguishing treatment-responsive and non-responsive patients, and for distinguishing patients with stable disease or those in complete remission, and those with progressive disease.

In various aspects, the methods and systems make such calls with at least at or about 65, 70, 75, 80, 81, 82, 83, 84, 85, 86, 87, 88, 89, 90, 91, 92, 93, 94, 95, 96, 97, 98, 99, or 100% correct call rate (i.e., accuracy), specificity, or sensitivity.

All of the aforementioned methods are encompassed by the present invention. Preferred methods herein include, without limitation:

a method for evaluating the risk that an identified pancreatic lesion in a patient is cancerous;

a method for monitoring an identified pancreatic lesion in a patient, which involves an analysis of hydroxymethylation changes over time;

a method for managing a patient with an identified pancreatic lesion, which involves an evaluation of treatment options based on a hydroxymethylation profile;

a method for monitoring the effectiveness of treatment in a patient with an identified pancreatic lesion, which involves an analysis of hydroxymethylation profiles generated at selected time intervals within an extended monitoring period;

a method for reducing unnecessary surgical resection of a pancreatic lesion by evaluating the risk that the pancreatic lesion is cancerous using a hydroxymethylation profile; and a method for identifying the risk that a patient without an identified pancreatic lesion will develop pancreatic cancer.

4. Statistical Analyses, Mathematical Algorithms and Predictive Models

Typically, the methods of the invention include statistical analysis and mathematical modeling used to analyze high-dimensional and multimodal biomedical data, such as the data obtained using the present methods for generating and comparing hydroxymethylation profiles. More specifically, the methods make use of one or more objective algorithms, models, and analytical methods that include mathematical analyses based on topographic, pattern-recognition based protocols, e.g., support vector machines (SVM), linear discriminant analysis (LDA), naive Bayes (NB), and K-nearest neighbor (KNN) protocols, as well as other supervised learning algorithms and models, such as Decision Tree, Perceptron, and regularized discriminant analysis (RDA), and similar models and algorithms well-known in the art (Gallant S I, "Perceptron-based learning algorithms," Perceptron-based learning algorithms 1990; 1(2):179-91).

Statistical analyses include determining mean (M), e.g., geometric mean, standard deviations (SD), Geometric Fold Change (FC), and the like. Whether differences in hydroxymethylation levels are deemed significant may be determined by well-known statistical approaches, typically by designating a threshold for a particular statistical parameter, such as a threshold p-value (e.g., $p<0.05$), a threshold S-value (e.g., ±0.4, with $S\leq-0.4$ or $S>0.4$), or other value, at which differences are deemed significant, for example when the level of biomarker hydroxymethylation in a hydroxymethylation profile is considered significantly increased or decreased, respectively, relative to the hydroxymethylation level at the same hydroxymethylation biomarker locus in a reference hydroxymethylation profile.

In one aspect, the methods of the invention apply the mathematical formulations, algorithms or models to distinguish between normal and cancerous samples, and between various sub-types, stages, and other aspects of disease or disease outcome. In another aspect, the methods are used for prediction, classification, prognosis, and treatment monitoring and design.

For the comparison of hydroxymethylation levels or other values, data are compressed. Compression typically is by Principal Component Analysis (PCA) or a similar technique for visualizing the structure of high-dimensional data. PCA is used to reduce dimensionality of the data (e.g., measured expression values) into uncorrelated principal components (PCs) that explain or represent a majority of the variance in the data, such as about 50, 60, 70, 75, 80, 85, 90, 95 or 99% of the variance. PCA allows the visualization of biomarker levels and the comparison of hydroxymethylation profiles, such as between normal or reference samples and test samples. PCA mapping, e.g., 3-component PCA mapping is used to map data to a three-dimensional space for visualization, such as by assigning first, second, and third PCs to the x-, y- and z-axes, respectively.

In some embodiments, there is a linear correlation between hydroxymethylation levels of two or more biomarkers. Pearson's Correlation (PC) coefficients may be used to assess linear relationships (correlations) between pairs of values, such as between hydroxymethylation levels of a biomarker. This analysis may be used to linearly separate distribution in expression patterns, by calculating PC coefficients for individual pairs of the biomarkers (plotted on x- and y-axes of individual Similarity Matrices). Thresholds may be set for varying degrees of linear correlation, such as a threshold for highly linear correlation of (R.sup.2>0.50, or 0.40). Linear classifiers can be applied to the datasets. In one example, the correlation coefficient is 1.0.

In some embodiments, Feature Selection (FS) is applied to remove the most redundant features from a dataset, such as a hydroxymethylation biomarker dataset. FS enhances the generalization capability, accelerates the learning process, and improves model interpretability. In one aspect, FS is employed using a "greedy forward" selection approach, selecting the most relevant subset of features for the robust learning models. (Peng H, Long F, Ding C, "Feature selection based on mutual information: criteria of max-dependency, max-relevance, and min-redundancy," IEEE Transactions on Pattern Analysis and Machine Intelligence, 2005; 27(8):1226-38). In some embodiments, SVM algorithms are used for classification of data by increasing the margin between the n data sets (Cristianini N, Shawe-Taylor J. An Introduction to Support Vector Machines and other kernel-based learning methods. Cambridge: Cambridge University Press, 2000).

Analytic classification of the hydroxymethylation biomarkers herein can be made according to predictive modeling methods that set a threshold for determining the probability that a sample (e.g., a cfDNA sample obtained from a patient) belongs to a given class (e.g., elevated risk of developing pancreatic cancer). The probability preferably is at least 50%, or at least 60%, or at least 70%, or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUROC (area under the ROC curve) or accuracy, of a particular value, or range of values. Area under the curve measures are useful for comparing the accuracy of a classifier across the complete data range. Classifiers with a greater AUC have a greater capacity to classify unknowns correctly between two groups of interest. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be adjusted to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about 0.7, at least about 0.75, at least about 0.8, at least about 0.85, at least about 0.9, at least about 0.95, at least about 0.98, at least about 0.99, or higher.

Raw data can be initially analyzed by measuring the hydroxymethylation level for each biomarker. The data can be manipulated, for example, raw data can be transformed using standard curves, and the average of multiple measurements, if made, can be used to calculate the average and standard deviation for each patient. The data are then input into a selected predictive model, which will classify the sample. The resulting information can be communicated to a patient or health care provider, usually in the form of a written report.

To generate a predictive model for pancreatic cancer, a robust data set, comprising known control samples and samples corresponding to pancreatic cancer, is used in a training set. A sample size can be selected using generally accepted criteria. As discussed above, different statistical methods can be used to obtain a highly accurate predictive model. The examples herein provide representative such analyses.

In one embodiment, hierarchical clustering is performed in the derivation of a predictive model, where the Pearson correlation is employed as the clustering metric. One approach is to consider a dataset as a "learning sample" in a problem of "supervised learning." CART is a standard in applications to medicine (Singer, *Recursive Partitioning in the Health Sciences* (Springer, 1999)) and can be modified by transforming any qualitative features to quantitative features, sorting them by attained significance levels, and a selected regularization method then applied (e.g., Elastic Net or Lasso).

In some embodiments, the predictive models include Decision Tree, which maps observations about an item to a conclusion about its target value (Zhang et al., "*Recursive Partitioning in the Health Sciences*," in Statistics for Biology and Health (Springer, 1999.). The leaves of the tree represent classifications and branches represent conjunctions of features that devolve into the individual classifications.

The predictive models and algorithms may further include Perceptron, a linear classifier that forms a feed forward neural network and maps an input variable to a binary classifier (Gallant (1990), "Perceptron-based learning algorithms," in *IEEE Transactions on Neural Networks* 1(2): 179-191). In this model, the learning rate is a constant that regulates the speed of learning. A lower learning rate improves the classification model, while increasing the time to process the variable (Markey et al. (2002) *Comput Biol Med* 32(2):99-109).

These and other aspects of the invention are further described and illustrated by way of the following examples.

Example 1

(a) Study Design and Clinical Cohort:

Plasma specimens from subjects without or with pancreatic ductal adenocarcinoma were collected at multiple institutions in different geographic regions of the United States and Germany. This study group, Study Group 1, included 41 PDAC patients and 51 non-cancer subjects. These PDAC and non-cancer patient samples satisfied the study inclusion criteria, which included a minimum subject age of 18 years as well as confirmed pathologic diagnosis of adenocarcinoma of any subtype at the time of surgical resection, for subjects in the cancer cohort. The non-cancer cohort was identified as satisfying the study inclusion criteria and patients were specifically negative for any form of cancer. Neither cohort was being treated with medication for disease at the time of blood collection. There were no statistically significant differences in subject age or gender between the two cohorts, but there was a statistically significant greater tobacco exposure in the PDAC cohort, as expected given smoking is a common risk factor for pancreatic cancer. The clinical characteristics of the cancer and non-cancer cohorts are set forth in Table 5:

TABLE 5

| | No Cancer | Cancer |
|---|---|---|
| Age+ | | |
| | 66.0 | 71.2 |
| Gender(%) | | |
| Male | 60.0 | 45.1 |
| Smoking History Status(%) | | |
| Current | 19.5 | 19.6 |
| Former | 29.3 | 37.3 |
| None | 51.2 | 43.1 |
| Pack-Years+ | | |
| Current | 5.3 | 29.6 |
| Former | 20.5 | 24.2 |
| None | NA | NA |
| Pack-Years+ | | |
| All | 14.4 | 25.7 |
| Time Since Cessation+ | | |
| Months | 264.2 | 272.3 |
| Stage | | |
| I | NA | 18 |
| II | NA | 61 |
| III | NA | 7.8 |
| IV | NA | 14 |

+mean of Non-Cancer and Cancer

Other values are percentages of each category in the Non-Cancer and Cancer groups.

(b) Sequencing Results and Metrics:

5hmC-enriched libraries were prepared using the cell-free "5hmC-Seal" method described in International Patent Publication WO 2017/176630 to Quake et al., Song et al. (2011) 29: 68-72, and Han et al. (2016) Mol. Cell 63:711-19, the disclosures of which are incorporated by reference herein. Briefly, hMe-Seal is a low-input, whole-genome cell-free 5hmC sequencing method based on selective chemical labeling, in which β-glucosyltransferase is used to selectively label 5hmC with a biotin moiety via an azide-modified glucose for pull-down of 5hmC-containing DNA fragments for sequencing. In implementing hMe-Seal in the present case, the cfDNA was first ligated with sequencing adapters, followed by selective labeling of 5hmC with j-GT, and affinity enrichment via selective pull-down of DNA fragments containing biotin-labeled 5hmC using streptavidin beads. PCR was then carried out directly from the beads (i.e., instead of eluting the captured DNA) to minimize sample loss during purification. A median number of unique read pairs of 9.1 and 10.7 million in the PDAC and non-cancer cohorts, respectively, were produced. Filtering criteria to enable the determination of high quality 5hmC libraries were established from previous studies (Fonseca et al. (2018), supra), yielding 51 in the pancreatic cancer group and 41 in the non-cancer group. Extensive analysis did not reveal batch processing effects occurring specifically in either study cohort.

Figure 3:
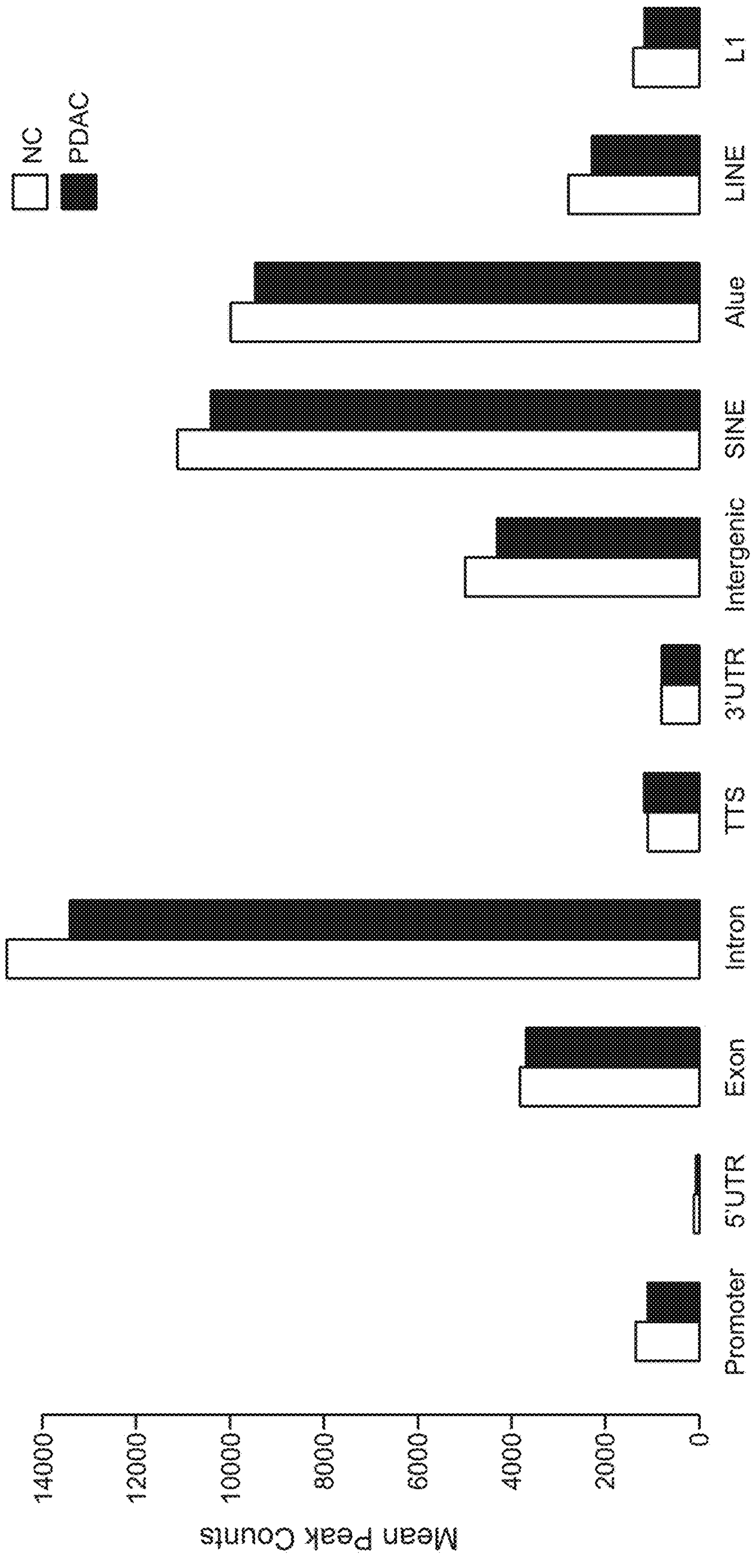
FIG. 3 is a histogram showing the mean peak counts of 5hmC loci across distinct genomic regions, for the two cohorts, PDAC and non-cancer (identified in the figures as "PDAC" and "NC," respectively. It may be seen that non-coding features have a larger number of peaks.
Figure 5:
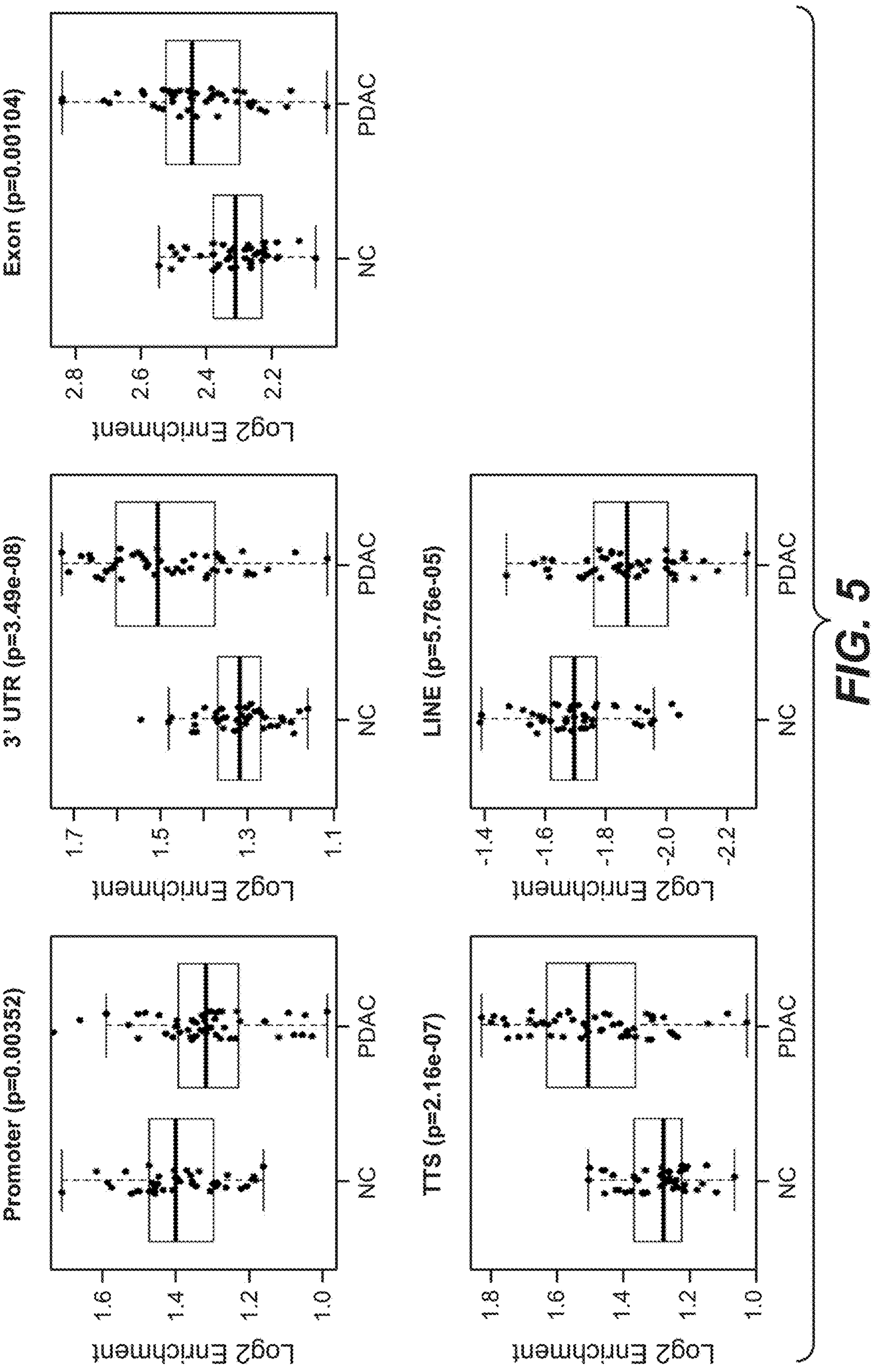
FIG. 5 provides box plots depicting statistically significant changes of 5hmC peaks in pancreatic cancer samples relative to non-cancer samples, in the promoter, LINE elements, exons, 3'UTR, and translation termination sites; here, the Y-axis value equal to log 2 (cancer/non-cancer). Promoter and LINE elements were found to exhibit a depletion of 5-hydroxymethylcytosine (i.e., a decrease in hydroxymethylation) in the cancer (PDAC) samples relative to the non-cancer samples, while 5hmC enrichment was observed in exons, 3'UTR, and translation termination sites. In each box plot herein, the line within the box represents the median of the data, while the lower limit of the box represents the lower quartile and the upper limit of the box represents the upper quartile. Normally distributed data are portrayed as an aligned dot plot with error bars representing standard deviation from the mean. The calculated p-values are provided above each plot.
Figure 6:
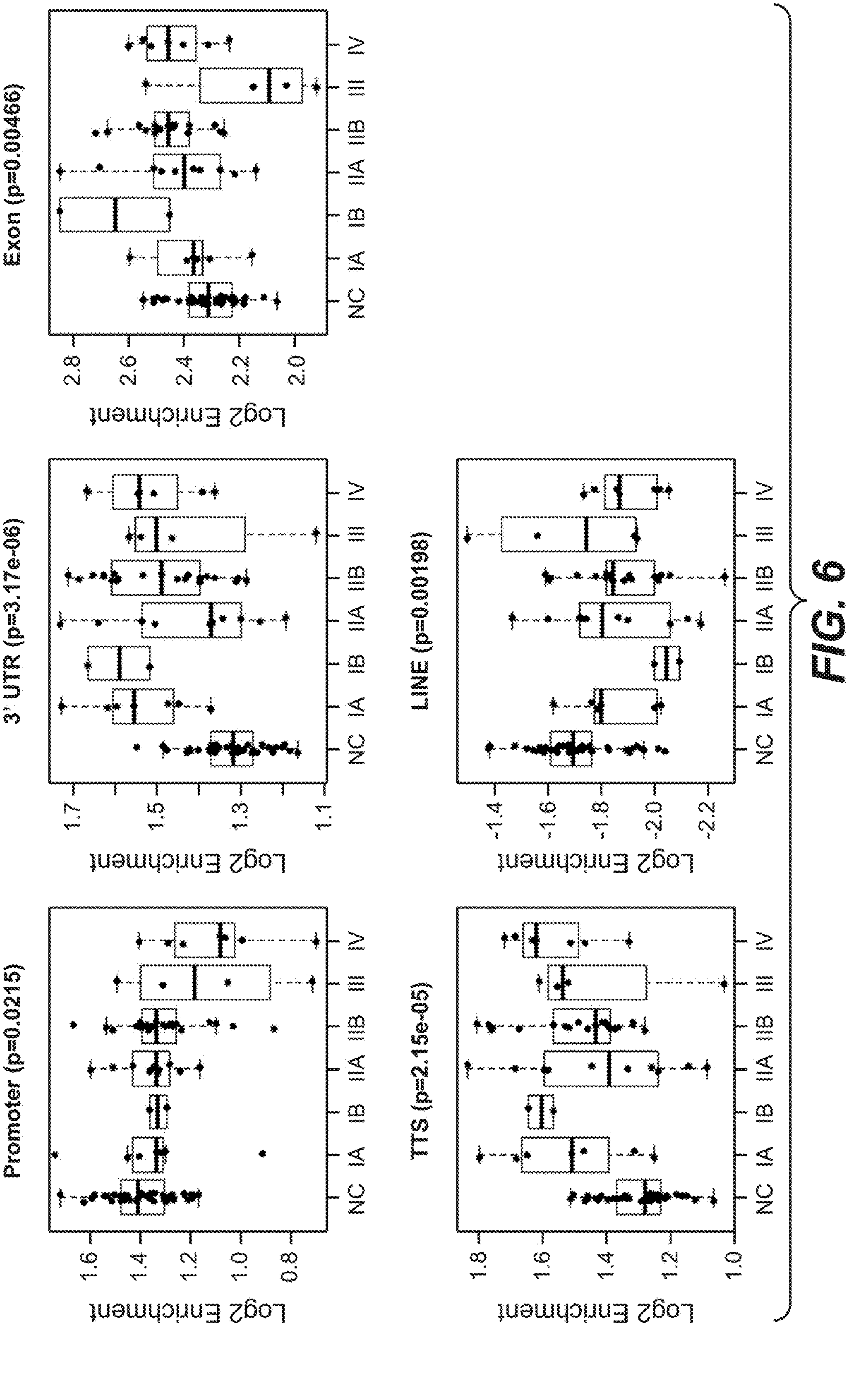
FIG. 6 provides box plots depicting statistically significant changes of 5hmC peaks in functional regions across pancreatic stages.

(c) Cohort-Based Distributions of 5hmC Densities into Functional Regions:

The vast majority of 5hmC loci, as measured by increased read density and detected by MACS2 as peaks, were found to occur, on average, in non-coding, intragenic regions of the genome, i.e., intronic, transposon repeats—SINEs and LINEs, and intergenic, as illustrated in FIG. 3, with no preferential 5hmC distribution in any one disease cohort. These regions displayed low 5hmC enrichment (intron, FIG. 4) or even depletion of 5hmC sites (intergenic and LINE elements, FIG. 4). Instead, 5hmC enrichment occurred more frequently in promoters, UTRs, exons, transcription termination sites (TTS) and SINE elements as measured relative to the genome background. Significant differences in the enrichment of 5hmC peaks in functional regions were observed in a disease cohort specific manner. Increases in enrichment in PDAC were measured in exons, 3'UTR, and TTS, whereas decreases were found in promoter and LINEs, which themselves were either 5hmC-enriched or 5hmC-depleted, respectively (FIG. 5). These global changes were found to occur in a statistically significant manner in each cohort and were also found to occur in a cancer stage specific manner, with gradual increases (exon, 3'UTR and TTS) or decreases (promoter and LINE) in later stage patients (FIG. 6).

Figure 7:
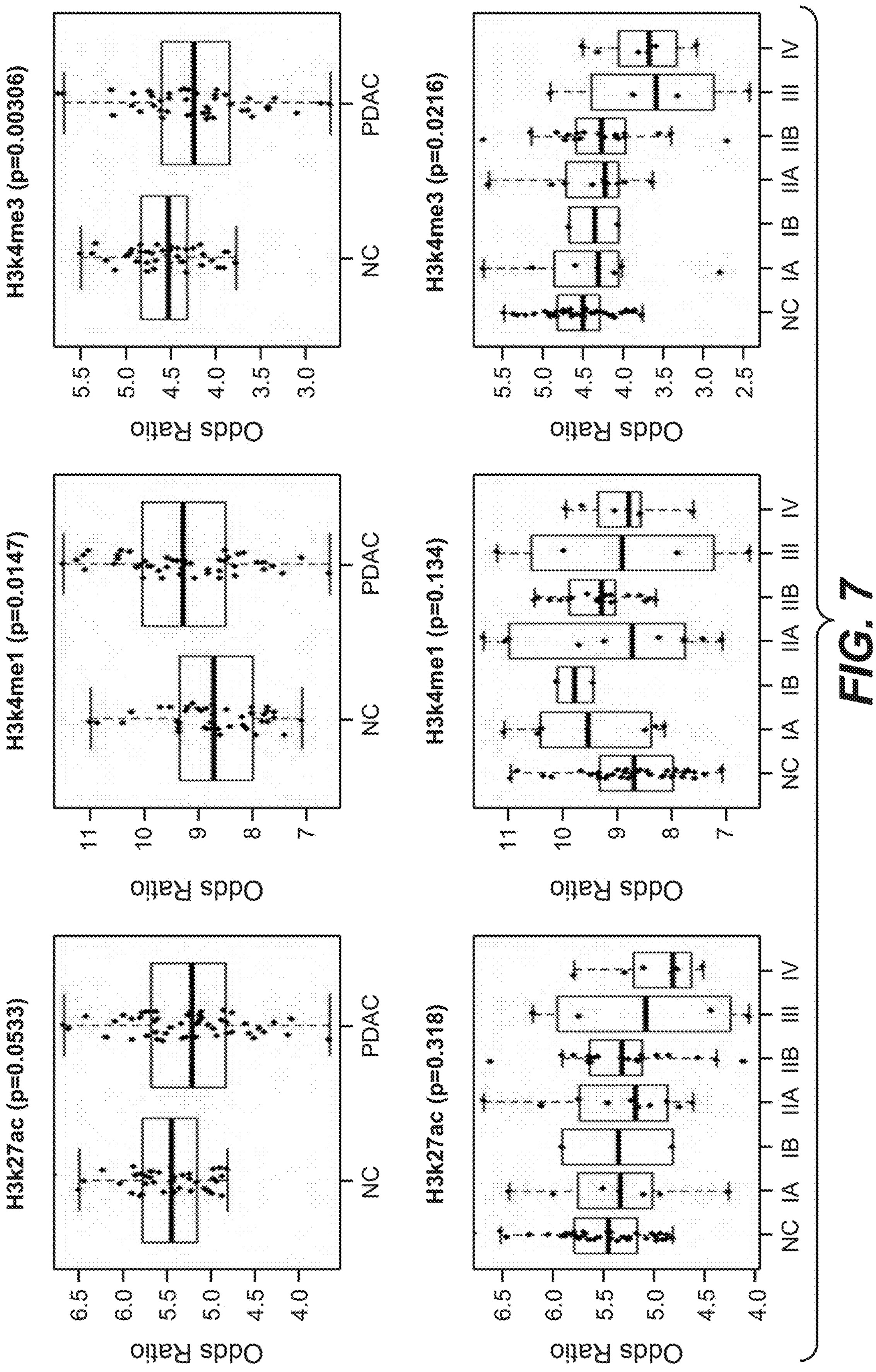
FIG. 7 provides box plots depicting 5hmC peak depletion in H3K4me3 and H3K27ac histone marks in the PDAC cohort (top panel) and ongoing H3K4me3 depletion observed in later stage disease (bottom panel).
Figure 8A:
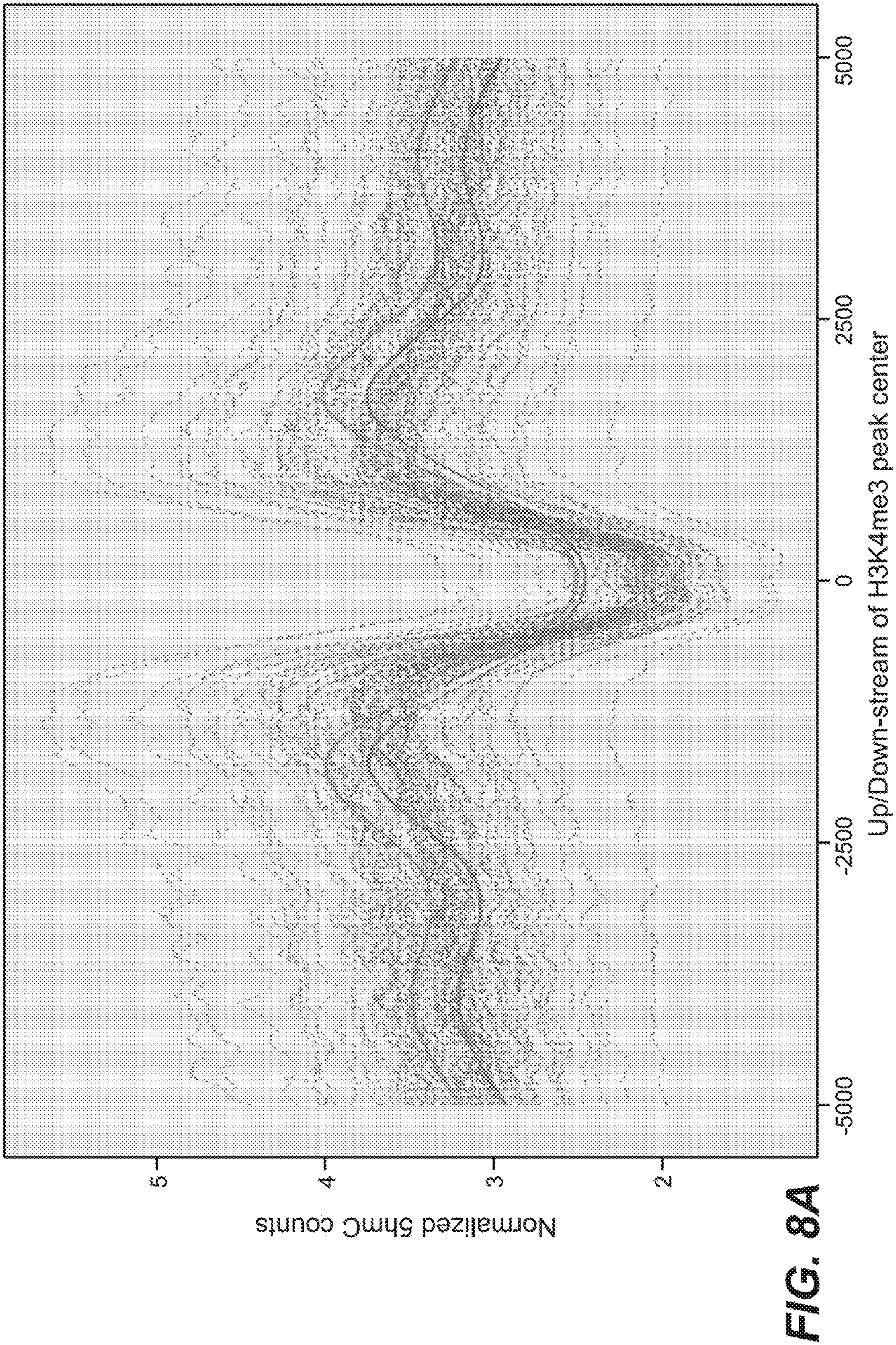
FIG. 8A and FIG. 8B show 5hmC occupancy in the PANC-1 cell line and normal pancreas histone map depicting variable occupancy in H3K4Me3 (FIG. 8A) with depletion at the center of the mark and complementary increase in 5hmC in H3K4Me1 (FIG. 8B). The results support a preferential increase in gene transcription in the PDAC cohort. The Y-axis values are equal to the normalized density of 5hmC counts in 10 bp windows. The dotted red lines=PDAC patient, one per line; the dotted blue lines=non-cancer patients, one per line; the solid red line=the average density of normalized 5hmC counts across all PDAC patients; and the solid blue line=the average density of normalized 5hmC counts across all non-cancer patients.
Figure 8B:
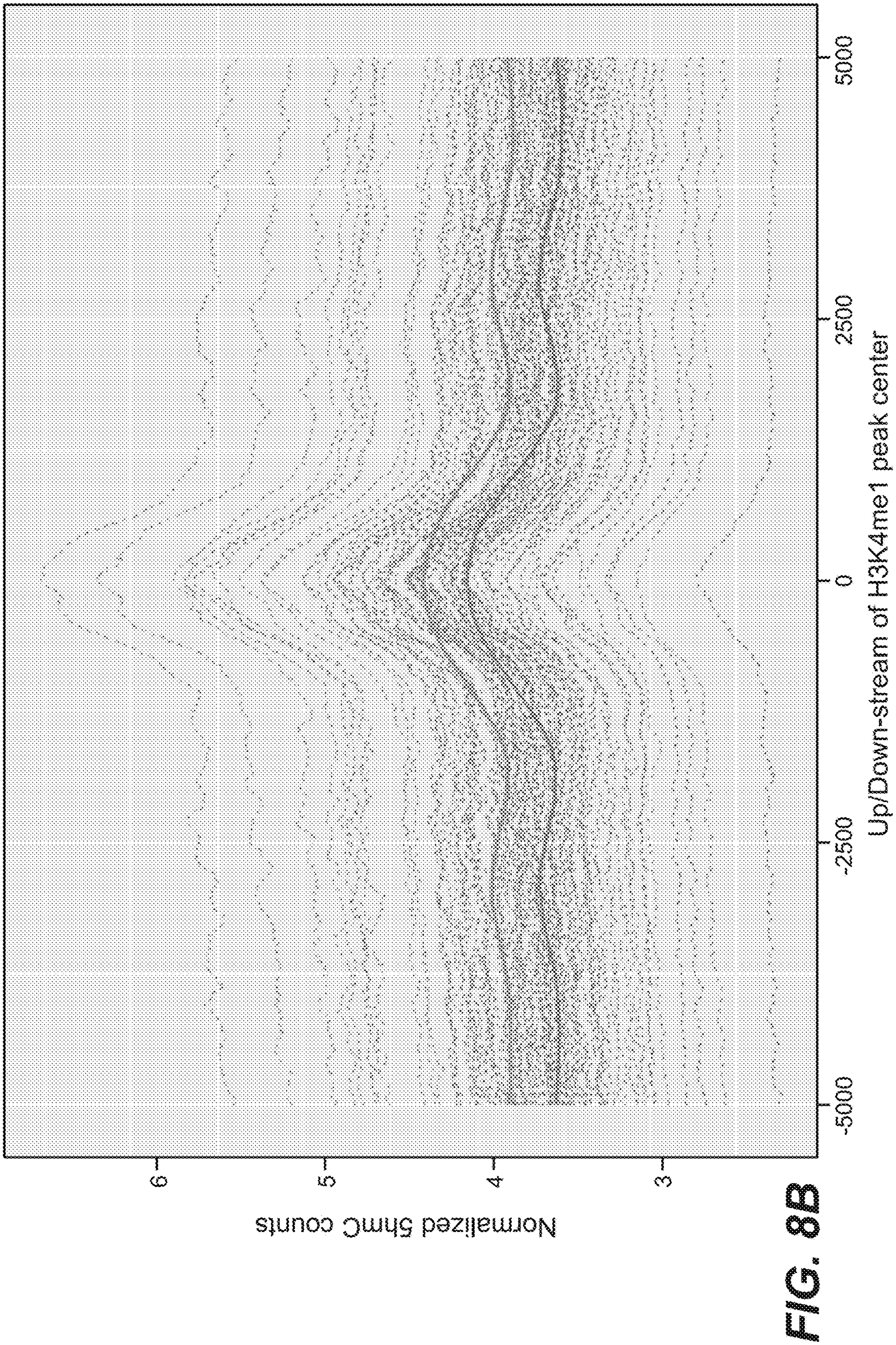
Figure 9:
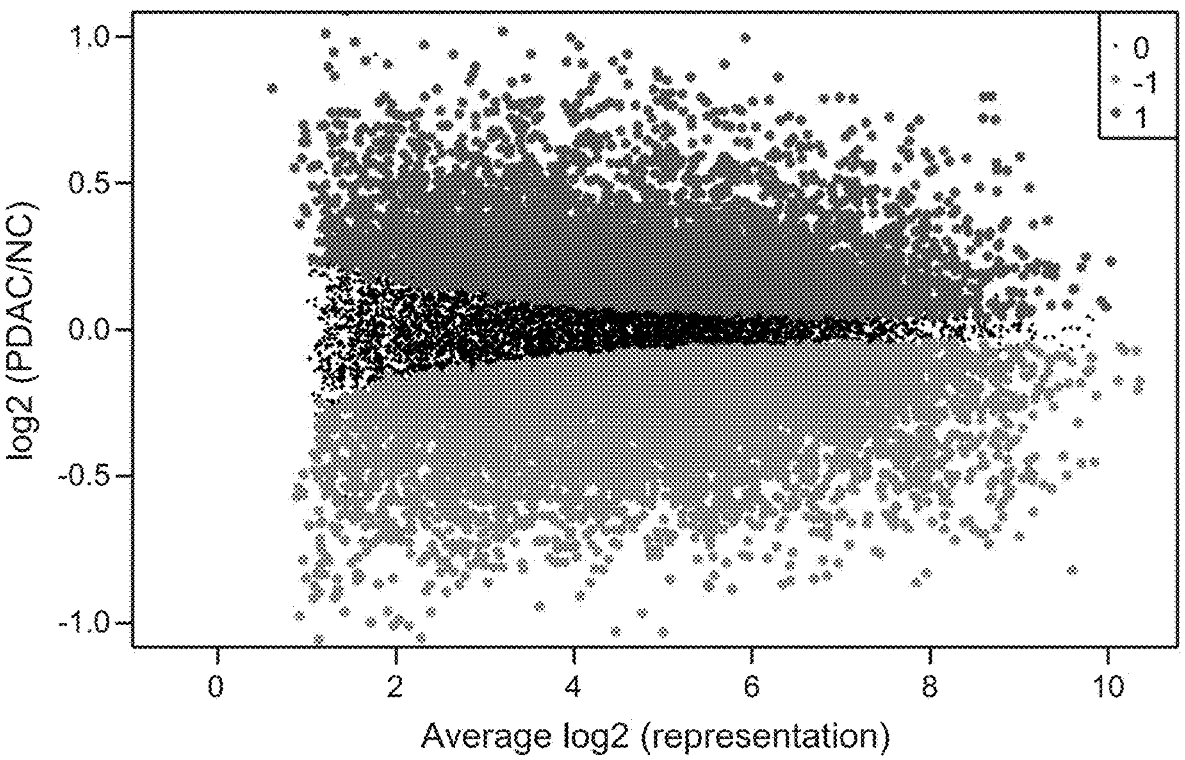
FIG. 9 is an MA plot showing all differentially represented genes and a heatmap showing 5hmC representation on the most significant genes.

Chemical modifications like methylation and acetylation on histone proteins were inferred in relation to 5hmC occupancy, using the existing histone maps from PANC-1 cell lines (see LeRoy et al. (2013) Epigenetics & Chromatin 6:20). Notably, 5hmC decreases were seen in PDAC coincident with H3K4Me3 loci, a transcriptional activating mark (but not H3K4Mel), combined with 5hmC decreases in H3K27Ac and K3K27Me3 loci, which are transcription activating and inactivating respectively (FIG. 7). The statistically significant changes in H3K4Me3, H3K27Ac and H3K27Me3 all exhibited an ongoing reduction in later stage PDAC patients compared with the non-cancer cohort. The H3K27Ac mark had the largest density of 5hmC occupancy in both the cancer and non-cancer cohort and the highest similarity to the Panc1 cell line histone map (FIG. 8A). Conversely, H3K27Me3 exhibited the lowest density of 5hmC occupancy in both cohorts and the lowest similarity to the PANC-1 cell line histone map (FIG. 8B)

Figure 11:
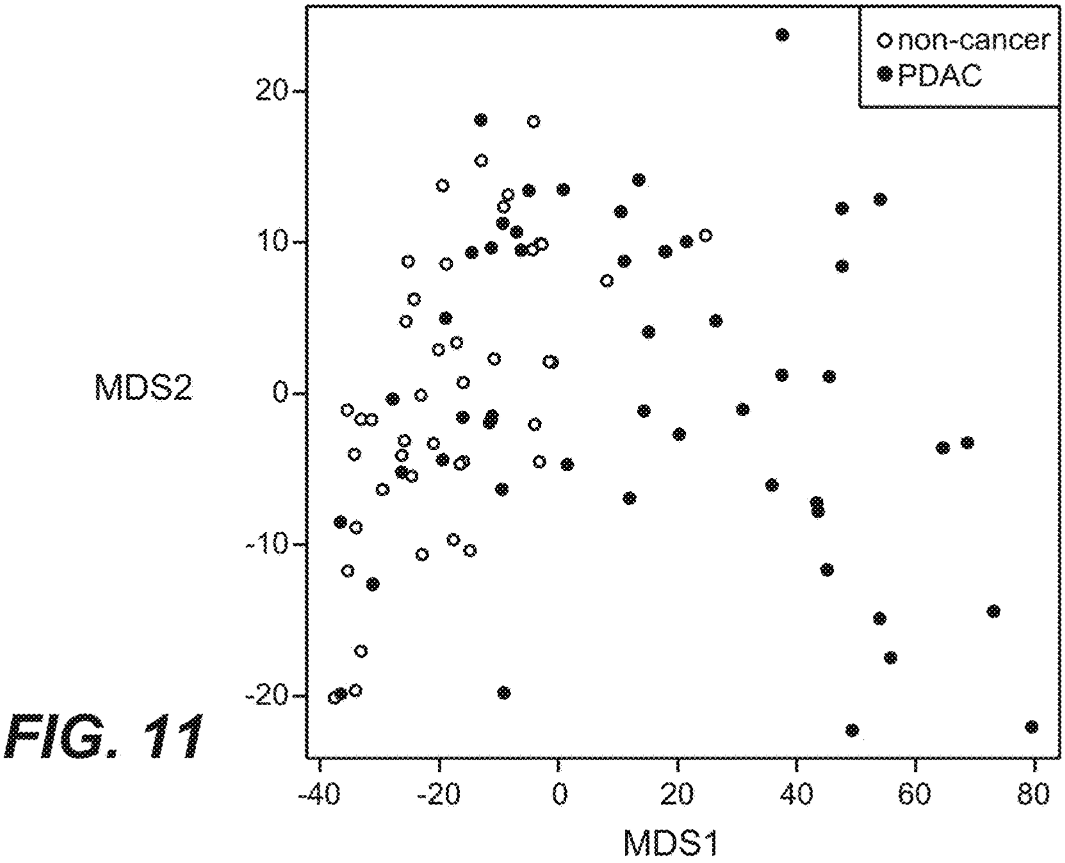
FIG. 11 is a dot plot providing the results of PCA carried out using log [counts per million] on 13,180 genes with a statistically significant (FDR=0.05) increase or decrease in 5hmC in PDAC versus non-cancer samples. The dot plot exhibits visible partitioning of PDAC samples from non-cancer samples.

(d) Identification of Disease Specific Genes from Plasma Samples:

Differential analysis of 5hmC densities in genes revealed 6,496 and 6,684 genes with an increased and decreased 5hmC density, respectively, in PDAC, compared to non-cancer samples (FIG. 11). Further filtering of this gene set (fold change ≥|1.5| in PDAC versus non-cancer and average log 2 CPM≥4 counts, 142 genes total) revealed annotated genes with increased 5hmC density and whose biology is related to pancreas development (GATA4, GATA6, PROX1, ONECUT1) and/or implicated in cancer (YAP1, TEAD1, PROX1, ONECUT2/ONECUT1, IGF1 and IGF2). Inspection of the Molecular Signatures Database (MSigDB) for relevant pathways comprising the 142 genes with enriched 5hmC densities revealed a numeric preponderance of pathways down-regulated in liver cancer (5 of the top 10 most significant pathways, as indicated in Table 6). The differential representation analysis coupled with filtering (fold change ≥|1.5| in PDAC versus non-cancer and log CPM of 5hmC≥4) also revealed 178 genes with a decreased 5hmC density in pancreatic cancer cfDNA (Table 7). Closer inspection of these pathways with decreased 5hmc representation revealed fundamental pathways in immune system regulation (3 of the top 10 most significant pathways, as may be seen in Table 6). Pancreatic cancers are typically diagnosed at late stage where disease prognosis is poor, as exemplified by a 5-year survival rate of 8.2%. Earlier diagnosis would be beneficial by enabling surgical resection or earlier application of therapeutic regimens. The above example illustrates that pancreatic adenocarcinoma can be detected in a non-invasive manner by interrogating changes in 5-hydroxymethylation cytosine status of circulating cell free DNA in the plasma of a PDAC cohort in comparison with a non-cancer cohort. The inventors found that 5hmC sites are enriched in a disease-specific and stage-specific manner in exons, 3'UTRs, and transcription termination sites.

Figure 10:
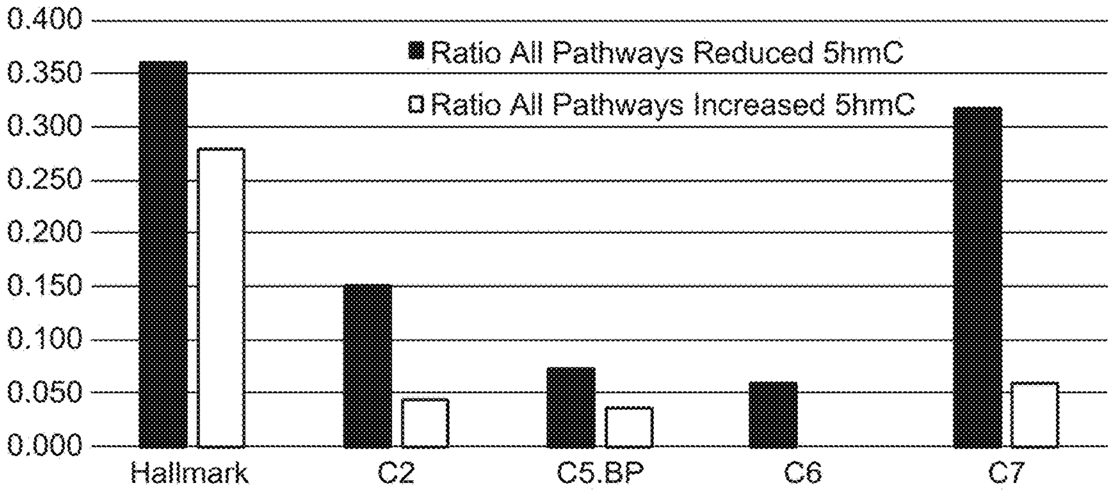
FIG. 10 is a histogram showing the results of gene set enrichment analysis (GSEA) using differentially 5hmC-enriched genes. The blue bars represent the ratio of all pathways exhibiting reduced hydroxymethylation levels, and the orange bars represent the ratio of all pathways exhibiting higher hydroxymethylation levels, in PDAC samples relative to non-cancer samples. GSEA reveals that greater than 20% of KEGG pathways are both up-represented and down-represented in hydroxymethylation levels in PDAC versus non-cancer samples. Also, greater than 30% of immune pathways were found to be down-represented in PDAC versus non-cancer samples.

Expanding gene set enrichment analysis to include the full data set of all genes revealed that more than 30% of immune related pathways have reduced 5-hydroxymethylation across early and late stage PDAC (FIG. 10). Principal component analysis (PCA) using either the 13,180 genes with statistically significant variation in 5hmC counts (FIG. 11), or the 320 genes filtered at the extremes of 5hmC representation in PDAC (FIG. 12), revealed partitioning of the PDAC samples from the non-cancer samples equally well, indicating no loss of partitioning signal using a biologically relevant and statistically filtered gene set.

TABLE 6

[]Top ten pathways represented by 142 genes with increased 5hmC density in PDAC samples versus non-cancer samples (also see Collin et al. (2018), "Detection of Early Stage Pancreatic Cancer Using 5-Hydroxymethylcytosine Signatures in Circulating Cell-Free DNA," bioRxiv, dx.doi.org/10.1101/422675, incorporated by reference herein):

| Gene Set* | Description | k/K | p-value | FDR q-value |
|---|---|---|---|---|
| 1 | Genes down-regulated in liver tissue upon knockout of HNF1A (GeneID=6927). | 0.0892 | 3.92E−17 | 5.61E−13 |
| 2 | Genes down-regulated in tumor compared to non-tumor liver<br>samples from patients with hepatocellular carcinoma (HCC). | 0.2041 | 2.35E−16 | 1.68E−12 |
| 3 | The chemical reactions and pathways involving small molecules (any low molecular weight, monomeric, non-encoded molecule). | 0.0175 | 5.53E−16 | 2.64E−12 |
| 4 | Liver-selective genes. | 0.0615 | 7.06E−16 | 2.72E−12 |
| 5 | Genes from subtype S3 signature of HCC: hepatocyte differentiation. | 0.0564 | 2.73E−15 | 7.81E−12 |

TABLE 6-continued

[]Top ten pathways represented by 142 genes with increased 5hmC density in PDAC samples versus non-cancer samples (also see Collin et al. (2018), "Detection of Early Stage Pancreatic Cancer Using 5-Hydroxymethylcytosine Signatures in Circulating Cell-Free DNA," bioRxiv, dx.doi.org/10.1101/422675, incorporated by reference herein):

| Gene Set* | Description | k/K | p-value | FDR q-value |
|---|---|---|---|---|
| 6 | Genes down-regulated in liver tumor compared to the normal adjacent tissue. | 0.0547 | 4.22E−15 | 1.01E−11 |
| 7 | The chemical reactions and pathways involving lipids and lipidic molecules (fatty alcohols, sphingoids, phospholipids, glycolipids, sterols, etc.). | 0.0216 | 5.47E−15 | 1.12E−11 |
| 8 | The chemical reactions and pathways involving organic acids. | 0.0241 | 7.39E−15 | 1.32E−11 |
| 9 | Any process that results in a change in state or activity of a cell or an organism (movement, secretion, enzyme production, gene expression, etc.) as a result of a stimulus arising within the organism. | 0.0179 | 1.08E−13 | 1.61E−10 |
| 10 | Down-regulated genes distinguishing between early gastric cancer (EGC) and normal tissue samples. | 0.0409 | 2.98E−13 | 4.27E−10 |

*Gene set names:
1: SERVITJA_LIVER_HNF1A_TARGETS_DN
2: LEE_LIVER_CANCER
3: GO_SMALL_MOLECULE_METABOLIC_PROCESS
4: HSIAO_LIVER_SPECIFIC GENES
5: HOSHIDA_LIVER_CANCER_SUBCLASS_S3
6: ACEVEDO_LIVER_TUMOR_VS_NORMAL_ADJACENT
7: GO_LIPID_METABOLIC_PROCESS
8: GO_ORGANIC_ACID_METABOLIC_PROCESS
9: GO_RESPONSE_TO_ENDOGENOUS_STIMULUS
10: VECCHI_GASTRIC_CANCER_EARLY_DN

TABLE 7

[]Top ten pathways represented by 178 genes with decreased 5hmC density in PDAC samples versus non-cancer samples (also see Collin et al. (2018), supra):

| Gene Set* | Description | k/K | p-value | FDR q-value |
|---|---|---|---|---|
| 1 | Genes involved in hemostasis | 0.0708 | 1.80E−33 | 2.58E−29 |
| 2 | Any process that modulates the frequency, rate, or extent of an immune system process. | 0.0314 | 1.06E−29 | 7.56E−26 |
| 3 | Genes down-regulated in CD34+ (GeneID=947) cells by intermediate activity levels of STAT5A (GeneID=6776); predominant long-term growth and self-renewal phenotype. | 0.108 | 9.52E−28 | 4.54E−24 |
| 4 | Any process involved in the development or functioning of the immune system. | 0.0242 | 1.62E−27 | 5.79E−24 |
| 5 | Any process that modulates the levels of body fluids. | 0.0553 | 1.76E−25 | 5.05E−22 |
| 6 | A change in the morphology or behavior of a cell resulting from exposure to an activating factor such as a cellular or soluble ligand. | 0.0511 | 2.19E−25 | 5.23E−22 |
| 7 | Any process that activates or increases the frequency, rate, or extent of an immune system process. | 0.0381 | 8.38E−25 | 1.71E−21 |
| 8 | Any process that modulates the frequency, rate, or extent of cell activation. | 0.0558 | 1.11E−24 | 1.98E−21 |
| 9 | Genes involved in platelet activation, signaling, and aggregation. | 0.0962 | 3.27E−23 | 5.19E−20 |
| 10 | Any process that modulates the frequency, rate, or extent of attachment of a cell to another cell or to the extracellular matrix. | 0.0429 | 1.04E−21 | 1.49E−18 |

*Gene set names:
1: REACTOME_HEMOSTASIS
2: GO_REGULATION_OF_IMMUNE_SYSTEM_PROCESS
3: WIERENGA_STAT5A_TARGETS_DN
4: GO_IMUNE_SYSTEM_PROCESS
5: GO_REGULATION_OF_BODY_FLUID_LEVELS
6: GO_CELL_ACTIVATION
7: GO_POSITIVE_REGULATION_OF_IMMUNE_SYSTEM_PROCESS
8: GO_REGULATION_OF_CELL_ACTIVATION
9: REACTOME_PLATELET_ACTIVATION_SIGNALING_AND_AGGREGATION
10: GO_REGULATION_OF_CELL_ADHESION Regularized regression models were built using 5hmC densities in statistically filtered genes or a comprehensive set of highly variable gene counts and performed with an AUC=0.94-0.96 on training data. The inventors tested the capability of classifying PDAC and non-cancer samples with the elastic net and lasso models on two external pancreatic cancer 5hmC data sets and found validation performance to be AUC=0.74-0.97. The findings show that 5hmC changes enable classification of PDAC patients with high fidelity.

(e) Predictive Models for the Detection of Pancreatic Cancer in cfDNA

Regularized logistic regression analysis was performed in order to determine whether gene-based features are present in the PDAC and non-cancer cohorts that enable the classification of patient samples. The full set of 92 patient samples was partitioned into a training and test set comprising 75% and 25% of the patient data, respectively, and 65% of the genes with the most variable 5hmC count was employed for model selection. Two methods of regularization were used, Elastic Net (glmnet) and Lasso (glmnet2) (Yu et al. (2016) BMC Bioinformatics 17:108).

Figure 12:
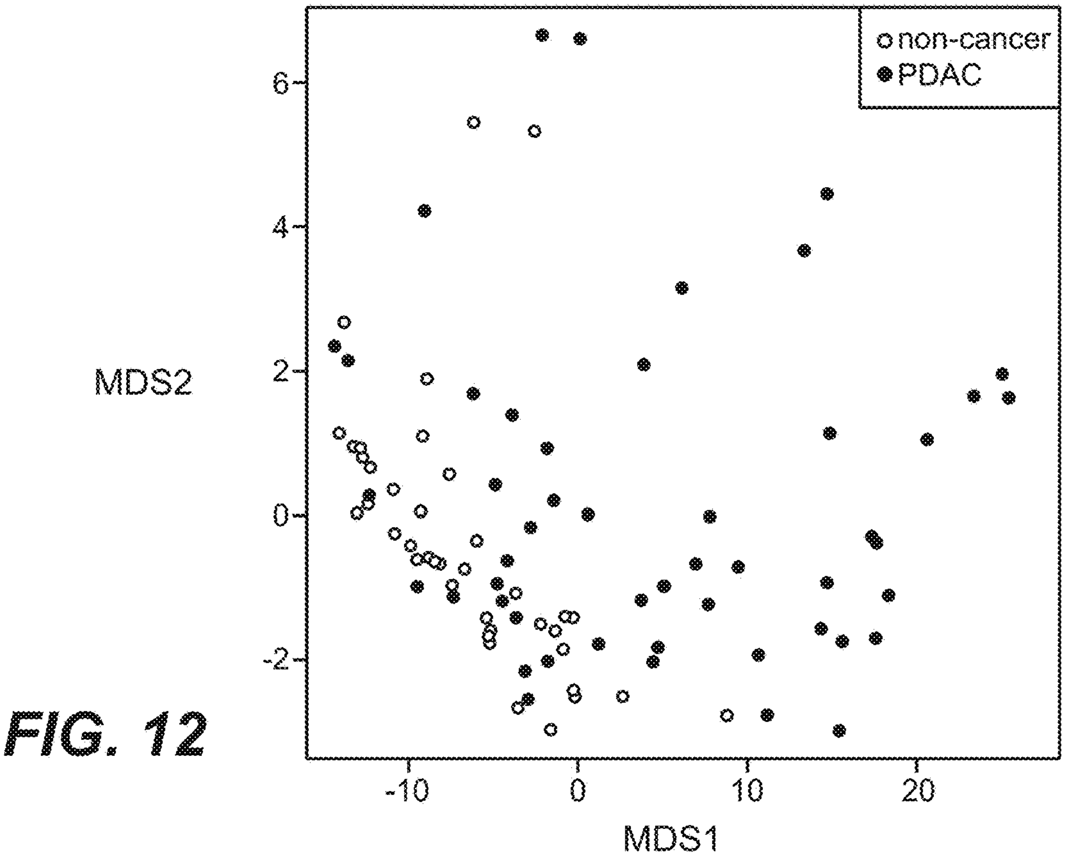
FIG. 12 is a PCA dot plot carried out using log [counts per million] on 320 genes, a subset of the 13,180 genes that exhibited a statistically significant (FDR=0.05) increase or decrease in 5hmC in PDA versus non-cancer samples, where the data was filtered for increased PDAC representation as follows: (1) (log 2 [5hmC-PDAC/5hmC-non-cancer]≥0.58; and (2) log 2 [average representation]≥5. The dot plot again shows good partitioning of PDAC samples from non-cancer samples despite an order of magnitude smaller gene set than used in the generation of FIG. 11.
Figure 13:
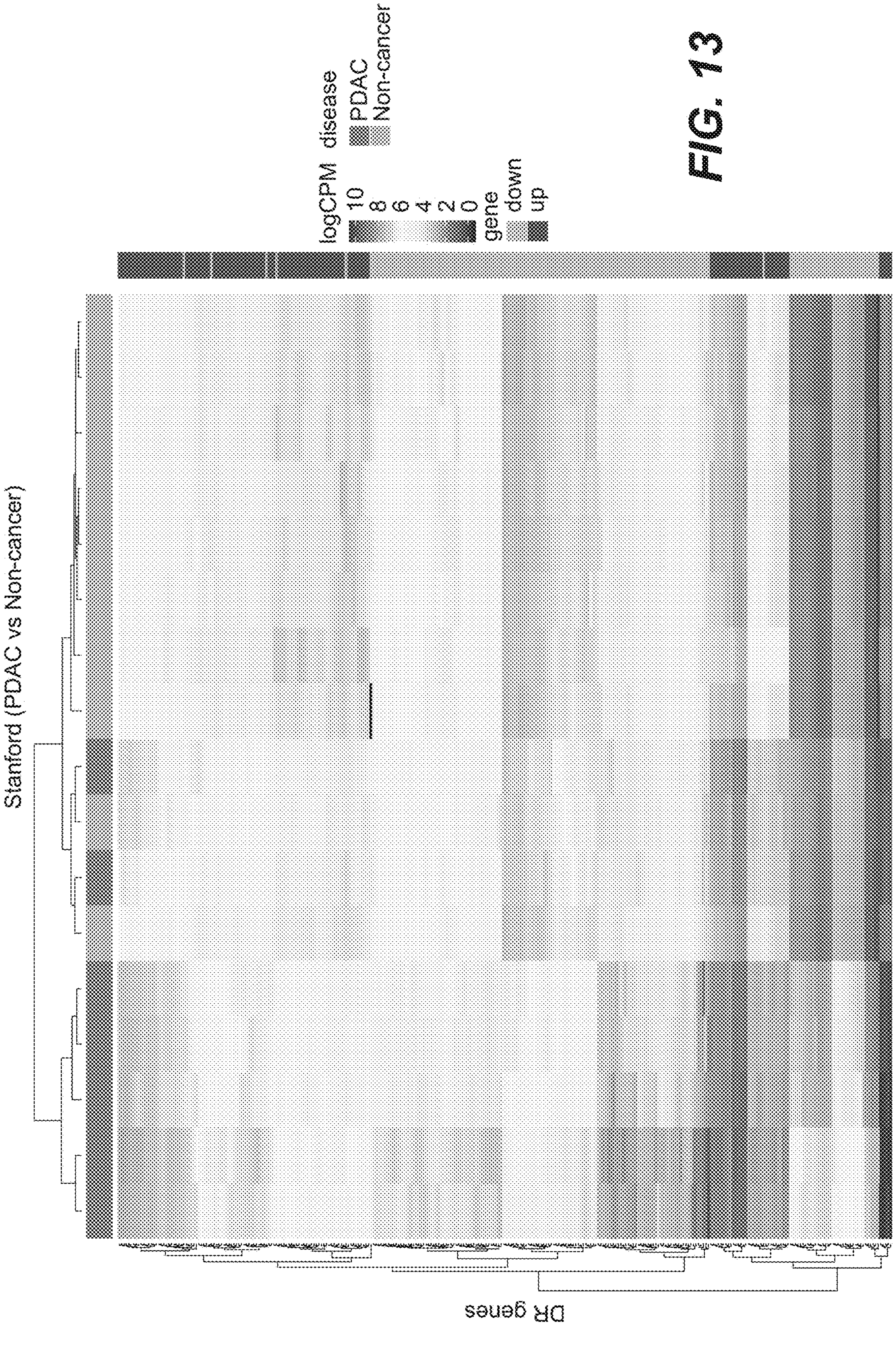
FIG. 13 is a heatmap depicting the hierarchical clustering results obtained using the 320 genes selected for the PCA of FIG. 12 (the genes represent rows in the heatmap), to show how labeled samples (columns in the heat map) can be partitioned using log(CPM) 5mC counts. The heatmap shows near-perfect partitioning of the data, which in this case was that used by Stanford University in Song et al. (2017) *Cell Research* 27:1231-42 (sometimes referred to herein as the "Stanford data").
Figure 14:
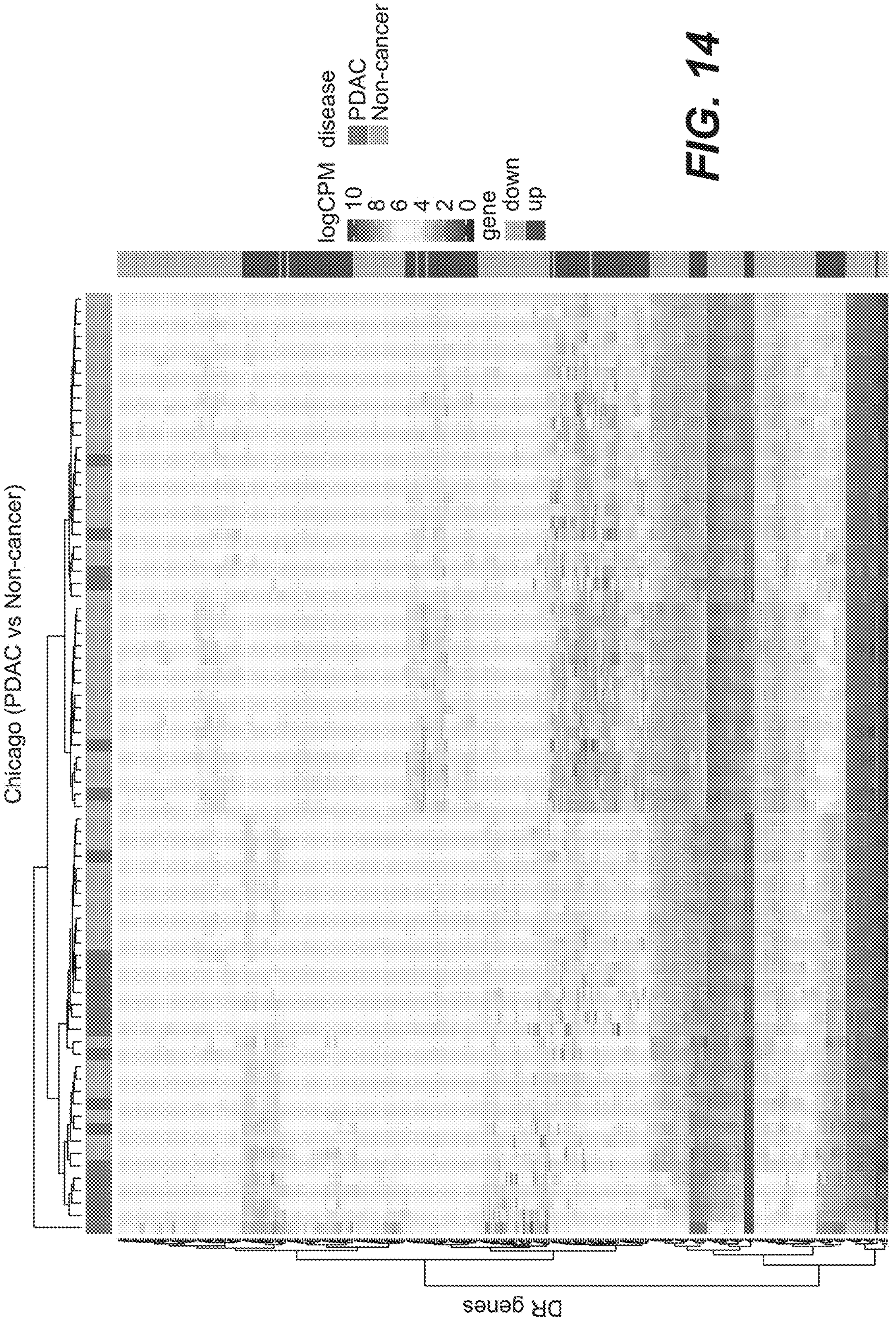
FIG. 14 is also a heatmap, prepared as explained above for FIG. 13, but using the data of Li et al. (2017) *Cell Research* 27:1243-1257 (sometimes referred to herein as the "Chicago data"). In contrast to the almost perfect partitioning of the Stanford data, the Chicago data gave somewhat incomplete partitioning.
Figure 15:
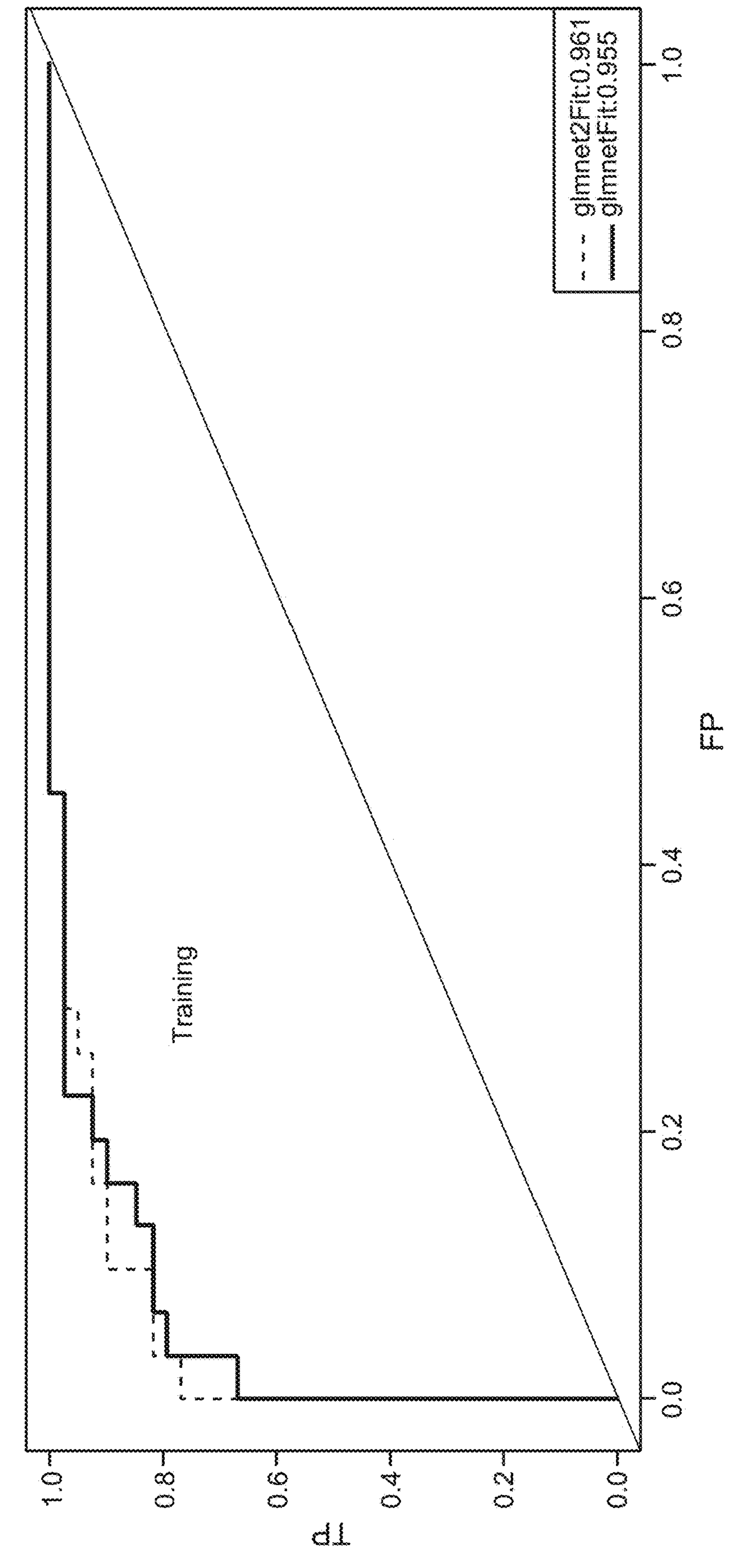
FIG. 15 and FIG. 16 provide the results of predictive modeling using two regularization models, Elastic Net and Lasso.

Both regularization methods require the specification of hyper-parameters that control the level of regularization used in the fit. Hyper-parameters were selected based on out-of-fold performance on 30 repetitions of 10-fold cross-validated analysis of the training data. Out-of-fold assessments were based on the samples in the left-out fold at each step of the cross-validated analysis. The training set yielded an out-of-fold performance metric, Area Under Curve (AUC), of 0.96 (elastic net and lasso) with an internal sample test AUC of 0.84 (elastic net) and 0.88 (lasso) (FIG. 15). The distribution of probability scores shows that within training data, both models classify well (FIG. 16) but that marginally fewer misclassified samples are found with the elastic net model when the specificity is set at 75%, i.e., fewer cancer samples score below the third quartile non-cancer score and fewer non-cancer samples score above the same third quartile non-cancer score. Next, the training model was tested on an external validation set of patient samples. These include pancreatic cancer samples from Li et al. (2017) Cell Research 27:1243-1257 (pancreas subtype not specified; 23 subjects with pancreatic cancer, 53 healthy) and Song et al. (2017) Cell Research 27: 1231-42 (pancreas subtype specified as adenocarcinoma; 7 subjects with pancreatic cancer, 10 healthy). The validation set exhibited a performance with AUC=0.78 (elastic net and lasso) in the Li et al data and AUC=0.99 (elastic net) and 0.97 (lasso) in the Song et al. (2017) data (FIG. 12).

Figure 16:
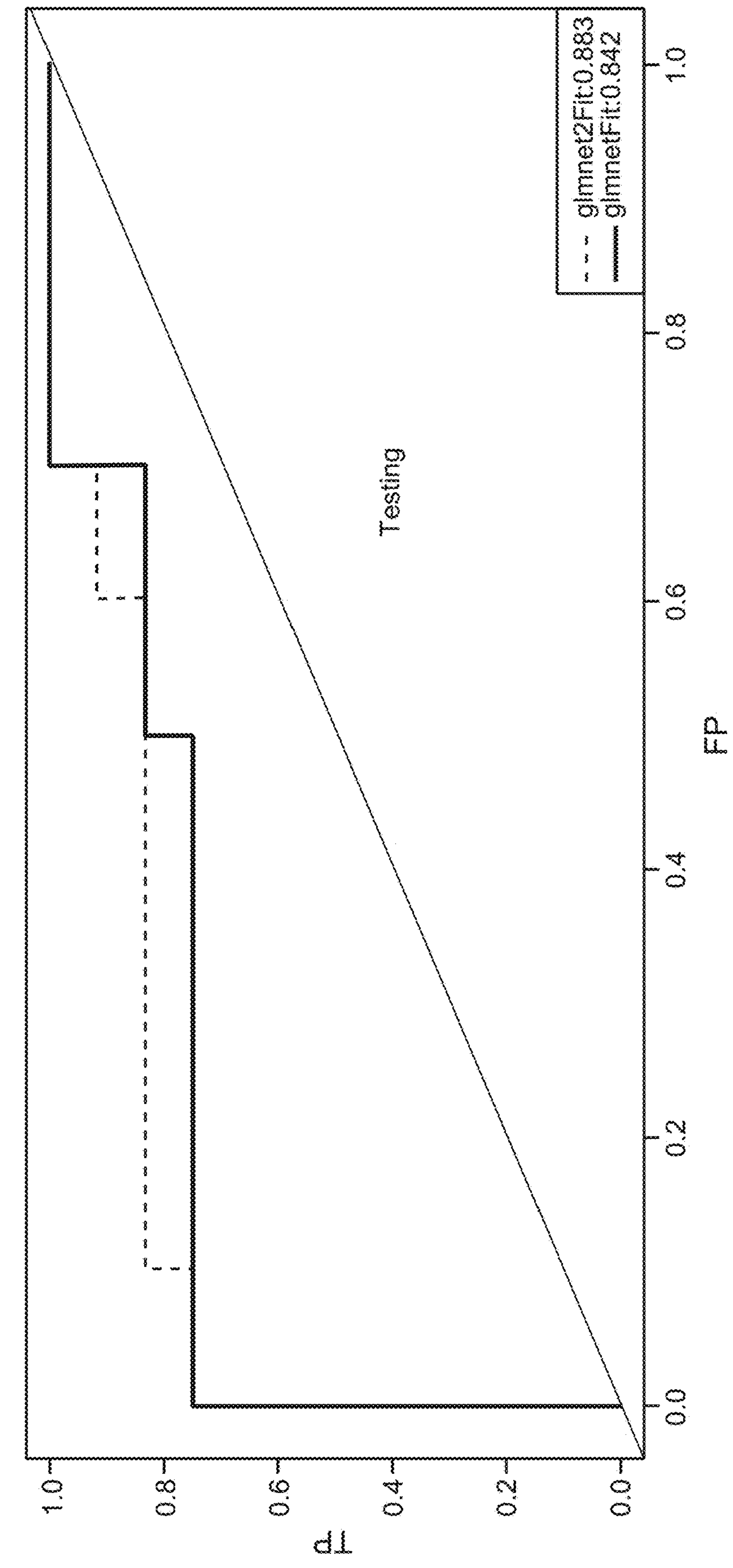

The effect of feature selection on prediction performance was evaluated by filtering the initial set of significant genes (FIG. 10) to satisfy a 1.5-fold differential 5hmC representation in the PDAC cohort with median representation of gene counts of log 2 average 5hmC representation >4. The same regularized regression models were built using this set of 287 genes with increased 5hmC and 343 genes with decreased 5hmC counts, employing a similar setup for training and testing as defined previously (75% data used for training, 25% data used for test) and found training set AUC=0.96 (elastic net) and 0.94 (lasso). Not surprisingly, internal testing yields a high performance with AUC=0.92 (elastic net) and 0.93 (lasso). Of greater interest was the performance on external data sets with AUC=0.74 (elastic net) and 0.67 (lasso) for Li et al data and AUC=0.97 (elastic net) and 0.94 (lasso) for Song et al. (2017) data. This suggests that genes with evident enrichment of biological signal relevant to pancreatic cancer and/or pancreas development do not perform much better than an algorithmically driven selection of features during regression training, as has been shown elsewhere (ibid.). Hierarchical clustering of these significant genes (287 with increased 5hmC+343 with decreased 5hmC) showed good partitioning of the pancreatic cancer samples in the Stanford data set but less pronounced separation of Chicago data (FIG. 16).

Figure 17:
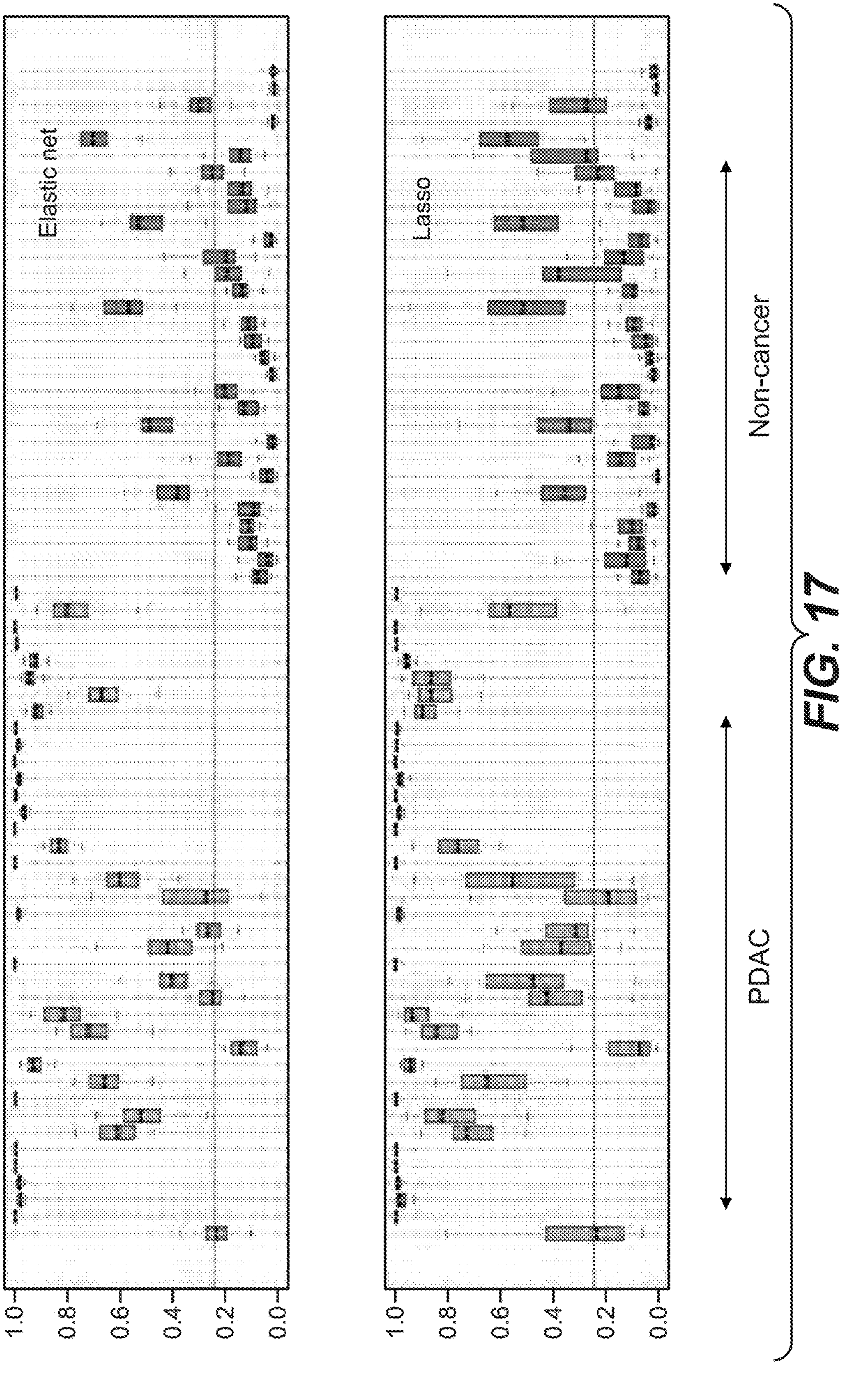
FIG. 17 gives the probability scores derived from each sample in the training data set using the Elastic Net and Lasso regularization methods. Probability scores near 1 are predicted cancer samples, while probability scores close to zero are non-cancer samples. The red line identified Q3 probability score of the non-cancer samples.
Figure 18:
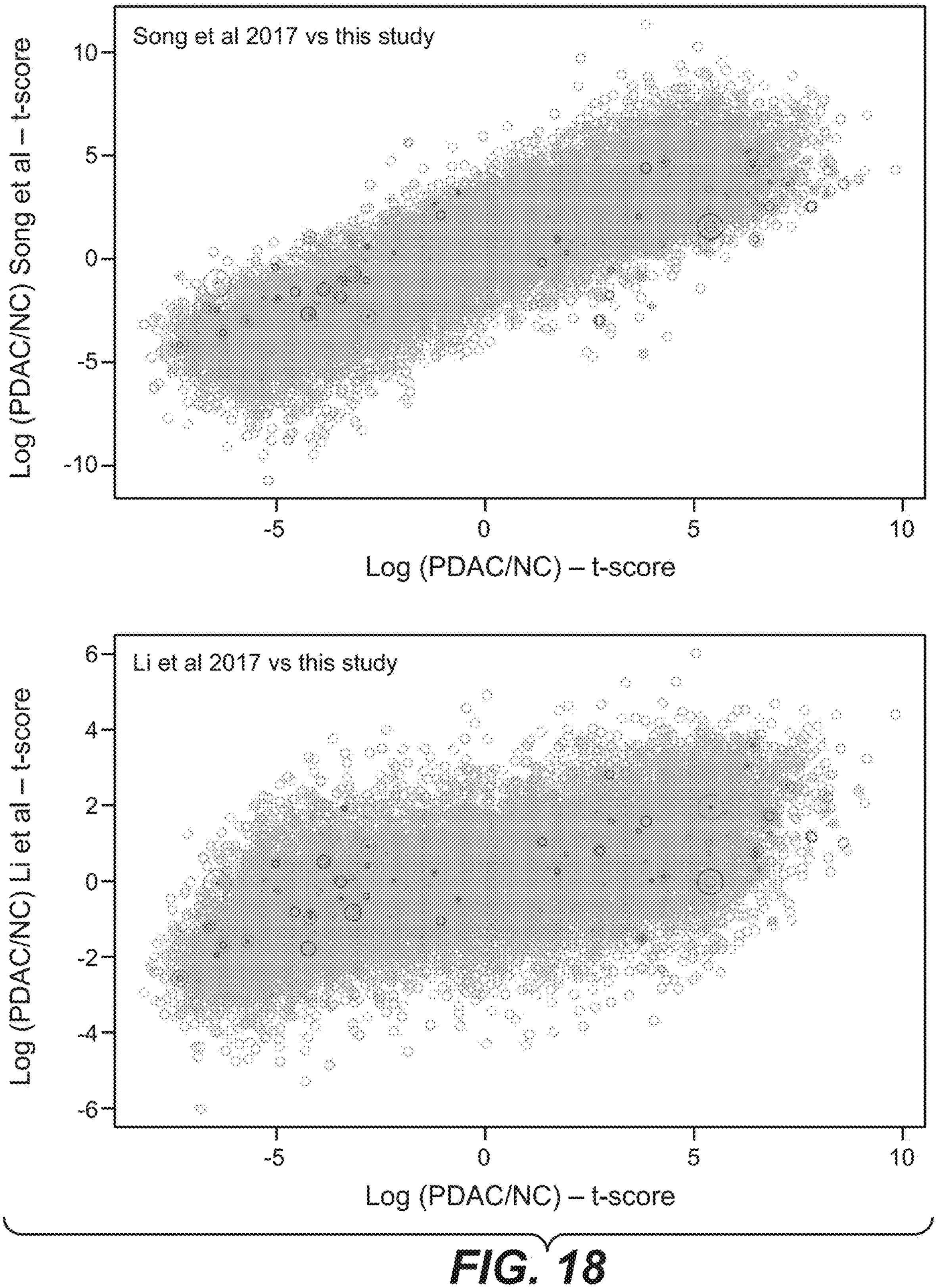
FIG. 18 represents the validation of the predictive models used with the Li et al. (2017) (Chicago) and Song et al. (2017) (Stanford) PDAC and non-cancer data sets.
Figure 19:
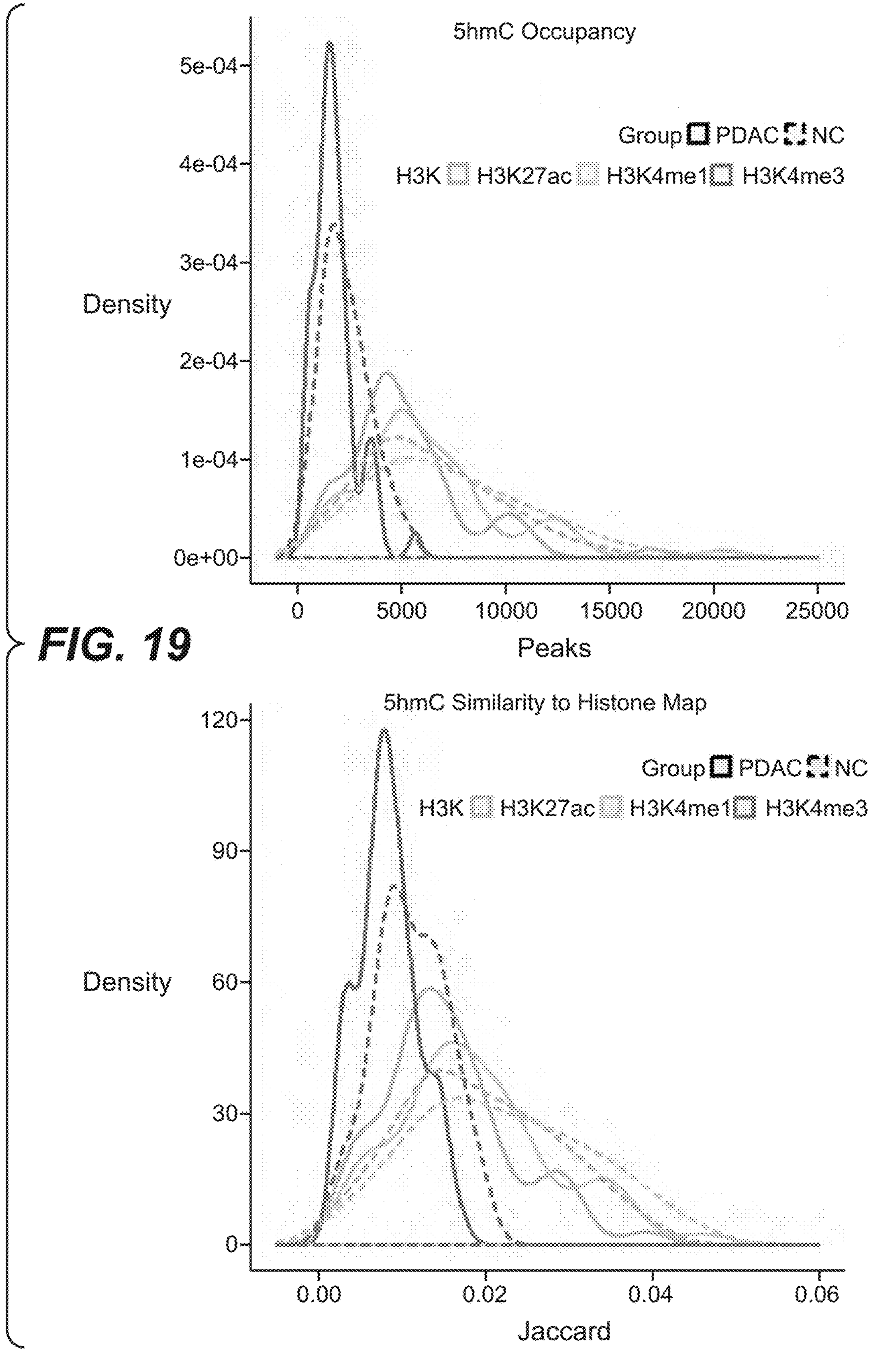
FIG. 19 illustrates in graph form the hydroxymethylation levels ("5hmC occupancy") at loci associated with histone biomarkers H3K4me3, H3K4mel, and H3K27ac, and the similarity to an existing histone map from PANC-1 cell lines (LeRoy et al. (2013) *Epigenetics & Chromatin* 6:20).

The final models fitted to the 65% most variable 5hmC gene features, using hyper-parameter values determined from the training set data analysis, were fitted to the whole cohort of PDAC and non-cancer samples and this yielded models with 109 genes (elastic net) and 47 genes (lasso). The models were found to possess t-scores that are concordant both the Li et al and Song et al. (2017) data sets (FIG. 17).

DISCUSSION

The experimental work detailed above focused on the discovery of cfDNA-specific hydroxymethylation-based biomarkers that would facilitate the development of molecular diagnostic tests to detect pancreatic cancer at earlier stages. The data discussed above and presented in the figures highlight the ability to detect differentially hydroxymethylated genes whose underlying biology shows association with both pancreas and cancer development as well as established trends in marked, known functional regions of the genome. Furthermore, by using either 5hmC signals from biologically significant genes or from regularized regression methods, predictive models can be built with AUC=0.94-0.96 with an external data set validation AUC=0.74-0.97 (elastic net models).

Figure 4:
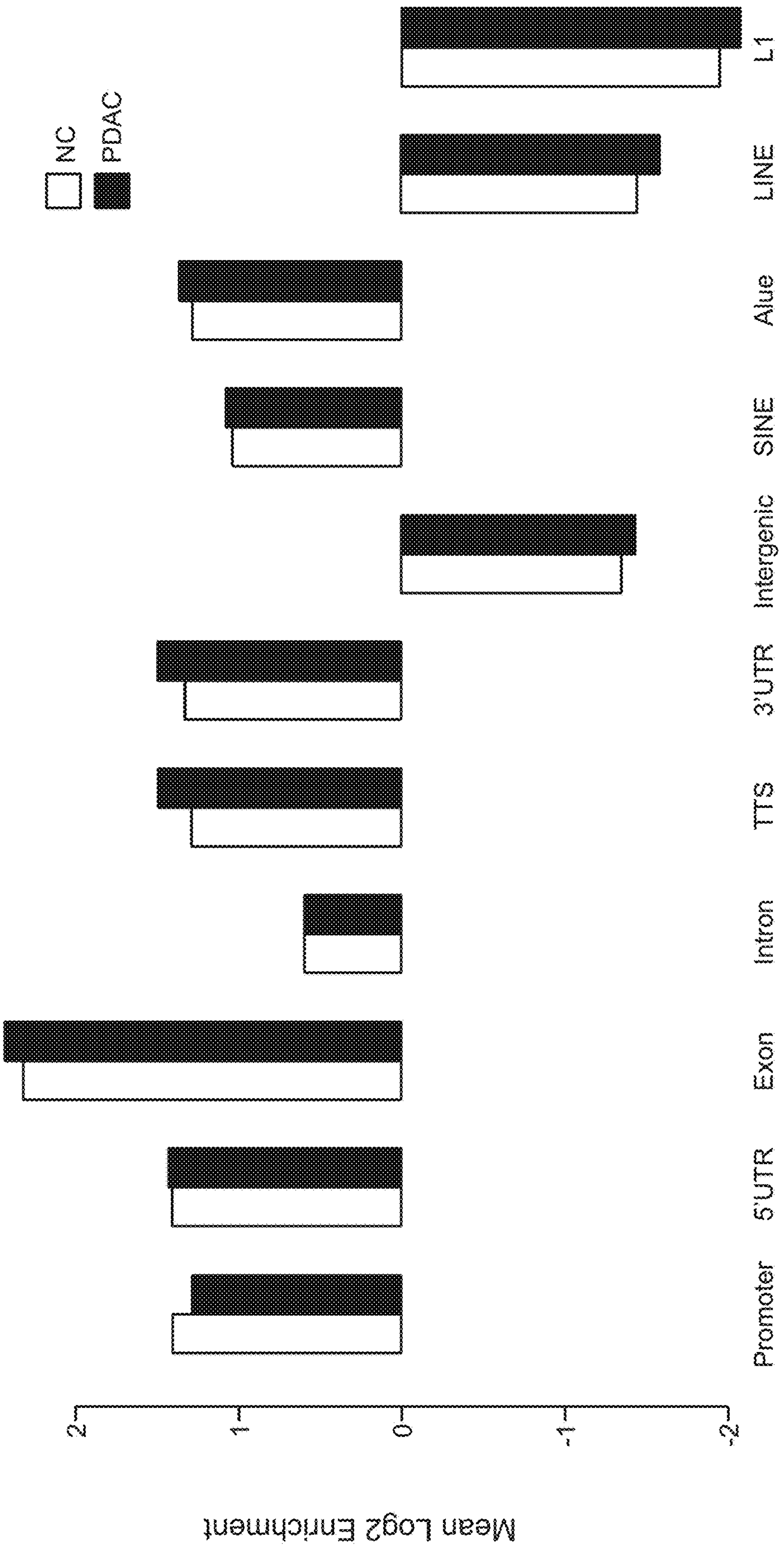
FIG. 4 is a histogram providing the results of the enrichment analysis described in Example 1, with the Y-axis value equal to the mean of log 2 (cancer/non-cancer). The histogram shows that gene-based features, SINEs, and Alus are enriched in 5hmC in both cancer and non-cancer cohorts, whereas intergenic regions, LINEs, and Lis are depleted of 5hmC peaks.

The 5hmC signal was found to be enriched in gene-centric sequence types (promoter, exons, UTR and TTS), as well as transposable elements like SINEs (enriched) and LINEs (depleted) (FIGS. 3 and 4). These hydroxymethylation changes in functional regions have been reported in cfDNA from colorectal, esophageal, liver, and lung cancer (see Li et al. (2017), supra; Tian et al. (2018) Cell Res 5:597-600; Cai et al. (2018), "5-Hydroxymethylcytosines from Circulating Cell-free DNA as Diagnostic and Prognostic Markers . . . ," bioRxiv (doi.org/10.1101/424978), and Zhang et al. (2018) Genomics, Proteomics & Bioinformatics 16: 187-199); however, no PDAC-specific gains or losses in hydroxymethylation were observed in functional regions. In addition to enrichment and depletion of 5hmC in functional regions, there was a novel PDAC specific 5hmC increase in exons, TTS and 3'UTR and a 5hmC decrease in promoters and LINE elements (FIG. 5). In ES cells, the decrease of 5-hydromethylation in the promoter region has been shown to associate with gene transcription (see Szulwach et al. (2011) PLoS Genetics 7(6): e1002154). An increase in disease relevant transcription is be implicitly supported in the above data by the 5hmC increase seen in gene-centric features and the apparent decreasing trend of 5hmC in promoter regions toward late stage PDAC (FIG. 6).

Dynamic changes in chromatin have been shown to control cell development and transition of cells with oncogenic potential; see Bernhart et al. (2016) Scientific Reports 6, Article number 37393. The PDAC specific decrease of 5hmC in H3K4me3 loci appears to be coincident with a non-statistically significant increase of 5hmC in H3K4mel (FIG. 7). These DNA hydroxymethylation patterns complement each other both in genomic location and the histone marks they occupy (FIGS. 8A and 8B), and also suggest disease-specific increases in gene transcription via chromatin modifications, given the known permissive transcriptional function associated with H3K4me3/mel. An intriguing aspect of the precision of 5hmC patterns in these regions of known functional sequence suggest a widespread function for hydroxylation in the epigenetic control of transcriptional processes.

In this study, genes were identified whose increased 5hmC signals in highlighted pathways are implicated in liver cancer (Table 7). MSigDB does not currently contain pathways annotated for pancreatic cancer; see Subramanian et al. (2005), PNAS 102:15545-50. Two approaches were used for gene set enrichment analysis, either using genes with significantly decreased 5hmC or performing GSEA on all reporting genes. The results indicated that close to one third of immune system pathways were implicated in pancreatic cancer. Assuming the strong association between 5hmC extent and gene transcription, this result suggests that immune system function is decreased in PDAC patients. Inspection of individual genes that were either significantly increased or decreased in functional regions reveals genes implicated in normal pancreas development, for instance the transcription factors GATA4, GATA6, PROX1, ONECUT2, and also genes whose increased expression is implicated in cancer like YAP1, TEAD, PROX1, ONECUT2, ONECUT1, IGF1 and IGF2.

Using genes whose 5hmC densities are significantly changed in PDAC, with annotated relevant biology, it was possible to build regularized regression models whose performance matched model building using algorithm gene based selection. This provided confidence that the models used, whose performance is high (training AUC=0.94-0.96 with an external data set validation AUC=0.74-0.97), is measuring underlying biological signals relevant to PDAC. Despite the large number of significantly hydroxymethylated genes, the regularized regression models selected 100 genes or fewer. However, the fact that 13,180 significantly represented genes were detected provide evidence that other biological signals may also reside in the data set. Smoking status is a known risk factor for PDAC up to 20 years post-smoking cessation, and DNA methylation changes have been associated with tobacco-based toxins (Lee (2013) Front Genet 4:132). In a retrospective case-control designed study, smokers constituted 59% and 49% of PDAC and non-cancer cohorts respectively, indicating that smokers are equally spread in each cohort. Consequently, the association of smoking in the PDAC cohort could not have accounted for the significantly hydroxymethylated genes found. However, a more extensive study focused on sub-partitioning PDAC and non-cancer patient into never and ever smokers with pack-year characteristics would enable us to answer the impact of smoking on the hydroxymethylome in PDAC patients.

Example 2

Example 1 was repeated with an additional study group, Study Group 2, of 41 PDAC and 82 non-cancer subjects. The clinical characteristics of the cancer and non-cancer cohorts in Study Group 2 are set forth in Table 8.

TABLE 8

| | No Cancer | Cancer |
|---|---|---|
| Age+ | | |
| | 66.0 | 65.5 |
| Gender(%) | | |
| Male | 50 | 44 |
| Smoking History Status(%) | | |
| Current | 5 | 12 |
| Former | 54 | 39 |
| Never | 41 | 49 |
| Stage | | |
| NA | NA | 5 |
| I | NA | 22 |
| II | NA | 29 |
| III | NA | 15 |
| IV | NA | 29 |

+mean of Non-Cancer and Cancer

The procedures documented in Example 1 were followed to generate the 611 hydroxymethylation biomarkers set forth in FIG. 21.

Example 3

Example 1 was repeated with a further study group, Study Group 3, of 53 PDAC and 53 non-cancer subjects. The clinical characteristics of the cancer and non-cancer cohorts in Study Group 3 are set forth in Table 9.

TABLE 9

| | No Cancer | Cancer |
|---|---|---|
| Age+ | | |
| | 66.0 | 66.4 |
| Gender(%) | | |
| Male | 44 | 53 |
| Smoking History Status(%) | | |
| Current | 21 | 21 |
| Former | 32 | 32 |
| Never | 47 | 47 |
| Stage | | |
| NA | NA | 4 |
| I | NA | 21 |
| II | NA | 36 |
| III | NA | 11 |
| IV | NA | 28 |

+mean of Non-Cancer and Cancer

The procedures documented in Example 1 were followed to generate the 41 hydroxymethylation biomarkers set forth in Table 4, provided earlier herein, and in FIG. 22.

The invention claimed is:

1. A method for monitoring the effectiveness of treatment in a patient with a pancreatic lesion identified on an imaging scan, the method comprising:

(a) obtaining an initial cell-free DNA sample that comprises genes relevant to PDAC and its variants from a patient who is being treated for a pancreatic lesion;

(b) enriching for hydroxymethylated DNA in the sample;

(c) quantifying the hydroxymethylated DNA in the enriched initial sample that map to each of a plurality of selected loci in a reference hydroxymethylation profile, wherein the selected loci comprise hydroxymethylation biomarkers related to the presence, absence, or risk of pancreatic PDAC and its variants comprising ADARB2-AS1, ANKRD36B, ASAH2B, ATG4B, ATP8B1, BOLA1, C11orf88, C17orf97, C1orf170, C3orf36, C8orf74, CAMSAP2, CCDC54, CCDC59, CKAP2, CLK2P, CRTC1, CSRP2, CYB5D1, DNAJC27, DYNAP, FAM166A, FAM188B, FAM196A, FAM86JP, FAT4, FBXO5, FGF2, FUT2, GAS2L2, GAS6, GGACT, GLRX5, GPX1, GPX5, HBD, HLA-A, HTR1F, IL36G, KANSL1, KCNH6, KCTD15, KLHL38, KLK2, KRT6B, LAMC1, LGALS14, LGALS8-AS1, LIFR, LINC00266-1, LINC00310, LOC100130452, LOC100130557, LOC100130894, LOC100288778, LOC100505633, LOC100505648, LOC100505738, LOC100652909, LOC389033, LOC90784, LRRC37A2, MED11, MRPL23-AS1, NAT8L, NEUROD1, NEUROG2, NME5, NOMO3, NPRL2, NXN, ODF3L1, ODF3L2, OSCP1, PARD6G, PGAM1, PLA2G2E, PLSCR4, PPAP2A, PPP1R15A, PPP1R3E, RASL10B, REXO1L1, RIMBP3, RNF126P1, RNU6-76, RPP25, RPS27, SH3PXD2B, SHISA4, SLC25A38, SLC4A1, SLCO5A1, SPDEF, SRSF6, STRA6, SYNM, TBCB, TDRD6, TEX26, TMEM253, TNFSF13B, TTC14, TUBA4A, UBB, VAMP8, VGLL2, WASH2P, WNT9B, XBP1, and ZNF789;

(d) comparing, at each selected locus, the hydroxymethylation level of the enriched cell-free DNA in the initial sample with the hydroxymethylation level in the reference profile, to ascertain differences in hydroxymethylation levels between the sample and the reference profile for each biomarker;

(e) generating an initial hydroxymethylation profile for the patient comprising the hydroxymethylation level of the enriched cell-free DNA in the initial sample, at each selected locus;

(f) repeating steps (a) through (c) at a later time with a subsequent cell-free DNA sample obtained from the patient;

(g) generating a subsequent hydroxymethylation profile for the patient comprising the hydroxymethylation level of the enriched cell-free DNA in the subsequent sample, at each selected locus;

(h) comparing, at each selected locus, the hydroxymethylation level of the enriched cell-free DNA in the subsequent hydroxymethylation profile to the hydroxymethylation level of the enriched cell-free DNA in the initial hydroxymethylation profile, to ascertain a change in the pancreatic lesion; and (i) identifying a change in the patient's hydroxymethylation profile that correlate with a progression toward cancer; and (j) commencing the adminstration of treatment for PDAC and its variants after a change has been identified in step (i).

2. The method of claim 1, wherein the cell-free DNA sample is extracted from a blood sample.

3. The method of claim 1, wherein the cell-free DNA sample is extracted from pancreatic cyst fluid.

4. The method of claim 1, wherein the hydroxymethylation biomarkers additionally comprise loci that are associated with one or more of the following genes: GATA4, GATA6, PROX1, ONECUT2, YAP1, TEAD1, ONECUT2/ONECUT1-TCGA, IGF1, and IGF2.

5. The method of claim 1 wherein the treatment of step (j) comprises radiation therapy, chemotherapy, pharmacotherapy, surgical resection of the lesion, or a combination thereof.

6. The method of claim 1 wherein the sample comprises whole blood, serum, plasma, urine, cyst fluid, or another body fluid comprising hydroxymethylation biomarkers related to the presence, absence, or risk of PDAC and its variants.

* * * * *